United States Patent [19]

Yamazaki et al.

[11] Patent Number: 5,169,757

[45] Date of Patent: * Dec. 8, 1992

[54] ANTIBODIES OR ANTIGENS BOUND TO A MACROPOROUS HYDROPHOBIC SYNTHETIC POLYMER CLOTH FOR IMMUNOLOGICAL TECHNIQUES

[75] Inventors: Hiroshi Yamazaki, Nepean; Burton W. Blais, Ottawa, both of Canada

[73] Assignee: Carleton University, Ottawa, Canada; a part interest

[*] Notice: The portion of the term of this patent subsequent to Jun. 16, 2009 has been disclaimed.

[21] Appl. No.: 538,101

[22] Filed: Jun. 14, 1990

Related U.S. Application Data

[63] Continuation-in-part of Ser. No. 99,393, Sep. 21, 1987, abandoned.

[30] Foreign Application Priority Data

May 20, 1987 [CA] Canada .................................. 537521

[51] Int. Cl.⁵ ................. G01N 33/535; G01N 33/545; C07K 17/08
[52] U.S. Cl. ..................................... 435/7.92; 435/7.9; 435/7.93; 435/7.94; 435/180; 436/531; 436/544; 436/547; 436/823; 436/824; 530/413; 530/815
[58] Field of Search ...................... 435/7.9, 7.92, 7.93, 435/7.94, 174, 177, 179, 180; 436/528, 531, 544, 547, 823, 824; 530/413, 815

[56] References Cited

U.S. PATENT DOCUMENTS 4,200,690 4/1980 Root et al. ........................... 435/174
4,617,326 10/1986 Bjornberg et al. ................... 523/111
4,693,985 9/1987 Degen et al. .................... 435/180 X
4,808,530 2/1989 Means et al. ......................... 435/180

OTHER PUBLICATIONS

Morris, et al. Immunoassays in Food Analysis, Elsevier Applied Science Publishers, N.Y. 1985, pp. 153-171.
Yamazaki, et al., Biotechnology Letters, vol. 8, No. 2, 1986, pp. 107-110.

Primary Examiner—David M. Naff
Attorney, Agent, or Firm—Harry M. Weiss

[57] ABSTRACT

A device for immunological techniques is prepared containing a macroporous hydrophobic synthetic polymer cloth having antibodies or antigens directly adsorbed therein and directly absorbed and immobilized thereon. The cloth has a thickness of more than about 200 μm and has spaces between fibres exceeding about 20 μm in diameter, and preferably has a Frazier Air permeability, in CFM/ft² at 0.5" H₂O of from about 215 to about 750 for thickness of from about 11 to about 40 mils such that it can accommodate a large volume of liquid per surface area, that it has a large surface area, and that it has minimum flow resistance. In immunoassays antibodies may be directly adsorbed therein and directly absorbed and immobilized thereon, and specific antigens from a selected test sample, may then be captured by the antibodies, to be detected conventionally. Alternatively antigens may be directly adsorbed therein and directly absorbed and immobilized thereon, and specific antibodies from a selected test sample, may be captured by the antigens, to be detected conventionally. This device can also be used for extraction and concentration of lipopolysaccharide antigens and for preparing biotinylated, affinity-purified antibodies.

26 Claims, 10 Drawing Sheets

●,■ POLYESTER CLOTH; ○,□, MICROTITER PLATE;
○,●, ANTI-BSA SERUM;
□,■ 'NORMAL' RABBIT SERUM.

SYMBOLS: ●, ■, POLYESTER CLOTH; ○, □, MICROTITER PLATE;
○, ●, ANTI-BSA SERUM; □, ■ 'NORMAL' RABBIT SERUM.

SYMBOLS: S. TYPHIMURIUM (○), S. TYOHOSA (●), S. MINNESOTA (▲), S. ENTERITIDIS (△), OR NO LPS (□).

SYMBOLS: 2 (●), 5 (○), OR 10 min (△).

SYMBOLS: DILUTED 1:10 (●), 1:100 (○), 1:1000 (▲),
1:10,000 (△), OR 1:20,000 (■) IN PBS.

SYMBOLS: HEATED AT 100°C FOR 10 MINS (●)
LEFT AT ROOM TEMPERATURE (○)

SYMBOLS: HEATED AT 100°C FOR 10 MIN (●)
(UNTREATED SAMPLE) LEFT AT ROOM TEMPERATURE (o).

SYMBOLS: SALMONELLA CELLS (●),
PBS ALONE (o)

SYMBOLS: ASSAYED BY THE CEIA AFTER (●) OR BEFORE (○) CONCENTRATION ON ANTIBODY-COATED CLOTH.

SYMBOLS: INCUBATED WITH ANTISERUM (●) OR NORMAL SERUM (○).

SYMBOL: INCUBATED WITH ANTISERUM (●)

SYMBOLS: CAPTURED ANTIGENS DETECTED USING BIOTINYLATED ANTIBODIES (EITHER B-Ab I (●), OR B-Ab II (○)), OR A CSA-1 ANTIBODY-ALKALINE PHOSPHATASE CONJUGATE (▲).

ANTIBODIES OR ANTIGENS BOUND TO A MACROPOROUS HYDROPHOBIC SYNTHETIC POLYMER CLOTH FOR IMMUNOLOGICAL TECHNIQUES

BACKGROUND OF THE INVENTION

Related Application

This invention is a continuation-in-part of copending Application Ser. No. 099,393 filed Sep. 21, 1987, now abandoned, the entire contents of which are incorporated herein by reference.

FIELD OF THE INVENTION

This invention relates to the detection of antibodies, antigens or haptens based on immunoassay techniques.

This invention also relates to a hydrophobic cloth useful as an adsorbent for field enzyme immunoassays.

This invention also relates to a cloth-based enzyme immunoassay to obtain significant enzyme immunoassay signals during the initial stage of immunoreaction.

This invention also relates to a cloth-based enzyme immunoassay to provide a rapid assay for any antibody in any body fluid, e.g., blood, saliva, for example for anti-Salmonella antibodies in chicken egg yolks.

This invention also relates to a cloth enzyme immunoassay for the concentration of dilute antigens by filtration of large volumes of test sample through antibody-coated cloth.

This invention also relates to the preparation and use of biotinylated antibodies and avidin- or streptavidin-enzyme conjugates.

DESCRIPTION OF THE PRIOR ART

An antigen is an extraneous substance which, when introduced into the body of vertebrates, causes the production of an antibody which can specifically complex with that antigen. Any sub-substance, for example a protein, which is not normally present in certain organisms, can cause the formation of antibodies when it infiltrates into or is applied to an organism under suitable conditions. An antibody once produced is also capable of binding a hapten, i.e., a relatively small and simple compound which may be the determinant group of a given antigen. The hapten is capable of binding with the specific antibody but is incapable itself of giving rise to the production of an antibody, unless it is bound to an antigenic carrier. These small molecular weight antigens (haptens) may require conjugation with large molecular weight carriers in order to elicit antibody production. This antigen-antibody complexing is the basis of immunoassays.

The binding interaction between an antigen or a hapten and its antibody is specific and sensitive. Other types of materials that participate in similar specific and sensitive binding interactions are: enzymes and their substrates; hormones; vitamins; metabolites; and pharmacological agents; and their receptors and binding substances.

Since virtually any foreign compound can be made immunogenic, the domain of immunoassays is unlimited.

Diagnostic tests claim a large share of the health care market. In both human and veterinary medicine, the definitive diagnosis of infectious diseases require the demonstration of the infectious agents or their components. Traditional cultural methods for the detection of pathogens are slow, expensive and of uncertain sensitivity, and require extensive laboratory facilities. To overcome some of these disadvantages, specific binding assay techniques have provided analytical methods for determining various organic substances of diagnostic, medical, environmental and industrial importance which appear in liquid mediums at very low concentrations. Specific binding assays are based on the specific interaction between the ligand, i.e. the bindable analyte under determination, and a binding partner therefor. When one of the ligand and its binding partner is an antibody and the other is a corresponding hapten or antigen, the assay is known as an immunoassay. In addition several immunological tests are now commercially available, namely: agglutination tests; immunofluorescent tests; and enzyme immunoassays. However, many of these tests require the use of microscopes, spectrophotometers, or other laboratory facilities, limiting their use under field conditions. Prompt and effective control of diseases depends on rapid and simple field tests.

Radioimmunoassay employs a radioactive isotope as the label. Such an assay necessarily must follow the heterogeneous format since the monitor character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, e.g. chemiluminescence, fluorescence emission, or color change, related to the presence of amount of the ligand under assay in the liquid sample.

Immunoassays diagnose infectious diseases by detecting either increased titers of antibodies against pathogen antigens or the presence of the pathogens or their antigens. Antigen assays offer more definitive diagnosis of infectious diseases as the capacity to produce antibodies remains in subjects which have recovered from the disease or have previously been vaccinated.

Enzyme immunoassays use enzyme-labeled immunoreagents (antibodies or antigens) for the detection of antigens or antibodies captured in a solid phase. Adsorption onto an easily recoverable solid phase is a simple and rapid means of immobilization of immunoreactants for the subsequent capture of antigens or antibodies from a test sample. Since antibodies and many antigens contain hydrophobic regions in their structures, they bind readily to hydrophobic surfaces. Most commonly used enzyme immunoassays depend on the adsorption of immunoreactants onto either a flat solid surface or a solid membrane. Solid phases, e.g. microtiter plates, tubes or beads, and plastics, e.g. polystyrene, polyvinyl chloride, nylon, and polymethacrylate have commonly been used. Although nitrocellulose membranes have been used to adsorb antigens as well as antibodies, these are thin and can only accommodate a small volume of test sample which has a limited contact with the surface area. Furthermore, since their pore sizes are small, their effective washing requires a vacuum suction apparatus which holds them airtight.

Enzyme immunoassay is therefore now used for the detection of a variety of antigens (or haptens), e.g., microbial contaminants and pathogens, toxins, and environmental pollutants. The simplest form of the assay involves the immobilization of an immunoreactant (antibody or antigen) on a solid phase to capture the test substance which is then detected with a specific antibody-enzyme conjugate. Commonly, and as normally presently used, the immunoreactant is immobilized by adsorption onto non-porous solid phases of microtiter plates, tubes or beads which are made of hydrophobic synthetic plastic materials, e.g., polystyrene, polyvinyl chloride or polymethacrylate. The quantitative enzyme immunoassay of specific antibodies as used in disease diagnoses is commonly performed by either of two methods using antigen immobilized on a microtiter plate. The first "endpoint" method involves serial dilutions of the test sample in order to determine the highest dilution ("titer") which produces a signal nearest an arbitrarily assigned endpoint. The second method uses a fixed sample dilution and then measures the extent of immunoreaction with a fixed amount of immobilized antigen. Both methods rely on the completion of each immunoreaction which usually requires in excess of 30 minutes. It is theoretically possible to assay antibodies on the basis of the initial rate of antibody binding to the immobilized antigen during the instantaneous exposure of the antigen-coated solid phase to the antibody solution. However, such a strategy is rarely used because short immunoreactions on non-porous solid phases, e.g., microtiter plates, do not yield significant signals. Because of limited surface areas, each immunoreaction on the non-porous phases usually requires more than an hour. Tests under field conditions (e.g. processing plants, farms, homes and doctor's offices) would benefit from faster and simpler enzyme immunoassay.

Biotinylated antibodies and avidin-(or streptavidin-) enzyme conjugates have become a popular combination for the detection of antigens captured by immobilized antibodies in enzyme immunoassay since it provides greater sensitivity than direct antibody-enzyme conjugates. Therefore, a variety of avidin-(or streptavidin-) enzyme conjugates are commercially available. The preparation of biotinylated antibodies involves the purification of the desired antibodies, which are then biotinylated in free solution. The entire procedure commonly requires a few days to complete.

The patent literature is replete with descriptions of techniques and means for effecting immunoassays. A representative selection of such patents include the following:

1) Canadian Patent 1,031,257 issued May 16, 1978 to R. Dietrich, which was directed to a device comprising an immunologically-reactive material on an object carrier or a film, the immunologically-reactive material being in a lyophilised and self-adhering form.

2) Canadian Patent No. 1,060,342 issued Aug. 14, 1979 to O. Lostia et al, which was directed to a polymeric structure comprising a porous artificial fibre where the substance occluded in the fibre was antibodies, antigens or antisera, and where the pores of the fibre were of such nature as to prevent escape of the occluded substance but to allow for the penetration of the agent that was to be reacted with that substance.

3) Canadian Patent No. 1,083,036 issued Aug. 5, 1980 to G. Bolz, which was directed to a specifically-described procedure for determining reacted labeled antibodies.

4) Canadian Patent No. 1,107,195 issued Aug. 18, 1981 to D. Wagner et al, which provided a specific binding assay method using nonion-exchange cross-linked polystyrene for determining a ligand in, or the ligand-binding capacity of, a liquid medium.

5) Canadian Patent No. 1,108,986 issued Sep. 15, 1981 to D. Wagner et al, which provided a specific binding assay method using nonion-exchange cross-linked polyvinyl alcohol for determining a ligand in or the ligand binding capacity of a liquid medium.

6) Canadian Patent No. 1,152,430 issued Aug. 23, 1985 to J. Gordon et al, which was directed to a solid support for proteins consisting of a porous nitrocellulose sheet containing an electrophoretically transferred replica of an electropherogram of proteins in a gel.

7) Canadian Patent No. 1,199,269 issued Jan. 14, 1986 to V. A. Marinkovitch, which was directed to a diagnostic kit which included a support having a plurality of cotton threads supported in a predetermined spaced relation for simultaneous contact with a liquid test sample.

8) U.S. Pat. No. 3,552,928, patented Jan. 5, 1971 by M. C. Fetter, which provided means for separating whole blood into a substantially-colorless fluid and the red cell components or residue. According to this patent, a matrix containing the amino acid or derivative thereof is positioned adjacent to a test reagent specifically reactable with, and giving a detectable response to, the soluble constituent of whole blood. The whole blood was first contacted with the amino acid. The colorless fluid thus obtained was then contacted with the test reagent.

9) U.S. Pat. No. 3,917,527, patented Nov. 4, 1975 by S. Shaltiel, which provided means for the selective and reversible binding of a macromolecule to a specifically-recited adsorbent. It also provided a package containing a series of small chromagraphic columns which were said to be useful for rapid identification of the specific adsorbent most effective in the purification of a particular macromolecule. The adsorbent was a water-soluble porous solid matrix support having hydrocarbon arms attached thereto.

10) U.S. Pat. No. 3,951,741 patented Apr. 20, 1976 by R. F. Devlin, which was directed to a specific sensitized matrix for diagnosing both infectious and non-infectious diseases, including an insoluble, inert, pliable and wettable matrix having a network of pores, and a protein polymer network immobilized in that network of pores.

11) U.S. Pat. No. 4,013,514, patented Mar. 22, 1977 by B. S. Wilde, which provided water-insoluble, biologically-active conjugates for use in a reactor core of a flow-through reactor which were prepared by covalently bonding an enzyme directly to a fibrous dialdehyde cellulose, e.g., cotton, methylcellulose, carboxymethyl cellulose, regenerated cellulose, and the like, at least some glucoside units of which have been oxidized to dialdehyde groups and which was substantially neutral, i.e. which was substantially free from carboxyl groups.

12) U.S. Pat. No. 4,168,146 patented Sep. 18, 1979 by A. O. Grubb et al, which was directed to a diagnostic test device useful for immunochemical quantification, which was a carrier strip comprising a silica-modified micro-porous polymer having finely-divided silica substantially-uniformly embedded in a particularly-recited permeable, continuous polymeric matrix.

13) U.S. Pat. No. 4,200,690, patented Apr. 29, 1980 by D. M. Root, et al, which provided a device for the detection of the presence of antigens. The device had an antibody immunochemically reactive with the antigen bound to a first microporous membrane coated with an inert proteinaceous material and an antibody immunochemically non-reactive with the antigen bound to a second mocroporous membrane coated with an inert proteinaceous material.

14) U.S. Pat. No. 4,277,561 patented Jul. 7, 1981 by D. Monget et al, which was directed to a support for the determination of enzyme activity in a biological extract wherein the support comprised a fibrous material impregnated with a substrate and a particularly-recited water-soluble pH stabilizer.

15) U.S. Pat. No. 4,347,311 patented Aug. 31, 1982 by H. H. Schmitz, which was directed to a highly sensitive enzyme immunoassay procedure for determining antibodies which were specific to antigens by coating a particularly-recited solid support with an antibody.

16) U.S. Pat. No. 4,442,204 patented Apr. 10, 1984 by A. C. Greenquist, which was directed to a test device comprising a solid carrier member, e.g., a fibrous web matrix, e.g. paper, or a polymeric film or gel, incorporated with specifically-recited reagents for a homogeneous specific binding assay system.

SUMMARY OF THE INVENTION

Aims of the Invention

The interrelationship between a substrate and an antibody should be such that non-specific binding of antibodies to a substrate should be reduced while allowing detection of immunologically reactive protein levels when antigen antibodiy complexes are identified with an agent. (See Spinola et al, Journal of Immunological Methods, (81 (1985) 161-165). It is also known that the simple manipulations required to separate free antibody or antigen from immune compleses immobilized non-covalently on plastic solid phase is probably the most important reason for the rapid increase in popularity of enzyme immunoassay. Desired traits of the solid phase are: (i) high capacity for binding immunoreactants (high surface/volume ratio); (ii) possibility of immobilization of many different immunoreactants; (iii) minimal dissociation; (iv) negligible denaturation of immobilized molecule; and (v) orientation of immobilized antibody with binding sites towards the solution and the Fe to the solid phase.

Plastic is by far the most popular solid phase, since it makes the procedures extremely simple. However, plastics also have some important limitations: (i) they are immunoreactant-comsumptive, i.e., often require 10 times more reactants than particulate solid phases or membranes; (ii) the avidity of immobilized antibodies for large antigens decreases by 1-2 orders of magnitude, probably due to the wide spacing of epitopes or paratopes; and (iii) the rate of antibody-antigen interactions is slower than in solution or with particulate solid phases (hours instead of minutes), due to the necessity of the free immunoreactant to diffuse to the solid phase (association kinetics is largely dictated by diffusion rates (See P. Tijssen, "Practice and Theory of Enzyme Immunology" p. 297, Elsevier, 1985, Amsterdam, N.Y., Oxford).

Accordingly, those concerned with the development and use of immunoassay techniques and related devices have recognized the desirability for further improvements and it is therefore one object of the invention to provide a rapid, accurate method for the quantitative determination of an antigen on a solid surface or for the quantitative determination of an antibody on a solid surface.

A further object of the invention is to provide a method to provide rapid and sensitive immunoassays.

A still further object of the present invention is the provision of a relatively simple yet high effective and sensitive diagnostic test for the detection of specific disease states, both infectious and non-infectious.

Yet another object of this invention is the use of the hydrophobic cloths to make immunoassays rapid and simple.

Yet another object of this invention is to enable the use of hydrophobic cloths for immunoassays for antigens and haptens as well as for antibodies.

Another object of this invention is to prove an adsorbent for enzyme immunoassay, which is superior to the conventional non-porous microtiter plate in that it can provide a much larger surface area for immunoreactions (thus, faster reactions), can accommodate a larger volume of sample per unit area (thus giving more extensive reactions), and permits easier washing.

Still another object of the present invention is to provide a method involving the use of body fluids for the rapid assay of specific antibodies to provide a simpler, and less time consuming procedure and would eliminate trauma to the animals incurred by bleeding, e.g., to provide a method involving the use of egg yolk rather than serum for the detection of specific antibodies in the routine monitoring of flocks for exposure to Salmonella to provide a simpler, and less time consuming procedure and would eliminate trauma to the animals incurred by bleeding.

Another object of the present invention is to provide a rapid and simple procedure for the affinity purification and biotinylation of antibodies on antigen-coated cloths, to enable the rapid and simple preparation of an immunoreagent suitable for enzyme immunoassay.

STATEMENTS OF INVENTION

By this invention, an immunoassay device is provided comprising the combination of a macroporous hydrophobic synthetic polymer cloth having a thickness of more than about 200 $\mu$m and having spaces between fibres exceeding about 20 $\mu$m in diameter, the cloth preferably having a Frazier Air Permeability, in CFM/ft$^2$ at 0.5" H$_2$O of from about 215 to about 750 for thickness of from about 11 to about 40 mls respectively, the cloth having a structure such that it can accommodate a large volume of liquid per surface area thereof, that it has a large surface area and that it has minimum flow resistance, and an antibody directly adsorbed thereon, and directly absorbed therein. The test for Frazier Air permeability is described in ASTM D737-75 "Standard Test Method for Air Permeability of Textile Fabrics" which involves the use of apparatus available from Frazier Precision Instrument Co.

The present invention also provides an enzyme immunoassay device comprising the combination of a macroporous hydrophobic synthetic polymer cloth having a thickness of more than about 200 $\mu$m and having spaces between fibres exceeding about 20 $\mu$m in diameter, the cloth preferably having a Frazier Air Permeability, in CFM/ft$^2$ at 0.5" H$_2$O of from about 215 to about 750 for thickness of from about 11 to about 40 mls respectively, the cloth having such a structure that it can accommodate a large volume of liquid per surface area thereof, it has a large surface area, and it has minimum flow resistance, and antigen directly adsorbed therein and directly absorbed and immobilized thereon.

The present invention also provides an immunoassay device comprising the combination of a macroporous hydrophobic synthetic polymer cloth, the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, antibodies directly adsorbed therein and directly absorbed and immobilized thereon, and specific antigens from a selected test sample, captured by the adsorbed, absorbed and immobilized antibodies.

The present invention also provides an immunoassay device comprising the combination of a macroporous hydrophobic synthetic polymer cloth, the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, antigens directly adsorbed therein and directly absorbed and immobilized thereon, and specific antibodies from a selected test sample, captured by the adsorbed, absorbed and immobilized antigens.

The present invention also provides an immunoassay device comprising the combination of a macroporous synthetic polymer cloth, the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, a coating of a suitable adsorbable antigen directly adsorbed thereon and directly absorbed therein, and antibodies in an antiserum immunoadsorbed on the antigen coating.

The present invention also provides an immunoassay device comprising the combination of a macroporous synthetic polymer cloth, the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, a coating of a lipopolysaccharide directly adsorbed thereon and directly absorbed and immobilized therein, and antibodies in an antiserum immunoadsorbed on the lipopolysaccharide coating.

The term "macroporous" as applied to cloths when used herein is intended to mean textiles composed of hydrophobic synthetic polymeric fibers, which are either woven or non-woven into a physically structurally stable cloth of more than 200 μm thickness, such that the pores (i.e., spaces between the fibers) exceed 20 μm in diameter.

This invention also provides an immunoassay method for detecting an antigen, comprising the steps of: a) treating a surface of a macroporous hydrophobic synthetic polymer, cloth the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, with an antibody, thereby to have the antibody directly adsorbed thereon and directly absorbed and immobilized therein, thereby to provide an immunoassay cloth; b) incubating the immunoassay cloth with a sample to be tested for the antigen, thereby to adsorb an antigen therein and to provide an antigentreated incubated cloth; c) washing the antigen-treated incubated cloth with a buffer to remove unadsorbed material; d) incubating the washed cloth with an enzyme-antibody conjugate prepared by coupling purified antibodies specific for the antigen to be assayed, thereby to provide an incubated cloth; e) washing the incubated cloth with a buffer to remove unreacted conjugate; and f) detecting remaining enzyme-antibody conjugate by incubating the washed incubated cloth in a chromogenic substrate indicator solution to produce a visible colour upon product formation.

The invention also provides an immunoassay method for detecting an antigen, comprising the steps of: a) treating a surface of a macroporous hydrophobic synthetic polymer cloth, the cloth having a thickness more than about 200 μm and having spaces between fibres exceeding about 20 μm in diameter, the cloth preferably having a Frazier Air Permeability in CFM/ft² at 0.5" H₂O of from about 215 to about 750 for thicknesses of about 11 mils to about 40 mils, respectively, the cloth thereby having a structure so that it can accommodate a large volume of liquid per surface area, it has a large surface area and it has a minimum flow resistance, with an antibody, thereby to have an antibody directly adsorbed thereon and directly absorbed and immobilized therein, and thereby to provide an intermediate immunoassay cloth; b) applying to the surface of the intermediate immunoassay cloth, a mixture of the antigen being assayed and an enzyme-antibody conjugate prepared by coupling purified antibodies specific for the antigen being assayed, thereby to provide an immunoassay cloth; c) treating a control identical macroporous hydrophobic synthetic polymer cloth with a mixture of the antiben being assayed and an enzyme-antibody conjugate prepared by coupling purified antibodies specific for the antigen being assayed, to provide a control cloth; d) incubating both the immunoassay cloth and the control cloth substantially simultaneously; e) washing the incubated immunoassay cloth and the incubated control cloth with an identical buffer solution; and f) detecting the antigen by incubation of both the immunoassay cloth and the control cloth in a chromogenic substrate indicator solution to produce a visible colour upon product formation, the amount of antigen being determined by the difference in intensity of the colour between the control cloth and the immunoassay cloth.

This invention also provides an immunoassay method for detecting an antibody, comprising the steps of: a)

treating a surface of a macroporous hydrophobic synthetic polymer cloth, the cloth having a thickness more than about 200 μm and having spaces between fibres exceeding about 20 μm in diameter, the cloth preferably having a Frazier Air Permeability in CFM/ft$^2$ at 0.5" H$_2$O of from about 215 to about 750 for thicknesses of about 11 mils to about 40 mils, respectively, the cloth thereby having a structure so that it can accommodate a large volume of liquid per surface area, it has a large surface area and it has a minimum flow resistance, with an antigen, thereby to have an antigen directly adsorbed thereon and directly absorbed and immobilized therein, to provide an immunoassay cloth; b) incubating the immunoassay cloth with a sample to be tested for the antibody, thereby to adsorb antibody therein and to provide an incubated cloth; c) washing the incubated cloth with a buffer to remove unadsorbed material and to provide a washed cloth; d) incubating the washed cloth with an enzyme-antiglobulin antibody conjugate prepared by coupling purified antigens specific for said antibody to be assayed; e) washing the incubated cloth with a buffer to remove unreacted conjugate; and f) detecting remaining enzyme-antiglobulin antibody conjugate by incubating the washed incubated cloth in a chromogenic substrate indicator solution to produce a visible colour upon product formation.

This invention also provides an immunoassay method for detecting an antibody, comprising the steps of: a) treating a surface of a macroporous hydrophobic synthetic polymer cloth, the cloth having a thickness more than about 200 μm and having spaces between fibres exceeding about 20 μm in diameter, the cloth preferably having a Frazier Air Permeability in CFM/ft$^2$ at 0.5" H$_2$O of from about 215 to about 750 for thicknesses of about 11 mils to about 40 mils, respectively, the cloth thereby having a structure so that it can accommodate a large volume of liquid per surface area, it has a large surface area and it has a minimum flow resistance, with an antibody specific for an antigen, thereby to have an antigen directly adsorbed thereon and directly absorbed and immobilized therein, thereby to provide an intermediate immunoassay cloth; b) applying to the surface of the intermediate immunoassay cloth, a mixture of the antibody being assayed and an enzyme-antigen conjugate prepared by coupling purified antigens specific for the antibody being assayed thereby to provide an immunoassay cloth; c) treating a control identical macroporous hydrophobic synthetic polymer cloth with a mixture of the antibody being assayed and an enzyme-antigen conjugate prepared by coupling purified antigens specific for the antibody being assayed, to provide a control cloth; d) incubating both the immunoassay cloth and the control cloth substantially simultaneously; e) washing the incubated immunoassay cloth and the control cloth with an identical buffer solution; f) and detecting the antibody by incubation of both the immunoassay cloth and the control cloth in a chromogenic substrate indicator solution to produce a visible colour upon product formation, the amount of antibody being determined by the difference in intensity of the colour between the control cloth and the immunoassay cloth.

This invention also provides a method for the extraction of lipopolysaccharide antigens from solid samples, and for the concentration of such antigens which are present in large volumes of sample, onto an antibody-coated macroporous hydrophobic cloth, said cloth having a thickness more than about 200 μm and having spaces between fibres exceeding about 20 μm in diameter, the cloth preferably having a Frazier Air Permeability in CFM/ft$^2$ at 0.5" H$_2$O of from about 215 to about 750 for thicknesses of about 11 mils to about 40 mils, respectively, the cloth thereby having a structure so that it can accommodate a large volume of liquid per surface area, it has a large surface area and it has a minimum flow resistance for subsequent detection on the cloth by cloth enzyme immunoassay techniques, which method comprises the steps of: a) heating a solid sample containing the antigen in the presence of a chelating agent for short period of time, thereby to chelate divalent cations, and to disrupt the lipopolysaccharide-containing outer membrane of Gram-negative bacteria; b) recovering the lipopolysaccharide antigens in non-sedimentable form; c) separating the antigens to obtain a solid-free liquor; and d) using the solid-free liquor as the sample for carrying out the concentration.

The method of this embodiment of the invention provides for the extraction of antigens, e.g., lipopolysaccharide antigens, from solid samples, as well as for the concentration of such antigens, present in large volumes of sample, onto antibody-coated macroporous polyester cloth as hereinabove described for subsequent detection on the cloth by cloth enzyme immunoassay, to raise the effective sensitivity of the cloth enzyme immunoassay.

The present invention also provides an immunoassay procedure comprising a) capturing specific antibodies, e.g., either in rabbit serum or in chicken egg yolk, onto a macroporous polyester cloth, the cloth preferably having a Frazier Air Permeability, in CFM/ft$^2$ at 0.5" H$_2$O of from about 215 to about 750 for thickness of from about 11 to about 40 mls, the cloth having such a structure that it can accommodate a large volume of liquid per surface area thereof, it has a large surface area, and it has minimum flow resistance, the cloth being coated with a suitable antigen, e.g., Salmonella lipopolysaccharide; and b) detecting the antibodies using a suitable conjugate, e.g., an anti-chicken IgG-peroxidase conjugate.

Other Features of the Invention

It is believed that a cloth material as described above is advantageous for enzyme immunoassay since, unlike microporous or non-porous solid phases of the prior art (e.g., membranes, beads): (1) it permits the easy passage of wash buffer for the quick and effective washing of the cloth between immunoreactions to remove unreacted components, without the use of vacuum apparatus, etc., (cloth can be washed simply by placing on an absorbent pad and rinsing with a few drops of wash buffer); (2) macroporous cloth can accommodate a larger volume of liquid sample per area for more extensive reaction with the immobilized immunoreagents; and (3) cloth provides a much larger surface area for immunoreactions than non-porous solid phases (e.g., plastic tubes, microtiter plates, etc.). Macroporous cloths of hydrophobic fibers would provide a much larger surface area, accommodate a larger volume of sample, and allow for easier washing. Furthermore, such cloths are readily available and economical.

By one feature of this invention, the above-described macroporous hydrophobic synthetic polymer cloth is selected from the group consisting of woven or non-woven polypropylene, polyester, nylon, and polyethylene cloths.

One specific and preferred example of such non-woven polyester cloths is that known by the trade-mark SONTARA of Dupont. The following table lists some typical properties a SONTARA TM in English Units.

Salmonella antibodies and the macroporous synthetic polymer cloth preferably is a polyester cloth.

| Style 100% Polyester | UNIT WEIGHT (oz/yd.$^2$) | THICK-NESS (mils) | SHEET GRAB TENSILE (lbs) | | TRAPEZOID TEAR (lbs) | | MULLEN BURST (psi) | FRAZIER AIR PERMEABILITY (CFM/ft$^2$ @ 0.5" H$_2$O) | ROLL SIZE (7" ID CORE) | |
|---|---|---|---|---|---|---|---|---|---|---|
| | | | MD | XD | MD | XD | | | in. O.D. | lin. yds. |
| 8000 | 1.2 | 14 | 23 | 14 | 6 | 5 | 40 | 500 | 44 | 4600 |
| 8001 | 1.0 | 11 | 17 | 8 | 7 | 3 | 23 | 600 | 44 | 5000 |
| 8010** | 1.3 | 18 | 25 | 14 | 7 | 5 | 33 | 750 | 44 | 4500 |
| 8100 | 4.0 | 40 | 70 | 45 | 35 | 40 | 120 | 215 | 44 | 1700 |
| 8103 | 2.0 | 22 | 40 | 22 | 14 | 8 | 50 | 290 | 44 | 3500 |
| 8122** | 2.4 | 27 | 45 | 25 | 15 | 7 | 57 | 320 | 44 | 2500 |
| 8215** | 1.8 | 17 | 31 | 16 | 11 | 5 | 44 | 420 | 44 | 4000 |

In another feature of this invention, the specific antibodies captured on the cloth are detectable using a suitable conjugate, e.g., those specific antibodies are detectable using an antiglobulin antibody-enzyme conjugate, the conjugate binding to the captured antibodies, the conjugate being assayable using a chromogenic substrate.

The immunoassay device of another feature of this invention further comprises the combination of the above-described macroporous hydrophobic synthetic polymer cloth, bovine serum albumin (BSA) directly adsorbed therein and directly absorbed and immobilized thereon, and anti-BSA immunoglobulin G antibody (IgG) in rabbit serum captured therein by the BSA. In such immunoassay device, the captured anti-BSA IgG are detectable using an antirabbit IgG peroxidase conjugate.

The immunoassay device of yet another feature of the invention further comprises the combination of the above-described macroporous hydrophobic synthetic polymer cloth, Salmonella lipopolysaccharide directly adsorbed thereon and directly absorbed and immobilized therein, and specific antibodies in egg yolk, which have been captured therein by the Salmonella lipopolysaccharide. In such immunoassay device, the captured specific antibodies in egg yolk are detectable using an antichicken IgG-peroxidase conjugate.

The immunoassay device of still another feature of the invention further comprises the combination of the above-described macroporous hydrophobic synthetic polymer cloth, Salmonella lipopolysaccharide directly adsorbed and coated thereon and directly absorbed therein, and goat anti-Salmonella antibody standards which have been captured by the Salmonella lipopolysaccharide. In such an immunoassay device, the captured antibodies are assayable colourimetrically using an anti-goat antibody-peroxidase conjugate.

The immunoassay device of a still further feature of the invention still further comprises the combination of the above-described macroporous hydrophobic synthetic polymer e.g., polyester, cloth, a coating of an appropriate antigen directly adsorbed thereon and directly absorbed therein, and antibodies in an antiserum immunoadsorbed on the antigen coating.

The immunoassay device of a still further feature of the invention still further comprises the combination of the above-described macroporous hydrophobic synthetic polymer cloth, a coating of a lipopolysaccharide directly adsorbed thereon and directly absorbed therein, and antibodies in an antiserum immunoadsorbed on the lipopolysaccharide coating. In such an immunoassay device, the antibodies preferably are anti- By another feature of this invention, the above-described immunoassay devices may be treated with an antiserum containing an antibody specific for the antigen being tested.

By yet another feature such immunoassay devices may be treated with a purified antibody bearing the appropriate specificity.

By still another feature, such antibodies present in the antiserum may be partially denatured prior to being applied to the above-described macroporous hydrophobic synthetic polymer cloth, e.g. by exposure to a low pH environment, e.g., a pH of 2.5, or by heating.

Alternatively, by yet another feature, the antibodies may be affinity-purified prior to being so-applied to the macroporous hydrophobic synthetic polymer cloth.

By still another feature, the antibody may be provided by diluted antiserum.

By yet another feature, it is preferred that the immunoassay device of embodiments of the invention, be in the form of the above-described macroporous hydrophobic synthetic polymer cloth bonded to a different material, thereby to provide an antibody-coated test strip that may be handled throughout an assay procedure. Thus, the present invention embraces the bonding, in any suitable manner, of the so-treated macroporous hydrophobic synthetic polymer cloth to a dipstick.

By yet another feature, it is preferred that the immunoassay device of embodiments of the invention, be in the form of a large sheet of the above-described macroporous hydrophobic synthetic polymer cloth onto which multiple samples can be blotted thereby to provide an antibody-coated test sheet that may be used to test multiple samples in an assay procedure.

GENERALIZED DESCRIPTION OF THE INVENTION

Consequently, there are three main aspects of the present invention. One aspect resides in the rapid assay of specific antibodies using antigen-coated cloth.

As an example, of such aspect, anti-Salmonella antibodies (either purified goat antibodies or from the serum of an immunized rabbit) may be rapidly captured and detected on Salmonella lipopolysaccharide-coated cloth. Another example may be the detection of anti-Salmonella antibodies in chicken egg yolk. The invention encompasses the rapid detection of any specific antibodies (in body fluid) using antigen-coated cloth. Rapidity of the assay (immunoreactions) is a key feature.

Another aspect resides in the extraction and concentration of lipopolysaccharide antigens or antibody-coated cloth.

One example, of such aspect, is the extraction of Salmonella lipopolysaccharide antigens using ethylenediaminetetraacetate, and heat, followed by assay on antibody-cloth. The ethylenediaminetetraacetate heat treatment should be applicable to the extraction of lipopolysaccharide antigens from any Gram negative bacteria. A second, important feature of this invention, is the ability concentrate antigens (in general) present in large volumes of sample onto antibody-coated cloth followed by their cloth enzyme immunoassay thereupon.

A third aspect of this invention resides in the affinity purification and biotinylation of specific antibodies on antigen-coated cloth.

This aspect of the invention employs antigen-coated cloth. This aspect provides a method for the preparation of a reagent useful for enzyme immunoassay. The reagent prepared is an affinity purified biotinylated antibody, useful in enzyme immunoassay (including the cloth enzyme immunoassay).

Consequently, the enzyme immunoassay procedure in one embodiment of this invention may consist of the following: a macroporous hydrophobic synthetic polymer cloth having such porosity that it can accommodate a large volume of liquid per surface area, it has a large surface area and it has a minimum flow resistance is treated to have directly adsorbed thereon and directly absorbed therein, either an antiserum containing antibodies specific for the antigen being tested, or purified antibodies bearing the appropriate specificity, and is subsequently incubated with the test sample purported to contain the antigen. The cloth is then washed with an appropriate buffer to remove any unadsorbed and unabsorbed material, and is then incubated with an enzyme-antibody conjugate prepared by coupling purified antibody specific for the antigen to a suitable indicator enzyme. The cloth is then washed with buffer to remove unreacted conjugate, and the remaining conjugate is detected by incubation in a chromogenic substrate-indicator solution which produces a visible colour upon product formation.

The immunoassay procedure of another embodiment of the invention may consist of the following: a test sample containing the antigen to be assayed is mixed with a suitable enzyme-antibody conjugate, e.g. diluted horseradish peroxidase (HRP)-antibody conjugate specific for the antigen of interest, and an aliquot of this mixture is incubated with an antigen-treated hydrophobic cloth. A control hydrophobic macroporous hydrophobic synthetic polymer cloth is treated with a mixture of the same enzyme-antibody conjugate but without the free antigen. After washing with a suitable buffer solution, e.g. PBST, cloths incubated with an antigen-conjugate mixture fail to produce the same intensity of colours (upon incubation in ABTS-indicator) as cloths incubated with a control mixture consisting of the conjugate in the absence of free antigen.

While it is not desired to be bound by any theory, it is believed that antigen present in the test sample combines with the conjugate, thus preventing its interaction with the antigen-treated cloth. In this manner, the presence of antigen in a test sample will diminish the amount of colour produced in the test, while the control sample (minus free antigen) gives proof of the functional integrity of the conjugate.

The detection of B. abortus antigen LPS, using the immunoassay with LPS-coated macroporous polyester cloth has thus been provided as another embodiment of this invention. The immunoassay, which requires only one incubation with the immunological reagent, provides an internal control for the quality of the reagent used.

The present invention thus provides a simple and rapid method for assaying anti-Salmonella IgG in chicken egg yolk. Polyester cloth coated with Salmonella lipopolysaccharide is used to capture specific antibodies in egg yolk, which are then detected using an anti-chicken IgG-peroxidase conjugate. This assay thus provides a simple and economical means of monotoring the levels of Salmonella contamination in chicken rearing facilities.

The present invention provides a rapid antibody cloth enzyme immunoassay which exploits the advantages of using a macroporous hydrophobic cloth (polyester) as an adsorbent of antigens, which is then used to capture specific antibodies from a test sample, e.g., a patient's serum, saliva, or other fluids. The antibodies captured specifically on the cloth are then detected using an antiglobulin antibody-enzyme conjugate, which binds to the captured antibody. The enzyme itself is assayed using an appropriate chromogenic substrate.

The advantages of using such macroporous hydrophobic synthetic polymer cloth as the immunoadsorbent include the following: (1) because of its macroporosity, the antigen-coated cloth presents a larger surface for immunoreaction with specific antibodies present in a given volume of sample, thus yielding faster immunoreactions than conventional non-porous solid phases, e.g., a microtiter plates; (2) because of its macroporosity, the cloth shows excellent flow (or filtration) characteristics, which in turn enables easy and quick washing with a buffer between each immunoreaction step to remove unbound material (such washing being accomplished by simply placing the cloth on a water-absorbent pad, e.g., a disposable diaper, and allowing the wash buffer to be absorbed through the cloth and into the pad); (3) the ability to wash cloth quickly and easily in this manner allows for the instantaneous exposure of the antigen-cloth to the test sample (such instantaneous exposure being accomplished by passively absorbing a volume of liquid sample through the cloth into the pad, followed immediately by washing with buffer which allows for the rapid and quantitative assay of (e.g.,) antibodies); (4) the ease of effectively washing the cloth on a simple absorbent pad as above allows for the configuration of the assay into a convenient "Field" kit (in which the assay can be performed in the absence of laboratory facilities or sophisticated equipment) where an absorbent pad is packaged in such a way as to allow convenient washing and containment of the washings to prevent release of potentially hazardous sample material into the immediate environment; and (5) the macroporous polyester cloth is economical to use as an immunoadsorbent and easy to handle throughout the assay procedure, since the antigen-cloth can be used in the form of either a dipstick (where a small segment of cloth is fixed to a strip of inert material which allows easy handling), or a large sheet onto which multiple samples can be applied which, in conjunction with the use of a suitable enzyme substrate system yielding an insoluble product, can yield a qualitative test for screening large numbers of samples. In the latter type of assay, termed "dot blot", multiple samples are simultaneously applied as spots on the antigen-cloth sheet, the sheet is immediately washed with buffer, then saturated with antiglobulin antibody-enzyme conjugate and incubated for a fixed period of time (which can vary from 2 to 30 min), washed again with buffer, and then saturated with a solution of indicator substrate which gives an insoluble product upon action of the enzyme. Areas on the sheet where specific antibody was spotted and bound will give a visible coloured spot against a colourless background. Samples in which specific antibodies are lacking will fail to produce visible spots.

The theory of the cloth enzyme immunoassay for the rapid assay of antibodies on the basis of the initial rate of immunoraction is as follows: the rate of association of an antigen with its specific antibody is, under ideal conditions of temperature, ionic strength, and pH, very rapid and the overall rate of immunoreaction in solution is limited mainly by the frequency of intermolecular collisions between the said antigen and antibody.

This frequency, in turn, is dictated by: (1) the distance over which the antibody must travel, by diffusion, before it can encounter the antigen in solution, the greater the distance, the lower the frequency of collisions, and therefore the slower the rate of immunoreaction; and (2) the concentration of either immunoreactant (antigen or antibody) in the solution. The lower the concentration of immunoreactant, the lower the frequency of collisions, etc. When antigen is present in large excess, the rate of immunoreaction will depend chiefly on the concentration of antibody in the solution (i.e. proportionally faster rates with higher concentrations of antibody). This holds true also in the case of an antigen immobilized on a solid phase, which is then exposed to an antibody solution. However, when the antigen is immobilized on a non-porous solid phase, e.g., a microtiter plate, as in the prior art, it has a limited spatial contact with the antibody solution, and diffusion becomes strongly rate-limiting. When the antigen is immobilized on a high-surface area solid phase, e.g., a macroporous synthetic polymer cloth, as in the present invention, diffusion becomes less rate-limiting since the antigen-coated solid phase is in more intimate spatial contact with the test solution. In this case, the antibody will react faster with the antigen-coated solid phase. Thus, for a fixed antibody concentration, a macroporous solid phase, e.g., as polyester cloth, as in the present invention, will react with a greater amount of antibody than a non-porous solid phase such as a mocrotiter plate during a short fixed incubation, consequently, according to the present invention, even during an instantaneous exposure of antigen-coated macroporous polyester cloth to an antibody solution a sufficient quantity of antibody should bind to the solid phase to provide a measurable signal in the cloth immunoassay. A microporous solid phase, e.g., nylon or nitrocellulose membranes, as in the prior art, is not suitable for such an assay since the instanteous reaction with antibody requires that the solid phase be quickly and easily washed (e.g., by placing on an absorbent pad and washing as described above) immediately after application of the sample. This cannot be easily accomplished using microporous materials. Because of the microporosity, the rate of diffusion at the sample to the surface is limited by the small size of the pores through which the sample molecules must traverse to react with the solid phase. Furthermore, the amount of antibody bound (or extent of immunoreaction) under such circumstances will be directly proportional to the concentration of antibody present initially in the solution, because of an inherent property of macroporous cloth.

Some of the uses of the cloth enzyme immunoassay device and method of the present invention include the serological diagnosis of infectious diseases in humans and animals, and the rapid screening of hybridoma cultures for the identification of desired specific monoclonal antibodies. As a diagnostic tool, the cloth enzyme immunoassay of the present invention, is also ideally suited for "field" tests, where small numbers of samples (e.g., a few dozen) must be assayed. This may preferably be accomplished by using a "dipstick" format where a small (e.g., 6×6 mm) segment of antigen-coated polyester cloth is fixed to a strip of inert material providing a convenient means of handling the latter, or by using a large sheet of antigen-coated polyester cloth capable of accommodating multiple samples, which can be spotted on, to give a qualitative test. This latter approach is also believed to be ideal for the screening of large numbers of hybridomas for specific monoclonal antibodies.

The advantages of the cloth enzyme immunoassay method of this invention, for measuring antibodies in test samples include the following: (1) since this is a method based on the kinetics of the antigen-antibody reaction, quantitation is theoretically more accurate than the conventional methods, which rely on measuring immunoreactions at equilibrium; (2) because of the short exposure of the antigen-cloth to the test sample, only highly specific antibodies should bind significantly, giving a more reliable test result since non-specific reactions will be minimized and thus false-positive reactions are less likely; and (3) the total time required to complete the assay is considerably shorter than that using conventional methods, which rely on lengthy incubations. This embodiment of the present invention required only 30 min to complete a test, whereas the conventional (microtiter plate) method required a minimum of 90 min. The time required to complete such a cloth enzyme immunoassay test can be further shortened to under 15 min by using a TMB substrate system which is more sensitive, instead of the ABTS system.

An enzyme immunoassay based on the initial rate of immunoreaction is provided by another embodiment of this invention using a Salmonella antigen-antibody system. Salmonella lipopolysaccharide-coated polyester cloth is instantaneously exposed to goat anti-Salmonella antibody standards and the captured antibody is assayed colourimetrically using an anti-goat antibody-peroxidase conjugate. The colour intensity is proportional to the antibody concentration, thus providing a rapid and quantitative assay for antibodies.

Members of the genus Salmonella, the major cause of human enteritis worldwide, are often found associated with solid or semi-solid matter (e.g., food, feces, etc.) from which they spread to human hosts. Enzyme immunoassay of Salmonella antigens in solid-rich samples, e.g., foods or feces, requires that the antigens be extracted from the sample into a solid-free liquid in order to allow for their free interaction with solid-phase-immobilized immunoreagents.

One specific embodiment of this method is for the detection of *Salmonella Typhimurium* lipopolysaccharide antigens in chicken meat. The method is, however, not limited to this system, and it is applicable to most instances where it is desirable to separate Gram-negative lipopolysacchride antigens from solid or semi-solid samples, followed by concentration and detection by cloth enzyme immunoassay.

The basis for the method is as follows: it is often necessary to detect Gram-negative pathogens (e.g., Salmonella organisms) in solid or semi-solid samples (e.g., foods e.g., chicken meat, thick broths, powders, or feces of sick humans or animals) in order to assess contamination or diagnose disease. Enzyme immunoassay is rapidly gaining popularity as a method for detecting such antigens. However, enzyme immunoassays which use antibodies immobilized on a solid phase to capture antigens present in samples as in the prior art require that the antibodies be in physical contact with these antigens. When the antigens are complexed with (or physically entrapped within) the matrix of a solid or semi-solid sample, the proper interaction of the antibodies with the antigens cannot occur. It is therefore necessary to free the antigens from the sample solids so that solid-free samples for enzyme immunoassay can be prepared. For instances where lipopolysaccharide antigens are to be detected, the present invention provides a simple and economical method for the preparation of such solid-free samples for enzyme immunoassay. The method involves heating a solid sample (e.g., chicken meat) containing the pathogen of interest (e.g., Salmonella cells) in the presence of the chelating agent ethylenediaminetetraacetate for a short period of time. Ethylenediaminetetraacetate acts by chelating divalent cations, which stabilize the lipopolysaccharide-containing outer membrane of Gram-negative bacteria, and when Gram-negative cells e.g., Salmonella are treated with ethylenediaminetetraacetate in the presence of heat (about 100° C. for about 10 min) the lipopolysaccharide of the outer membrane is extracted from the cell surface and broken down into smaller units which remain in free solution. Thus, when cells present in a solid sample are immersed in a solution of ethylenediaminetetraacetate, then heated at about 100° C. for about 10 min, the lipopolysaccharide antigens can be recovered in non-sedimentable form which can be easily separated from the sample solids by centrifugation or filtration to obtain a solid-free supernatant or filtrate. Another advantage of the ethylenediaminetetraacetate-heat treatment is that, by breaking down the lipopolysaccharide antigens into smaller units, the smaller units react much faster and more efficiently with the antibody-coated cloth, giving improved kinetics of immunoraction (faster immunoreactions) and an increased sensitivity of detection in the cloth enzyme immunoassay.

The dissociation of Salmonella antigens present in solid or semi-solid samples into non-sedimentable forms in a liquid would allow for the removal of sample solids by centrifugation. Furthermore, because of their smaller sizes the dissociated antigens obtained in the supernatant should exhibit faster immunoreactions with antibodies in the enzyme immunoassay than antigens associated with intact cells.

Another way to accelerate immunoreactions in the enzyme immunoassay would be the use of a large-surfaced adsorbent for immunoreactants. Macroporous hydrophobic synthetic polymer cloths, e.g., polyester cloth, according to the present invention, provide a much greater surface area for immunoreactions (thus, faster reaction rates) than non-porous surfaces, e.g., as microtiter plates, as in the prior art. Furthermore, macroporous hydrophobic synthetic polymer cloths exhibit better filtration characteristics than microporous membranes, e.g., nitrocellulose and nylon membranes, as in the prior art, and thus allowing for the use of antibody-coated cloths for the capture of antigens from large volumes of sample by filtration. These advantages of macroporous hydrophobic synthetic polymer cloth combined with a method for the preparation of solid-free antigen samples allows for a more rapid and simple enzyme immunoassay for Salmonella antigens in solid-rich samples.

Salmonella antigens are effectively extracted from a solid food sample into a non-sedimentable form by heating the sample in the presence of the chelating agent ethylenediaminetetraacete. The heating of Salmonella in ethylenediametetraacetate also kills many of the viable Salmonella cells present in the sample, making it safer to handle. That the extracted antigens react much faster with antibodies adsorbed onto the cloth. The antibody-coated cloth is used to concentrate dilute antigens for detection by the enzyme immunoassay. The concentration of dilute antigens present in large sample volumes increases the effective sensitivity of the cloth enzyme immunoassay.

Heating Salmonella typhimurium in ethylenediaminetetraacetate dissociates its antigens into forms that are non-sedimentable at $10,000 \times g$. The treatment causes a marked increase in the rate of immunoreaction and the sensitivity in an enzyme immunoassay for the detection of Salmonella antigens. The method permits the extraction of Salmonella antigens from solid-rich samples and the preparation of solid-free samples by means of centrifugation. When the level of the antigens in the supernatant is too low for the immunoassay, the antigens are readily concentrated by passing a large volume of the supernatant through a macroporous hydrophobic cloth coated with anti-Salmonella antibody. Using this method, the detection of as few as 10 Salmonella cells per gram of chicken meat was possible within a total of about 18 h, which included about 16 h of enrichment in either tetrathionate, selenite cystine, or nutrient broths, all such broths being supplied by Difco.

The ability to produce solid-free samples by this method has a further important consequence: a large volume of solid-free sample containing a dilute antigen can be filtered through antibody-coated macroporous polyester cloth, which allows concentration of the antigens on the cloth for improved detectability by subsequent cloth enzyme immunoassay. This is especially important when antigen present in a liquid sample is too dilute to be detected by incubation of a limited volume of sample with the antibody-coated solid phase. The ability to concentrate all of the antigen present in such a sample on antibody-coated cloth allows for the capture of more antigen from the total sample than by simply incubating with a limited volume. Such concentration depends on the porosity of the antibody-coated solid phase, since for effective concentration the antigen solution must be passed through the capture surface. Concentration is therefore impossible using the conventional non-porous solid phases, e.g., microtiter plates, as in the prior art, and is difficult using microporous membranes, e.g., nylon or nitrocellulose, as in the prior art, which clog easily when large volumes of colloidal sample are filtered. On the other hand, the use of macroporous hydrophobic synthetic polymer cloth, e.g., polyester, as in the present invention, is ideal for this purpose, since cloth provides a sufficiently large surface area for efficient antigen capture and yet is of such a loose fibrous structure as to experience little difficulty with clogging (i.e., macroporous polyester cloth has exellent flow characteristics). Also, because the ethylenediaminetetraacetate-heat treatment breaks the LPS antigens down into smaller units which react faster with antibody-cloth, it is possible to pass a large volume of sample through the antibody-cloth at a reasonably fast flow rate, which is of practical importance.

The entire procedure, including lipopolysaccharide antigen extraction, concentration, and assay by cloth enzyme immunoassay is summarized below using the extraction of Salmonella lipopolysaccharide from chicken meat as an example: (1) a sample of chicken meat containing Salmonella cells is homogenized to a paste using a Waring TM blender; (2) a small volume of ethylenediaminetetraacetate solution (pH about 7.2) is added to the paste, mixed, then heated at about 100° C. for about 10 min (this treatment also kills the cells, making the sample safer to handle); (3) the sample is then centrifuged at about 100000×g for about 10 min to sediment the solids, and the solid-free supernatant is collected into a clean container by decanting; (4) the supernatant is then passed through (by gravity flow) a 1 cm diameter anti-Salmonella antibody-coated polyester cloth disc inserted at the bottom of a 1 cm diameter glass or plastic column (flow rate about 25 to about 50 ml/h; (5) the cloth disc, with captured antigen, is then washed in the column with a buffer to remove any unbound sample material; (6) the column is stoppered and a small volume of anti-Salmonella antibody conjugated to an enzyme is incubated with the cloth disc, typically for about 30 min, and the disc is again washed with buffer (as previously) to remove unbound conjugate; (7) the column is stoppered again and a chromogenic enzyme substrate is added and incubated with the cloth disc in the column to measure bound enzyme activity; (8) the substrate is recovered from the column and the colour intensity of the solution is measured using a spectrophotometer.

Some uses of the combined extraction-concentration method of the present invention include the detection of Gram-negative pathogens in foods and animal feeds (e.g., Salmonella. Campylobacter), in tissue specimens from diseased animals (e.g., detection of Brucella lipopolysaccharide antigens in lymph node specimens from cattle in autopsy), and in feces from sick humans or animals (e.g., detection of Salmonella or enteropathogenic Escherichia coli LPS antigens in human feces for the purpose of diagnosis). In cases where the number of organisms present in a sample is expected to be too low to meet the minimum level required for detection by the cloth enzyme immunoassay, it may be necessary to first amplify the organisms by enrichment in a growth medium: the sample is incubated for several hours to over night in a suitable nutrient growth medium, to allow for multiplication of the organisms, and the whole is then extracted by the ethylenediaminetetraacetate-heat method and a solid-free sample is prepared. The antigen can then be detected by concentrating the solid-free sample on antibody-cloth, followed by cloth enzyme immunoassay. The advantage of concentration is that, since it allows for the more efficient detection of dilute antigen in large volumes of sample, the time of the amplification stage by enrichment culture may be reduced since the ability to concentrate antigens eliminates the necessity of growing the cultures to high cell densities.

The present invention also provides a rapid and simple procedure which allows for both affinity purification and biotinylation of antibodies on antigen-coated macroporous polyester cloth. Macroporous polyester cloth is inexpensive, provides a large surface area for immunoreagent adsorption, and can be easily washed after immunoreaction. These advantages make antigen-coated macroporous polyesters cloth suitable as an adsorbent for the affinity purification of specific antibodies. Furthermore, biotinylation of immunoadsorbed antibodies directly on the macroporous hydrophobic synthetic polymer cloth is possible. Since the macroporous hydrophobic synthetic polymer cloth can be easily washed after reaction, its use would eliminate the need for the dialysis or gel filtration steps which are required for the preparation of biotinylated antibodies in free solution. The present invention provides, as an example, the biotinylation of anti-Salmonella antibodies from an antiserum on Salmonella lipopolysaccharide (LPS)-coated macroporous polyester cloth.

EXAMPLES

Before describing various embodiments of this invention, a description of the reagents used will be given. Chemicals used were of the analytical reagent grade. Biochemicals were purchased from Sigma Chemical Co. Distilled water ($H_2O$) was employed as a universal solvent. Antigens and bovine antisera were provided by the Animal Diseases Research Institute (ADRI) in Nepean, Ontario, Canada. Some materials employed as solid phases (i.e., cellulose cotton and macroporous nylon cloths) were acquired locally, (i.e., in the Ottawa, Canada area), whereas non-woven macroporous polypropylene filter cloth was purchased from Aldrich Chemical Co. and a variety of macroporous polyester cloths (e.g., SONTARA TM as more fully described above) were obtained from DuPont.

The following reagents were obtained from Sigma Chemical Co.: bovine serum albumin (BSA) (No. A-7030); rabbit anti-BSA serum (No. B-1520); normal rabbit serum (No. S-2632); anti-rabbit IgG antibody-horseradish peroxidase conjugate (No. A-6154); and 2,2'-azino-(3-ethylbenzthiazoline-6-sulfonic acid) (ABTS) (No. A-1888); biotinamidocaproate N-hydroxysuccinimide ester (BACHS) (No. B-2643), Salmonella typhimurium LPS (No. L-6511); p-nitrophenyl phosphate (No. 104-0); bovine serum albumin (BSA) (No. A-7888), and anti-rabbit IgG antibody-alkaline phosphatase conjugate (No. A-8025A). Streptavidin-alkaline phosphatase conjugate was obtained from Boehringer Manheim (No. 1089-616). Affinity purified polyclonal antibodies (CSA-1) to heat-killed Salmonella cells were obtained from Kirkegaard and Perry Laboratories, Inc. (No. 01-91-99), as was CSA-1 antibody-alkaline phosphatase conjugate (No. 05-91-99).

Before use, all conjugate stock solutions were diluted in 0.01M phosphate-buffered (pH 7.2)-0.85% NaCl (PBS) containing 0.05% Tween 20 TM (PBST) at the manufacturer's recommended working dilution, except for the streptavidin-alkaline phosphatase conjugate which was used at a dilution of 1:4000. Normal rabbit serum was a pre-immunization serum devoid of anti-Salmonella antibodies.

ENZYME IMMUNOASSAY REAGENTS

| (1) 0.06 M carbonate buffer (pH 9.6) | |
|---|---|
| NaHCO$_3$ | 3.8 g |
| Na$_2$CO$_3$ | 1.93 g |
| Add H$_2$O and NaOH (if necessary) to 1,000 ml. | |
| (2) 0.01 M phosphate-buffered saline (pH 7.2) | |
| (hereinafter abbreviated PBS) | |

| -continued | |
|---|---|
| NaH$_2$PO$_4$.2H$_2$O | 0.31 g |
| Na$_2$HPO$_4$ | 1.1 g |
| NaCl | 8.5 g |
| (3) PBS with TWEEN 20 TM | |
| (hereinafter abbreviated PBST) | |
| PBS | 1000 m |
| TWEEN 20 [TWEEN 20 is the registered Trade Mark of an emulsifier comprising polyoxyethylene derivatives of fatty acid partial esters of sorbitol anhydrides of Atlas Chemical Industries] | 0.5 ml |
| (4) Indicator system for horseradish peroxidase (ABTS-indicator) | |
| 0.05 M citrate buffer (pH 4.5) | 20 ml |
| 40 nM 2,2'-Azino-di-(3-ethylbenzthiazoline sulfonic acid) (hereinafter abbreviated ABTS) | 0.5 ml |
| 0.5 M H$_2$O | 0.02 ml |
| (5) Indicator system for alkaline phosphatase | |
| diethanolamine | 2.62 g |
| P-nitrophenyl phosphate | .025 g |

Add H$_2$O and HCl to 25 ml to obtain a final pH 9.8.

The following adsorbents for immunoreagents were tested: polyester non-woven cloth (DuPont, Sontara 8100); polypropylene filter (Aldrich Chemical Co., No. Z10425-6); polyethylene filter (Fisher Scientific Co., 1.5 mm thickness); cellulose cotton cloth (obtained locally); and 96-well polystyrene microtiter plates (Bion-Rad Labs, No. 224-0096).

(6) Antigens and Immunoreagents

The following were obtained from Sigma Chemical Co.: Salmonella typhimurium lipopolysaccharide (No. L-6511), S. enteritidis lipopolysaccharide (No. L-6386), *Escherichia coli* strain K-235 lipopolysaccharide (No. L-2143), *E. coli* serotype 0127:B8 lipopolysaccharide (No. L-3129), Pseudomonas aeruginosa lipopolysaccharide (No. L-9143), and rabbit anti-chicken IgG-peroxidase conjugate (No. A-9046). The conjugate was diluted 1:1000 in 0.01M phosphate-buffered (pH 7.2)-0.85% NaCl (PBS) containing 0.05% TWEEN 20 TM before use.

(7) Eggs

A total of 113 fresh eggs were tested for anti-Salmonella IgG. Of these, 71 were purchased from several independent Ottawa Valley produce retailers, 24 were purchased from two major Eastern Ontario supermarket chains, and 18 were obtained from a small (i.e., less than 40 hens) Ottawa Valley farm.

(9) Antibody Standard and Enzyme Conjugates

The antibody standard used was a commercial preparation of affinity-purified polyclonal goat antibodies (CSA-1) to heat-killed Salmonella cells (Kirdegaard and Perry Laboratories, Inc., No. 01-91-99) suspended in 0.01M phosphate-buffered (pH 7.2)-0.85% NaCl (PBS). Other immunoreagents used were an anti-goat IgG antibody-horseradish peroxidase conjugate solution (Sigma, No. A-3540) and an anti-rabbit IgG antibody-horseradish peroxidase conjugate solution (Sigma, No. A-6154). Before use, these stock solutions were diluted 1:1000 in PBS containing 0.05% TWEEN 20 TM.

(10) Bacteria

Salmonella typhimurium strain LT 2 was grown in M 63 minimal salts medium containing 0.5% glucose, at 37° C. For use in the enzyme immunoassay, the Salmonella cells were grown to 6×10$^8$ cells/ml, washed twice with 0.01M phosphate-buffered (pH 7.2)/0.85% NaCl by centrifugation at 10000×g for 10 min, 4° C., and resuspended in the original volume of PBS. The cell suspension was used in the enzyme immunoassay within a few hours of its preparation.

(11) Immunoreagents

The primary (capture) antibody used to coat the macroporous, hydrophobic cloth for enzyme immunoassay was a commercial preparation of affinity-purified polyclonal antibody (CSA-1) to heat-killed Salmonella cells (Kirgegaard and Perry Laboratories, Inc., No. 01-91-99) with a specificity for all known Salmonella serotypes.

The immunological specificity of a CSA-1 antibody-horseradish peroxidase conjugate (Kirkegaard and Perry Laboratories, Inc., No. 04-91-99) was tested, and it was found that approximately 60% of the total enzyme activity bound to purified *S. typhimurium* lipopolysaccharies. A stock of the conjugate (0.1 mg of protein per ml in PBS) was stored at −20° C. Before use, it was diluted 1:2000 in PBS containing 0.05% TWEEN 20 TM.

(12) Preparation of Affinity Purified Anti-Brucella Antibodies from Bovine Antiserum Anti-Brucella antibodies were purified from bovine antiserum by the affinity purification method. It is based on the adsorption of anti-Brucella antibodies onto the antigenic surface of whole killed *B. abortus* cells mixed with antiserum. Cells with adsorbed antibodies can then be separated from the serum by centrifugation, and the antibodies can be recovered by exposure to a low pH environment with subsequent removal of the cells by centrifugation. The method is simple to perform, inexpensive, and usually results in high yields of specific antibodies.

Ten milliliters of standard plate test antigen, consisting of whole heat-killed *B. abortus* cells (strain 413, biotype 1) suspended in phenol-saline (i.e., 0.85% NaCl and 0.5% phenol in H$_2$O) at a concentration of 4×10" cells/ml, were dispensed in a 50 ml-capacity round bottom polycarbonate centrifuge tube. The cells were pelleted by centrifugation at 10,000×g, for 10 minutes. The pellet was then washed twice in 0.1M glycine-HCl (pH 2.24) to remove any acid-soluble material present on the cell surface, followed by two washings in 0.1M Tris-HCl buffer (pH 7.0). As used herein, the abbreviation means Tris(hydroxymethyl)aminomethane Care was taken to disperse the cells as gently as possible during resuspension (a glass stirring rod is convenient for this purpose). To the final washed pellet was added 25 ml of bovine antiserum, in which the cells were dispersed. The suspension was allowed to stand at room temperature for 30–40 minutes, with gentle stirring every 5–10 minutes. The suspension was then centrifuged as above and the supernatant discarded. The resulting pellet was washed three times in 25 ml of 0.1M Tris-HCl buffer (pH 7.0) to remove any loosely adsorbed material. Brucella-specific antibody was recovered by resuspending the final washed pellet in 25 ml of 0.1M glycine-HCl (pH 2.24). The cells were immediately removed by centrifugation and antibody-rich supernatant was transferred to a vessel containing 10 ml of 1.0M Tris-HCl buffer (pH 8.0) in order to abrogate the harsh low pH environment. The remaining cell pellet was processed in this manner a second time to improve antibody recovery, and the final supernatants were pooled. The antibody solution was then dialyzed against PBS for 24 hours at 4° C., with at least three changes of buffer. Percipitate material arising in the dialysate was stored at −80° C. until use. Whenever necessary, the protein in the dialysate was concentrated using an AMICON ™ protein concentrator.

Unless otherwise specified, antiserum used in the Examples was serum obtained from chronically infected cattle which have high titers of anti-Brucella antibody. *B. abortus* cells used were heat-killed standard plate test antigen (whole cells) which is strain 413, biotype 1, suspended in phenol-saline.

(13) Preparation of Rabbit Anti-Salmonella Serum

Salmonella typhimurium strain LT 2 was grown overnight in M63 minimal salts medium. Cells were then washed twice with PBS containing 50 mM EDTA (pH 7.2) to a density of $10^9$ cells/ml. As used herein, the abbreviation EDTA means ethylenediaminetetraacetate. The suspension was then autoclaved at 121° C. for 20 min, cooled to room temperature, and dialysed extensively against PBS at 4° C. This antigen suspension was stored at 4° C.

For immunization, one male New Zealand White rabbit (3 months old) was inoculated intravenously with 0.5 ml of the antigen suspension (day 1). After 20 days, the rabbit received a second 0.5 ml injection of the suspension. Serum samples were prepared from bleedings done on days 1 and 20 (prior to the inocuulations) and at 10-day intervals thereafter.

(14) Preparation of an Enzyme-antibody Conjugate by the Periodate Oxidation Method A modified version of the method developed by Nakane and Kawaoi was employed for conjugating horseradish peroxidase with anti-Brucella antibody. For this, highly purified horseradish peroxidase (RZ=3) was used, where RZ is the light absorbance ratio of $A_{403}/A_{275}$ for a given enzyme solution. Five milligrams of horseradish peroxidase (Sigma, type VI, RZ=3.0) were dissolved in a mixture of 1.0 ml of 0.3M sodium carbonate (pH 8.1) and 1.0 ml of 0.08M $NaIO_4$. The solution was mixed gently for 30 minutes at room temperature, and 1.0 ml of 0.16M ethylene glycol was then added. This was further mixed at room temperature for 1 hour. The latter solution was then dialyzed against 5 l of 0.01M sodium carbonate buffer (pH 9.5) at 4° C. for 16–24 hours. To this dialysate was added 0.5 ml of PBS containing ca. 5 mg of affinity purified anti-Brucella antibody and 0.5 ml of 1.01M carbonate buffer (pH 9.5). The solution was incubated for 3 hours at room temperature, with gentle mixing. At the end of the incubation, 5 mg of $NaBH_4$ were added to the solution which was then left to stand at 4° C. for 3 hours. The solution was then dialyzed extensively against PBS at 4° C. Any precipitable material formed in the dialysate was removed by centrifuging for 10 minutes in an eppendorf microfuge. The resulting supernatant constituted the stock conjugate, which was designated conjugate, and was stored at −20° C. until use.

(15) Collection of Antiserum

An adult cow suffering from chronic brucellosis was bled at one-week intervals over a period of approximately three weeks. At each bleeding, 1 l of blood was collected in glass bottles and immediately incubated at 37° for 2 hours, followed by overnight storage at 4° C. to allow for complete clot formation. The serous liquid was decanted into separate vessel and centrifuged at 8,000×g to remove any remaining blood cells. The supernatant thus obtained was stored at −20° C.

A large stock of antiserum, which was used as a source of antibody for all subsequent experiments, was prepared by pooling all serum samples obtained after the prescribed succession of bleedings, and was stored at −80° C. until use.

(16) Preparation of LPS-Coated Macroporous Polyester Cloth

Polyester cloth (DuPont, SONTARA 8100 TM) was cut into 6 mm square segments. Before coating, S. typhimurium lipopolysaccharide was dissolved in PBS containing 0.05M EDTA (pH 7.2)-(EDTA-PBS) and was then heated at 100° C. for 10 min. For use in affinity purification, 10 polyester cloth segments were incubated with 1 ml of the lipopolysaccharide solution (100 μg/ml) for 16 h at room temperature, then washed with PBST on a macroporous filter under suction. For use in enzyme immunoassay, each macroporous polyester cloth segment was incubated as above with 50 μl of EDTA-heat-treated lipopolysaccharide solution (10 μg/ml) in a closed petri dish, and then washed with PBST. The lipopolysaccharide-cloths were stored at 4° C. in PBS.

5) BRIEF DESCRIPTION OF THE DRAWINGS

In the accompanying drawings,

FIG. 1 is a graph showing the effect of varying the treating affinity purified antibody concentration on the signal generated in the polypropylene cloth-based cloth enzyme immunoassay;

FIG. 2 is a graph showing the partial denaturation of bovine antiserum antibodies by acidification;

FIG. 3 is a graph showing the partial denaturation of bovine antiserum and affinity purified antibodies by heat; and FIG. 4 is a graph showing diluted antiserum as a source of coating antibody.

FIG. 5 is a graph showing the comparison of the enzyme immunoassay with a polyester cloth and a microtiter plate where $A_{414}$ is shown as the ordinate and log dilution of the serum is shown as the abscissa;

FIGS. 6A and 6B are graphs showing the effect of incubation times on the enzyme immunoassay where $A_{414}$ is shown as the ordinate, and incubation (in minutes) as the abscissa;

FIG. 7 is a graph showing the detection of egg yolk A IgG to various Salmonella lipopolysaccharide showing $A_{414}$ as ordinate and dilution as abscissa;

FIG. 8 is a graph showing the measurement of anti-Salmonella antibody by initial rate of immunoreaction with $A_{414}$ is ordinate and concentration of antibody (in μg/ml) as abscissa;

FIG. 9 is a graph showing the assay of anti-Salmonella antibody in rabbit serum with $A_{414}$ as ordinate and time (in days) as abscissa;

FIG. 10 is a graph showing the effect of heating Salmonella cells in various concentrations of ethylenediaminetetraacetate on the cloth enzyme immunoassay signal with $A_{414}$ as ordinate and concentration (in Molar of ethylenediaminetetraacetate) as abscissa;

FIG. 11 is a graph showing the kinetics of the antibody-antigen reaction of ethylenediaminetetraacetate-heat-treated and untreated Salmonella samples, with $A_{414}$ as ordinate and time (in minutes) as abscissa;

FIG. 12 is a graph shown in the extraction of Salmonella antigents from chicken meat by ethylenediaminetetraacetate-heat treatment with $A_{414}$ as ordinate and concentration (in Molar) of ethylenediaminetetraacetate as abscissa;

FIG. 13 is a graph showing the concentration of dissociated Salmonella antigens onto antibody-coated cloth with $A_{414}$ as ordinate and log (cells/g) as abscissa; and FIG. 14 is a graph of recovery of total proteins from LPS-cloth with protein (in μg) as ordinate and dilution as abscissa;

FIG. 15 is a graph of recovery of anti-Salmonella antibody titer in affinity purification, with recovery (in %) as ordinate and dilution as abscissa;

FIG. 16 is a composite graph of the conditions for the biotinylation of immunoadsorbed antibodies in which graph is drawn with $A_{404}$ as ordinate and pH as abscissa, in which graph is drawn with $A_{404}$ as ordinate and mg/ml as abscissa, and in which graph is drawn with $A_{404}$ as ordinate and time (hrs) as abscissa; and FIG. 17 is a graph of cloth enzyme immunoassay of Salmonella antigens with $A_{404}$ as ordinate and log (cells/ml) as abscissa.

DESCRIPTION OF PREFERRED EMBODIMENTS

The following are Examples of this invention:

Experiments have been carried out on the use of antigen or antibody coated macroporous polyester cloth for the rapid enzyme immunoassay assay of specific antibodies or antigens.

I (a) Determination of the Optimum Affinity Purified Coating Antibody Concentration for the Polypropylene-based Cloth Enzyme Immunoassay of Brucella Antigens Macroporous polypropylene filter cloth pieces (6×6 mm) were coated with 50 μl of various concentrations of affinity purified anti-Brucella antibody per piece (a concentration range of 0.2 to 1.0 mg of protein/ml was chosen). After the required overnight incubation period, the cloths were washed with PBST and subsequently incubated with 30 μl of B. abortus cells (strain 413, biotype 1) diluted to $4 \times 10^8$ cells/ml in PBS, for 30 minutes at room temperature. A series of negative control cloths (incubated without antigen) was also included. The cloths were then washed with PBST and probed with 25 μl of conjugate diluted 1:1,000 in PBST, and incubated for 30 minutes at room temperature. After washing with PBST, the cloths were assayed for retained horseradish peroxidase activity by immersion in 0.5 ml of ABTS-indicator solution for 30 minutes, at room temperature, and the reaction was stopped by addition of 0.5 ml of 0.1M NaF. Absorbance was read at 650 nm.

Figure 1:
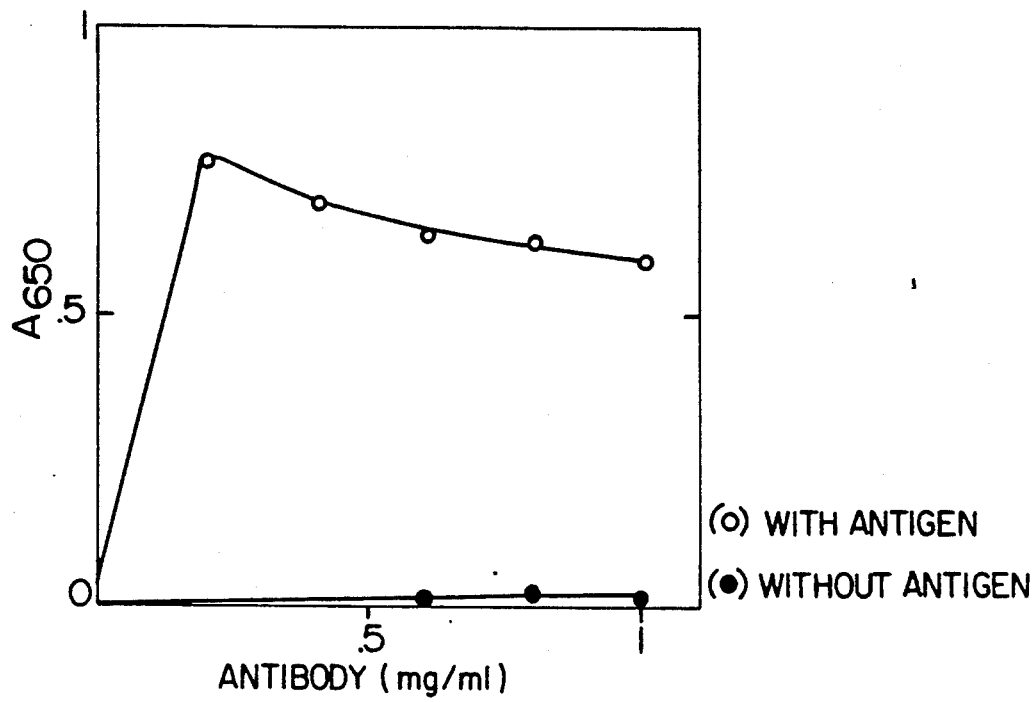

As shown in FIG. 1, the assay response peaks at a concentration of 0.2 mg/ml.

II(b) Pretreatment (Partial Denaturation) of the Coating Antibody

The use of antiserum for the direct coating of the cloth was investigated as an effective and economical alternative to purified antibody.

In order to achieve maximum immobilization of the antibodies present in the antiserum, a simple procedure was developed for the pretreatment of the coating antiserum to incur partial denaturation of the antibodies, thus rendering them more capable of interacting with the hydrophobic cloth surface, to the exclusion of other serum proteins which might compete for binding sites on the cloth. In order to improve the detectability of the cloth enzyme immunoassay employing bovine antiserum as the source of coating antibody, partial denaturation procedures were developed using an acidic pH and heat. The following describes an investigation undertaken to determine the optimum time of exposure to a pH 2.5 environment for the improved immobilization of antibodies from antiserum on polypropylene.

Three separate 0.85 ml aliquots of antiserum were mixed with 0.3 ml each of 0.4M glycine-HCl buffer (pH 1.5) to produce a final pH 2.5. A zero-time exposure sample consisting of 0.85 ml of antiserum plus 0.6 ml of 1.0M Tris-HCl buffer (pH 7.0) was also prepared as a control. Each acidified sample was allowed to stand at room temperature for either 5, 10, or 20 minutes, after which they were immediately neutralized by addition of 0.3 ml of 1.0M Tris-HCl (pH 8.0). These samples were then used to coat macroporous polypropylene filter cloth pieces. The effect of time of exposure to pH 2.5 on the signal generated is presented in FIG. 2.

Figure 2:
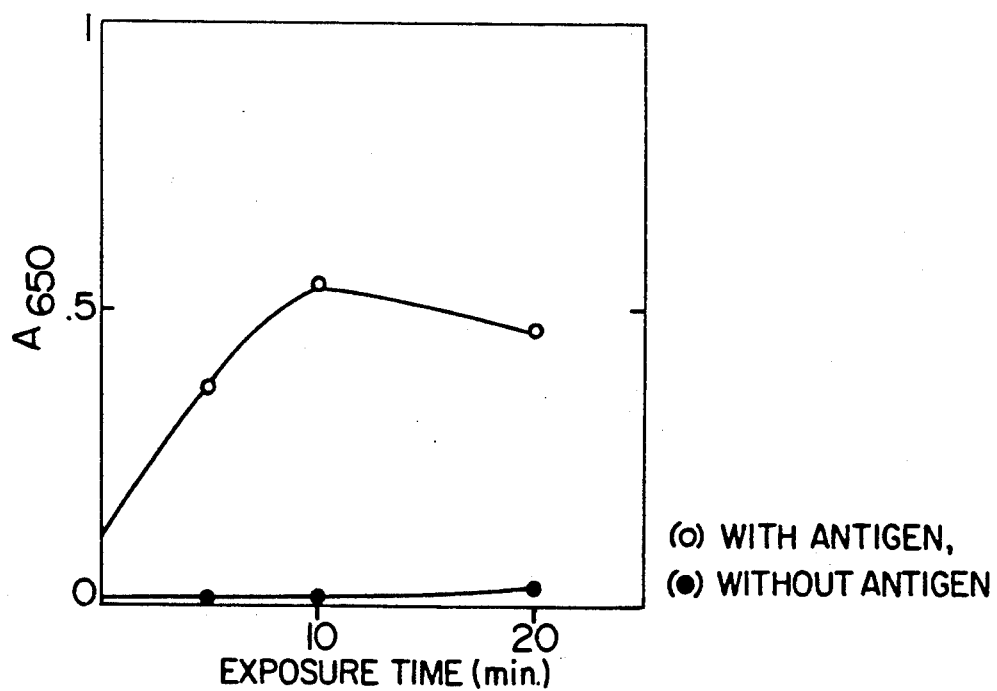

FIG. 2 shows that an approximate five-fold improvement in the assay's sensitivity was achieved by exposure of the antiserum to pH 2.5 for 10 minutes.

In a second experiment, the effect of exposing bovine antiserum and affinity purified antibodies to heat on their abilities to serve as sources of coating antibodies was examined. One milliliter samples of antiserum and the affinity purified antibody dialysate (containing 0.27 mg of protein/ml) were incubated for 10 minutes at either 25°, 65°, 70°, 75°, or 80° C.

These were then allowed to cool to room temperature and used to coat macroporous polypropylene cloths as previously. The assay protocol employed was the same as in the previous experiment, with the exception that the antibody-coated cloths were incubated with 30 μl of B. abortus plate test antigen diluted to $4 \times 10^7$ cells/ml in PBS. The results of this experiment are presented in FIG. 3, where the signal generated in the cloth enzyme immunoassay is plotted against temperature for both antiserum and affinity-purified antibody.

Figure 3:
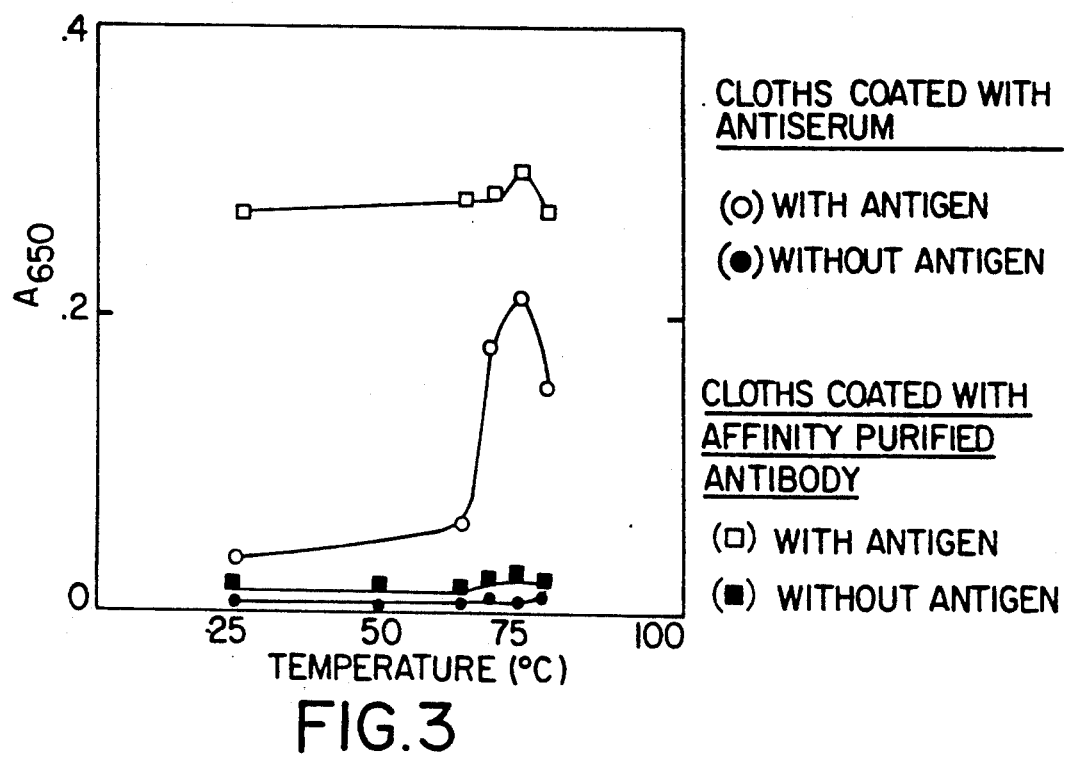

FIG. 3 shows that an even greater improvement in sensitivity was obtained by heating the serum at 75° C. for 10 minutes. The sensitivity of the assay employing affinity purified antibody remained essentially unchanged over the range of temperatures tested.

These experiments have demonstrated the usefulness of either exposure to a low pH or heat in improving the sensitivity of the assay using antiserum as the source of coating antibody.

Without wishing to be bound by theory, it is believed that the improvement in the sensitivity of the antiserum-based immunoassay is a consequence of an increase in the hydrophobicity of the denatured Fc region of the antibodies, which in turn causes these to be adsorbed more strongly to the macroporous hydrophobic synthetic polymer cloth surface and in greater numbers. The partially denatured state may also ensure that the antibodies adhere to the solid phase in a more ideal orientation, with the Fc region affixed to the macroporous hydrophobic synthetic polymer cloth surface and the Fab segments free to interact with the antigen. Treating the antibodies affinity-purified with heat did not seem to confer any particular advantage. Thus, these affinity-purified antibodies cannot be beneficially altered further by heat treatment.

II(c) Diluted Bovine Antiserum as a Source of Coating Antibody

The feasibility of applying diluted antiserum in the cloth enzyme immunoassay was investigated in the following experiment.

Aliquots of bovine antiserum were diluted 2, 4, 6, 8, and 10 times in PBS. The diluted samples were partially denatured by heating at 75° C. for 10 minutes. These were then cooled to room temperature and applied to 6×6 mm macroporous polypropylene filter cloth pieces, which were subsequently employed in the cloth enzyme immunoassay according to the procedure used in the previous example. The results are presented in FIG. 4, where the cloth enzyme immunoassay signal generated is plotted against the serum dilution factor.

Figure 4:
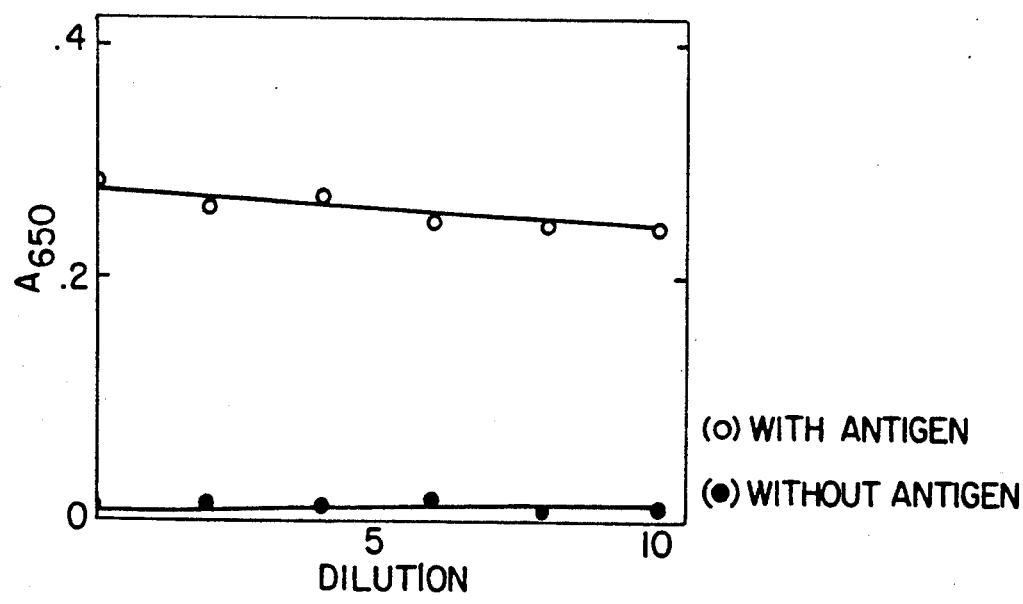

FIG. 4 shows that there was no appreciable decline in the sensitivity of the assay throughout the range of coating serum dilutions examined. Therefore, it was concluded that bovine antiserum diluted 1:10 in PBS, with subsequent heating at 75° C. for 10 minutes, can serve as a suitable source of coating antibody in the cloth enzyme immunoassay. The precise dilution factor used for a given batch of antiserum will, of course, depend on the specific antibody titer of that serum.

II(d) Detectability of the Cloth Enzyme Immunoassay For Brucella Antigens

The detectability of Brucella cells and lipopolysaccharide antigens by the polypropylene cloth enzyme immunoassay was examined in this Example. Unless otherwise stated, all antibody coated cloths used in the following experiments were prepared with bovine antiserum diluted 1:10 in PBS and heated at 75° C. for 10 minutes.

II(e) Detectability of the Whole Cell Assay Employing Antibody-Coated Polypropylene Filter cloth Antibody-coated macroporous polypropylene filter cloth pieces were incubated for 30 minutes at room temperature with 30 μl of B. abortus cell suspensions containing either $1.2\times10^5$, $1.2\times10^4$, or $1.2\times10^3$, cells in PBS. Each cloth in this series of experiments was prepared in quadruplicate, as were cloths to which 30 μl of PBS containing no antigen was added. These were then washed with PBST and probed with 25 μl of conjugate diluted 1:1000 in PBST, for 30 minutes at room temperature. At the end of this period, the cloths were washed with PBST and assayed for retained horseradish peroxidase by immersion in ABTS-indicator solution for 3 hours, in order to optimize the final enzyme signal. The enzyme reaction was stopped by addition of 0.5 ml of 0.1M NaF. Table 1 shows the relationship between the quantity of antigen added and the corresponding cloth enzyme immunoassay signal obtained.

TABLE 1

| Detectability of the Whole Cell Assaay Employing Antibody-Coated Macroporous Polypropylene Filter Cloth | | | | |
|---|---|---|---|---|
| No. of Cells Applied | $A_{650}$ | | | |
| Per Cloth | 1 | 2 | 3 | 4 |
| $1.2\times10^5$ | 0.186 | 0.213 | 0.234 | 0.245 |
| $1.2\times10^4$ | 0.107 | 0.080 | 0.106 | 0.075 |
| $1.2\times10^3$ | 0.054 | 0.050 | 0.060 | 0.055 |
| 0 | 0.060 | 0.051 | 0.058 | 0.055 |

When used herein in any table hereinafter, the abbreviation LPS means lipopolysaccharide.

Table 1 shows that the polypropylene cloth immunoassay can detect $10^4$ cells using a 36 mm² macroporous polypropylene cloth.

II(f) Detectability of Brucella Lipopolysaccharide by the Polypropylene Cloth Immunoassay The assay procedure employed for the detection of whole cells using antibody-coated macroporous polypropylene filter cloth was applied to the detection of B. abortus lipopolysaccharide. In this Example, antibody-coated cloths were incubated for 30 minutes at room temperature with 30 μl of PBS containing either 3, 0.3, or 0.03 ng of lipopolysaccharide, or PBS alone. Each cloth was prepared in quadruplicate. These were then processed in the immunoassay as previously described. The results are presented in Table 2.

TABLE 2

| Detectability of Lipopolysaccharide by Macroporous Polypropylene Cloth Immunoassay | | | | |
|---|---|---|---|---|
| LPS Applied | $A_{650}$ | | | |
| per Cloth (ng) | 1 | 2 | 3 | 4 |
| 3.00 | 1.350 | 1.302 | 1.440 | 1.100 |
| 0.30 | 0.261 | 0.225 | 0.216 | 0.230 |
| 0.03 | 0.063 | 0.058 | 0.066 | 0.068 |
| 0 | 0.068 | 0.040 | 0.043 | 0.056 |

Table 2 shows that the detectability of this assay occurred at approximately 0.3 ng (or 300 picograms) of lipopolysaccharide applied per cloth piece.

II(g) Performance of the Immunoassay Under Simulated Clinical Conditions

In the routine diagnosis of brucellosis, Brucella organisms are often recovered from infected animals in milk; vaginal secretions; supramammary, retropharyngeal, internal iliac, and lumbar lymph nodes; spleen tissue; uterine tissue; and in some instances, blood. As these materials constitute complex environments for the detection of antigens, it was determined whether or not undefined sample components might be prohibitive to antigen detection by the immunoassay. Another aspect of clinical specimens examined was the interference of anti-Brucella antibodies present in the samples to the antigen assay by the immunoassay. The ability of the macroporous polypropylene filter cloth-based assay to detect B. abortus antigens in body fluids and tissue homogenates of bovine origin was examined in Example II. Anti-body-coated cloth was prepared as in the previous Example.

II(h) Detection of B. Abortus in Bovine Body Fluids and Tissue Homogenates

In order to ascertain the ability of the immunoassay to detect B. abortus antigens in simulated clinical specimens, tissues obtained from a cow which was a serological reactor for B. abortus, but culture negative, were artifically innoculated with whole cells and assayed for the presence of antigen as described below. The presence of endogenous circulating antibody specific for B. abortus offered an opportunity to assess the performance of the assay under conditions which might theoretically interfere with the capture of antigen in such samples. The possible inhibitory effect of endogenous antibody was alleviated by subjecting the test samples to extreme heat (3 hours, 70° C.) prior to performing the assay.

Tissue homogenates were prepared by homogenizing in a stomacher and adding sufficient PBS to produce a fluid consistency (approximately 0.5 ml per gram of tissue). Homogenates were made from the following bovine tissues; inguinal lymph nodes, spleen, and uterine horn.

A sample from each homogenate was inoculated with sufficient B. abortus cells to give a final concentration of $8\times10^5$ cells/ml. Milk and serum samples from a healthy animal were likewise inoculated. These samples, along with their uninoculated counterparts, were heated at 70° C. for 3 hours, after which they were cooled to room temperature. Antibody-coated macroporous polypropylene filter cloths were then added to triplicate test tubes containing 0.5 ml of heated sample (one cloth/tube) and incubated for 30 minutes at room temperature with constant gentle shaking. The cloths were then removed and processed in the immunoassay as previously described. Macroporous hydrophoshic synthetic polymer cloths were assayed for retained conjugate by immersion in 0.5 ml of ABTS-indicator solution for 30 minutes. The results are shown below in Table 3.

TABLE 3

Detection of Antigens Suspended in Body Fluids and Tissue Homogenates.

| | $A_{650}$ | | | | | |
|---|---|---|---|---|---|---|
| | Specific[b] | | | Control[c] | | |
| Sample[a] | 1 | 2 | 3 | 1 | 2 | 3 |
| A | 0.185 | 0.240 | 0.224 | 0.070 | 0.090 | 0.083 |
| B | 0.164 | 0.177 | 0.170 | 0.057 | 0.060 | 0.061 |
| C | 0.132 | 0.170 | 0.162 | 0.022 | 0.027 | 0.020 |
| D | 0.159 | 0.165 | 0.162 | 0.020 | 0.030 | 0.020 |
| E | 0.175 | 0.192 | 0.195 | 0.045 | 0.042 | 0.040 |

[a]Tissue homogenates from spleen (A), inguinal lymph nodes (B), unterine hore (C), plus, normal bovine serum (D) and normal bovine milk (E).
[b]Macroporous hydrophobic synthetic polymer cloths incubated with inoculated samples.
[c]Macroporous hydrophobic synthetic polymer cloths incubated with uninoculated samples.

Table 3 demonstrates the assay response for each sample tested. In most cases, the control signals (i.e., those obtained from the uninoculated samples) remained low, whereas those arising from the corresponding inoculated samples were distinct. The experiment demonstrates the ability of the cloth enzyme immunoassay to detect *B. abortus* antigens suspended in various biological samples.

III(a) Detection of Bovine Viral Diarrhea Antigen

The applicability of the ability of the immunoassay to detect antigens of bacterial origin to the detection of viral antigens will now be described in this Example. When used herein, the abbreviation BVD means Bovine Viral Diarrhea.

Bovine viral diarrhea is an enteric disease posing a serious threat to exposed livestock. The etiological agent is a virus which is referred to as bovine viral diarrhea (BVD) antigen. At present, the immunoassay method is not used for the detection of BVD antigen in clinical specimens.

The strategy employed for the BVD assay was similar to that used previously for the detection of Brucella antigens: macroporous polypropylene filter cloth was coated with anti-BVD antibodies and subsequently incubated with BVD antigen, and the captured material was detected by probing with an enzyme-antibody conjugate (prepared by coupling antibodies from anti-BVD antiserum to horseradish peroxidase by the periodate oxidation method). Whole antiserum was employed in order to make the required conjugate. The feasibility of using whole antiserum for this purpose was first tested by conjugating whole anti-Brucella antiserum with horseradish peroxidase and applying the resulting conjugate in the *B. abortus* cloth enzyme immunoassay, thus affording an opportunity to compare the performance of such a conjugate with an established system.

III(b) Synthesis and Testing of a Brucella-specific Enzyme-Antibody Conjugate Made With Whole Bovine Antiserum Whole bovine anti-Brucella antiserum was conjugated to horseradish peroxidase according to the periodate oxidation method: 0.5 ml of whole serum was dialyzed overnight at 4° C. against 0.01M sodium carbonate buffer (pH 9.5). The resulting dialysate was mixed with 5 mg of periodate-activated horseradish peroxidase and incubated for 2.5 hours at room temperature. Sodium borohydride ($NaBH_4$) was then added as prescribed, and incubated for 3 hours at 4° C. against PBS, and the final dialysate was microfuged (10 minutes, at 4° C.). The cleared dialysate constituted the conjugate stock.

The performance of this conjugate in the immunoassay was compared to that of the conjugate prepared with purified antibody. Two series of Brucella-specific antibody-coated macroporous polypropylene filter cloth pieces were incubated with 30 μl of *B. abortus* cells diluted to $4\times10^6$, $4\times10^7$, or $4\times10^6$ cells/ml in PBS, for 30 minutes at room temperature. The cloths were then washed in PBST, and one series was probed with 25 μl of the conjugate prepared with affinity purified antibody diluted 1:100 in PBST while the other series was probed with 25 μl of the conjugate prepared with whole antiserum diluted 1:100 in PBST. These were incubated for 30 minutes, at room temperature, and subsequently washed with PBST. The cloths were assayed by immersion in 0.5 ml of ABTS-indicator solution for 30 min. The results are shown below in Table 4.

TABLE 4

Relative Performance of Conjugate D in the Immunoassay.

| | $A_{650}$ | | | |
|---|---|---|---|---|
| No. of Cells Applied | conjugate[1]* | | conjugate [2]** | |
| per Cloth | 1 | 2 | 1 | 2 |
| $1.2\times10^7$ | 0.852 | 0.932 | 0.631 | 0.598 |
| $1.2\times10^6$ | 0.385 | 0.400 | 0.153 | 0.180 |
| $1.2\times10^5$ | 0.081 | 0.092 | 0.081 | 0.080 |
| 0 | 0.010 | 0.012 | 0.070 | 0.075 |

*prepared by coupling affinity purified antibody to HRP
**prepared by coupling whole antiserum to HRP According to Table 4, the response of the immunoassay using conjugate[2] was somewhat dampened throughout the series of antigen dilutions tested, as compared to the performance of conjugate[1] in the assay. However, the Example demonstrates the feasibility of employing such a conjugate.

III(c) Adapted Immunoassay for the Detection of BVD Antigen

A BVD-specific conjugate was prepared by coupling whole anti-BVD antiserum to horseradish peroxidase, in order to adapt the immunoassay for the direct detection of BVD antigen.

A sample of anti-BVD antiserum (precise titer unknown) was obtained from a cow vaccinated wtih killed BVD virus. An anti-BVD serum protein-horseradish peroxidase conjugate was prepared by coupling 0.5 ml of anti-BVD antiserum dialyzed against sodium carbonate buffer to 5 mg of horseradish peroxidase as in the previous Example. The resulting product was designated conjugate.

The standard antigen employed in the immunoassay originated from a commercial BVD vaccine, consisting of killed whole virus suspended in saline containing an unknown quantity of bovine serum albumin (added as a stabilizer) and a variety of antimicrobial agents. The quantity of viral antigen per unit volume of the vaccine was not disclosed by the manufacturer. The vaccine was dialyzed overnight at 4° C. against PBS prior to use.

Macroporous polypropylene filter cloth pieces were coated with 60 μl of partially denatured anti-BVD antiserum (i.e., heated at 75° C. for 10 minutes) and incubated at room temperature as previously. Antibodycoated such cloths were incubated for 30 minutes at room temperature with 30 μl of dialyzed BVD vaccine diluted either 1:10, 1:100 or 1:1,000 in PBS. Undiluted vaccine and PBS alone were also included in the series, and each such cloth was prepared in quadruplicate. After such incubation period, the cloths were washed with PBST and probed with 25 μl of conjugate[3] diluted 1:100 in PBST, as previously. These were then assayed by immersion in 0.5 ml of ABTS-indicator solution for 30 minutes. The results are shown below in Table 5.

TABLE 5

Detection of BVD Antigen by the Immunoassay

| Antigen Dilution | $A_{650}$ | | | |
|---|---|---|---|---|
| | 1 | 2 | 3 | 4 |
| undiluted | 1.230 | 1.190 | 1.090 | 1.200 |
| 1:10 | 0.246 | 0.280 | 0.265 | 0.210 |
| 1:100 | 0.091 | 0.110 | 0.115 | 0.095 |
| 1:1000 | 0.060 | 0.071 | 0.055 | 0.050 |
| no antigen | 0.055 | 0.053 | 0.051 | 0.042 |

Table 5 shows that the detectability of the BVD assay, in the form tested, was fixed somewhere in the range of 1:10 to 1:100 dilution of the dialyzed vaccine. These results clearly demonstrate the ability of the immunoassay to detect BVD antigen.

III(d) Alternative Solid Phases for Use in the Immunoassay

A series of Examples was carried out to determine the usefulness of other materials as solid phases for capture and detection of *B. abortus* cells.

Macroporous polypropylene filter cloth was compared to a variety of other materials employed as solid phases in the immunoassay. The materials tested were 100% macroporous nylon cloth (acquired locally, i.e., in the Ottawa, Canada area), woven macroporous polyester cloth acquired locally, i.e., in the Ottawa, Canada area), nonwoven macroporous polyester cloth (SONTARA TM Dupont), cellulose acetate membrane (Gelman), cellulose nitrate membrane (Schleicher and Schuell), analytical paper (Schleicher and Schuell), and a macroporous polyethylene filter (1.5 mm thickness). These were all cut into 6×6 mm square pieces, and coated with 60 μl of partially denatured bovine anti-Brucella antiserum diluted 1:10 in PBS, as previously described. The materials were then incubated with 30 μl of *B. abortus* cells diluted to $4\times10^7$ cells/ml in PBS for 30 minutes at room temperature. A parallel series to which PBS containing no antigen was added was also included, and each solid phase was prepared in duplicate. After the incubation period, the materials were washed with PBST and probed with conjugate (prepared with affinity purified antibody) as usual. These were then assayed by immersion in 0.5 ml of ABTS-indicator solution for 30 minutes. The performance of each solid phase in the assay is shown below in Table 6.

TABLE 6

Performances of Various Solid Phases Employed in the Immunoassay

| Solid Phase | $A_{650}$ specific[a] 1 | specific[a] 2 | control[b] 1 | control[b] 2 |
|---|---|---|---|---|
| Polypropylene filter cloth | 0.428 | 0.430 | 0.012 | 0.010 |
| Nylon cloth | 0.320 | 0.338 | 0.011 | 0.009 |
| Woven polyester cloth | 0.840 | 0.860 | 0.035 | 0.026 |
| Nonwoven polyester cloth[c] | 0.810 | 0.792 | 0.033 | 0.020 |
| Cellulose acetate membrane | 0.220 | 0.186 | 0.100 | 0.122 |

TABLE 6-continued

Performances of Various Solid Phases Employed in the Immunoassay

| Solid Phase | $A_{650}$ specific[a] 1 | specific[a] 2 | control[b] 1 | control[b] 2 |
|---|---|---|---|---|
| Cellulose nitrate membrane | 0.282 | 0.235 | 0.185 | 0.192 |
| Polyethylene filter | 0.450 | 0.455 | 0.061 | 0.072 |
| Analytical paper | 0.416 | 0.422 | 0.400 | 0.421 |

[a]Cloths incubated with antigen
[b]Cloths incubated without antigen
[c]A variety of DuPont polyester cloths were examined and the results with these cloths were similar to data shown here Table 6 shows that of the solid phases tested, the highest signals were obtained with the woven macroporous polyester and nonwoven macroporous polyester cloths. Other materials that are useful in the immunoassay are macroporous nylon cloth and the macroporous polyethylene filter, which produce similar results to those obtained using macroporous polypropylene filter cloth.

The main advantage of macroporous hydrophobic synthetic polymer cloths as supports in immunoassay is that they provide a large volume for adsorption per surface area for antigen-antibody interaction. Macroporous polyethylene, macroporous nylon, and macroporous polyester cloths, by virtue of their hydrophobic characteristics, have been found to adsorb and absorb antibodies and thus provided a large surface area for antigen capture. Other materials amenable to the cloth enzyme immunoassay concept should have included cellulose acetate and cellulose nitrate membranes and filter paper. However as the results above indicated, they are not useful according to aspects of the present invention.

IV(a) Comparison of the Immunoassay Using Polypropylene Filter Cloth, a Flat Polypropylene Sheet and a Polystyrene Microtiter Plate Surface The immunoassay response arising from the use of an antibody-coated plastic polypropylene sheet and a polystyrene microtiter surface, which have very limited surface areas available for antibody adsorption, and hence antigen capture, to the assay response obtained using polypropylene filter cloth when various quantities of antigen are applied was compared.

A flat polypropylene sheet, cut into 6×6 mm pieces, was coated with anti-Brucella antibodies as were 6×6 mm pieces of polypropylene filter cloth. Several wells in a polystyrene microtiter plate were also coated. These were then incubated with 30 μl of PBS containing either $1.2\times10^7$, $1.2\times10^6$, $1.2\times10^5$, $1.2\times10^4$, *B. abortus* cells (plate test antigen), or PBS alone, for 30 minutes at room temperature. The materials were subsequently processed in the immunoassay as in the previous Example, with the exception that enzyme activity was assayed by immersion in 0.5 ml of ABTS-indicator solution for 3 hours. Each determination was done in triplicate, and the results are shown below in Table 7.

TABLE 7

Detectability of the Immunoassay Employing Three Different Solid Phases.

| $A_{650}$ | | No. of Cells Applied Per Piece $1.2\times10^7$ | $1.2\times10^6$ | $1.2\times10^5$ | $1.2\times10^4$ | 0 |
|---|---|---|---|---|---|---|
| Polypropylene | 1 | 5.02 | 1.02 | 0.29 | 0.09 | 0.04 |
| Filter | 2 | 5.12 | 1.24 | 0.29 | 0.08 | 0.03 |
| Cloth | 3 | 5.30 | 1.15 | 0.24 | 0.08 | 0.03 |

TABLE 7-continued Detectability of the Immunoassay Employing Three Different Solid Phases.

| $A_{650}$ | | No. of Cells Applied Per Piece | | | | |
|---|---|---|---|---|---|---|
| | | $1.2 \times 10^7$ | $1.2 \times 10^6$ | $1.2 \times 10^5$ | $1.2 \times 10^4$ | 0 |
| Plastic | 1 | 1.02 | 0.43 | 0.06 | 0.03 | 0.04 |
| Polypropylene Sheet | 2 | 1.01 | 0.32 | 0.07 | 0.02 | 0.04 |
| | 3 | 0.96 | 0.87 | 0.07 | 0.04 | 0.03 |
| Polystyrene Microtiter Plate Surface | 1 | 1.08 | 0.28 | 0.08 | 0.02 | 0.03 |
| | 2 | 1.22 | 0.35 | 0.09 | 0.03 | 0.04 |
| | 3 | 1.01 | 0.30 | 0.08 | 0.04 | 0.02 |

Table 7 shows that the successful detection of very small quantities of antigen must require a sufficiently large capturing surface in order to increase the probability of interaction between the solid phase and the antigen during the limited incubation period involved. This expectation is confirmed by the results obtained using an antibody-coated plastic polypropylene sheet and a polystyrene microtiter plate surface as solid phases, which failed to detect small quantities of antigen to which the macroporous polypropylene cloth responded, and which showed a greatly diminished sensitivity throughout the range of antigen concentration tested.

V(a) Commercial Adaptation of the Immunoassay: Dipstick of Macroporous Hydrophobic Synthetic Polymer Cloth A commercial form of the immunoassay was developed for application of the assay in any number of circumstances (e.g., diagnostic laboratory and field testing, etc.). One pratical form consists of affixing a small rectangular piece of macroporous polypropylene filter cloth to a strip, e.g. of cellulose acetate, which allows for the easy retrieval of the antibody-coated cloth from test samples and provides a convenient means of handling the cloth throughout the assay procedure. It is necessary to ensure that the bond created between the macroporous polypropylene cloth and the cellulose acetate does not alter the macroporous properties of the former or result in any structural features at the cloth/strip junction which might cause nonspecific retention of the conjugate.

A bond was created by first dissolving one edge of a cellulose acetate strip having the dimensions $2\frac{1}{2}'' \times \frac{1}{4}''$ polypropylene cloth piece of the same thickness, making sure not to allow any overlapping of one edge over the other. Upon evaporation of the acetone, a strong bond was formed between the cellulose acetate strip and the polypropylene filter cloth piece. The cloth portion of the resulting test strip was coated with antibody by applying 100 $\mu$l of partially denatured bovine anti-Brucella antiserum diluted 1:10 in PBS and incubating overnight at room temperature, followed by washing with PBST as previously. The antibody-coated test strip was tested in the cloth enzyme immunoassay in the manner described below.

Test strips were incubated with either 30 $\mu$l of PBS containing $1.2 \times 10^6$ B. abortus cells (plate test antigen) or 30 $\mu$l of PBS alone, for 30 minutes at room temperature. These were then washed with PBST and incubated for 30 minutes at room temperature with 25 $\mu$l of conjugate[1] diluted 1:1,000 in PBST. The cloth portions of the test strips were then washed with PBST, and were subsequently assayed for retained enzyme activity by immersion in 1 ml ABTS-indicator solution for 30 minutes with gentle shaking. The reaction was stopped by addition of 0.5 ml of 0.1M NaF and absorbance was read at 650 nm. Each determination was performed in quadruplicate, and the results of the assay are shown below in Table 8.

TABLE 8

Application of Antibody-Coated Test Strips in the Immunoassay

| No. of Cells Applied | $A_{650}$ | | | |
|---|---|---|---|---|
| per Test Strip | 1 | 2 | 3 | 4 |
| $1.2 \times 10^6$ | 0.411 | 0.427 | 0.415 | 0.435 |
| 0 | 0.023 | 0.016 | 0.020 | 0.021 |

The results of the assay demonstrate the ability of the antibody-coated test strips to detect B. abortus antigens at the concentration tested. The background level of enzyme activity was negligible, thus satisfying one of the important requirements of the immunoassay. These results were reproducible.

VI(a) Application of a Macroporous Hydrophobic Synthetic Polymer Cloths as an Adsorbant and Absorbant of Antigen in Competitive Immunoassay for B. Abortus LPS.

The following experiment shows the application of macroporous hydrophobic symthetic polymer cloth as an adsorbent and absorbent of antigen for the competitive form of the immunoassay.

Macroporous polyester non-woven cloths (DuPont SONTARA TM 8100) were incubated with 50 μl per 6×6 mm piece of 2 μg/ml solution of *B. abortus* lipopolysaccharide in PBS, overnight at room temperature. The cloths were then washed with PBST. Each cloth was incubated for 30 min, at room temperature, with 25 μl of either of the following preparations: 50 μl of PBS containing 90 ng of *B. abortus* lipopolysaccharide plus 25 μl of antibody-horseradish peroxidase conjugate diluted 10,000× in PBST, 50 μl of PBS containing a ng of lPS plus 25 μl of diluted conjugate, 50 μl of PBS containing 0.9 ng of lipopolysaccharide plus 25 μl of diluted conjugate, or 50 μl of PBS alone plus 25 μl of diluted conjugate.

The cloths were then washed with PBST and assayed for HRP by immersion in 0.5 ml of ABTS-indicator for 90 min, at room temperature. The reaction was stopped by addition of 0.5 ml of 0.1M NaF, and absorbances were read at 650 nm. The results of this experiment are recorded in Table 9 below.

TABLE 9

| Competitive Immunoassay for the Detection of *B. Abortus* Lipopolysaccharide | | | |
|---|---|---|---|
| LPS (ng) | $A_{650}$ | | Visual |
| applied per cloth | 1 | 2 | observation |
| 30 | 0.02 | 0.01 | yes |
| 3 | 0.127 | 0.115 | yes |
| 0.3 | 0.22 | 0.20 | no |
| 0 | 0.20 | 0.23 | — |

The results show clearly that at least 30 ng and 3 ng of lipopolysaccharide were detectable by simple visual examination, where the corresponding samples produced less colour than the control. However, it is equally important to note that the assay might successfully detect even lower quantities of lipopolysaccharide by colorimetric measurement. The assay offers the distinct advantages of providing an internal control for conjugate quality and requiring only one incubation step for the decisive immunological reaction. Such advantages make the competitive assay more easily adaptable for field testing.

It is believed that the detectability limit of this assay may be improved by coating the macroporous polyester cloth with a limited quantity of antigen, making the free antigen present in the test sample more competitive for the conjugate.

An improved enzyme-antibody conjugate having a higher specific activity has also been provided which should allow for the use of highly diluted conjugate in the assay, thus describing the quantity of free antigen required to prevent attachment of the conjugate to the cloth (thus increasing the sensitivity of antigen detection).

VII Detection of Antibodies Using Antigen-Coated Cloth

VII(a) Preparation of BSA-Coated Cloths

BSA was dissolved at 10 μg/ml in 0.01M sodium phosphate buffered (pH 7.2)-0.85% NaCl (PBS). As used herein, the abbreviation BSA means Brucella Serum Antibody. Fifty microliters of BSA solution was added to a macroporous hydrophobic cloth segment (6 mm square, numbered by pencil) placed in a Petri dish. After overnight incubation at room temperature, the cloth was washed 5 times with a total volume of 5 ml PBS containing 0.05% TWEEN TM 20, and stored in PBS at 4° C. until use. The activity of the cloths remained unchanged for at least 3 months. For the purpose of comparison, each well of the microtiter plate was similarly coated with 100 μl of the BSA solution and washed.

VII(b) Enzyme Immunoassay Procedure

Fifty microliters of rabbit anti-BSA serum was added either to a BSA-coated macroporous hydrophobic cloth segment (placed over a plastic sheet) or to a microtiter well and incubated at room temperature for 0.5 to 30 min. The cloth segment was then placed on an absorbent pad (e.g., a disposable diaper) using forceps and washed 5 times dropwise with a total volume of 0.3 ml TWEEN TM 20. Each well of the microtiter plate was washed 5 times with a total volume of about 2 ml TWEEN TM 20. Fifty microliters of anti-rabbit IgG-peroxidase conjugate (diluted 1:1000 in PBST) was added to each cloth segment or microtiter plate well. After incubation at room temperature for 1 to 30 min, each cloth or microtiter well was washed as above, and incubated with 250 μl of the peroxidase substrate (10 mM ABTS and 0.5 mM hydrogen peroxide in 0.05M sodium citrate buffer, pH 4.5). After 30 min incubation at room temperature, signals (absorbance at 414 nm) were determined using an EIA plate reader (Bio-Tek Inc. Model No. EL 307).

VII(c) Comparison of Various Cloths as Enzyme Immunoassay Adsorbents

Four types of commercially available cloths were compared for their capacity as enzyme immunoassay adsorbents of BSAC (a model protein antigen). The cloths were coated with BSA, and were then incubated for 30 min with either anti-BSA rabbit serum (diluted 1:100,000 in PBST) or similarly diluted normal rabbit serum devoid of anti-BSA antibodies (negative control). After washing, the captured anti-BSA IgG (a model test substance) was assayed by incubation with the anti-rabbit IgG-peroxidase conjugate for 30 min followed by the peroxidase assay for 30 min as described above.

TABLE 10

Comparison of the Enzyme Immunoassay Performed on Various BSA-Coated Cloths

| Cloth type | Absorbance at 414 nm (± standard error, n = 4) | |
|---|---|---|
| | anti-BSA serum | normal serum |
| macroporous polyester | 0.38 ± 0.02 | 0.02 ± 0.0 |
| macroporous polypropylene | 0.12 ± 0.03 | 0.03 ± 0.0 |
| macroporous polyethylene | 0.30 ± 0.02 | 0.03 ± 0.0 |
| cotton | 0.25 ± 0.04 | 0.18 ± 0.03 |

Table 10 shows that the highest specific signal (absorbance at 414 nm) was obtained with the BSA-coated macroporous polyester cloth, and that the cotton cloth was unsuitable since it gave a high background. Thus, macroporous polyester cloth was used as a solid phase in further examples of this invention in the subsequent enzyme immunoassay.

VII(d) Comparison of Cloth and Plate Under 30-min Immunoreactions

Figure 5:
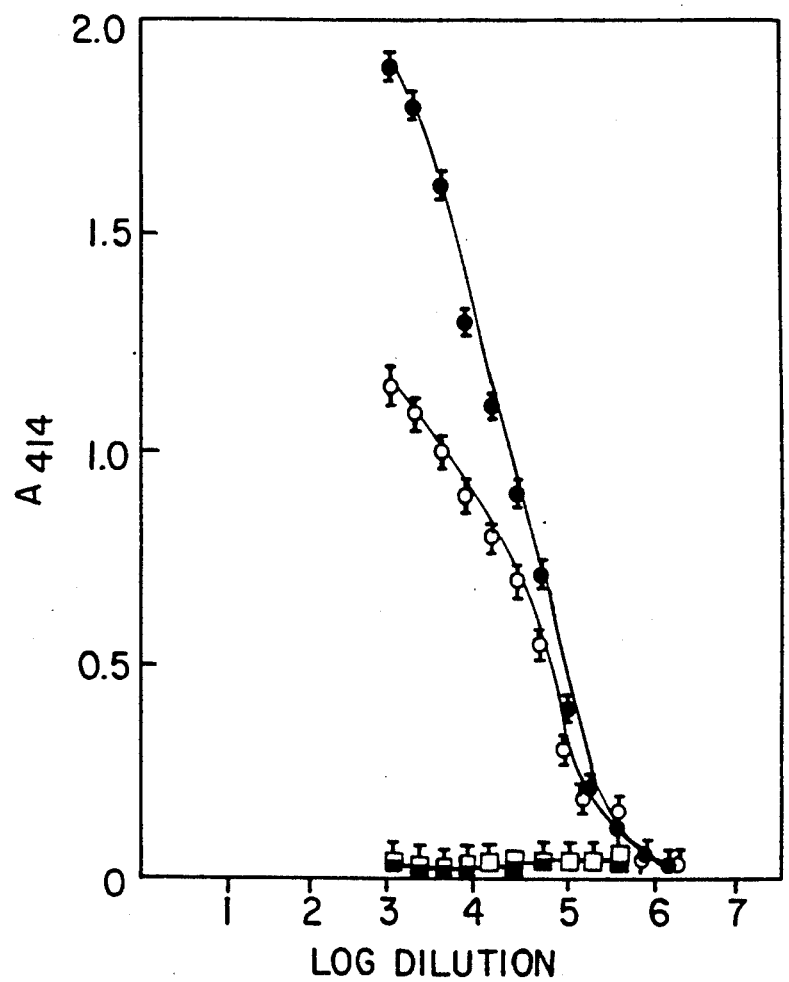

After 30 min incubations for the two immunoreactions, the signals of the enzyme immunoassay using the macroporous polyester cloth were then compared to those of a polystyrene microtiter plate over a wide range of concentrations of the test substance (anti-BSA IgG). A series of BSA-coated macroporous hydrophobic cloth segments and microtiter plate wells were incubated for 30 min with doubling dilutions of the anti-BSA serum in PBST (and normal serum as a negative control), starting with a 1:1000 dilution in the series. After washing, both adsorption supports were incubated for 30 min with the anti-rabbit IgG-peroxidase conjugate as above. The signals of the 30-min peroxidase assay are shown in FIG. 5. At the lower serum dilution, the macroporous polyester cloth produced significantly greater signals than the microtiter plate. This difference decreased at the higher dilutions and both supports gave a similar limit of detection (about 1:256,000). The negative controls exhibited very low signals for both supports.

VII(e) Comparison of Cloth and Plate Under Shorter Reaction Times

Macroporous polyester cloth (Dupont SONTARA TM 8100) has a thickness of 1.02 mm and its 6 mm square segment totally absorbed the 50 μl sample, permitting all the sample molecules to react over a large surface area. On the other hand, the microtiter plate well provided only a partial contact with the sample molecules over a limited surface area. This accounts for the differences observed in FIG. 5. Using this advantage of the macroporous polyester cloth, it is possible to reduce immunoreaction times for the enzyme immunoassay using the method of this invention.

Figure 6A:
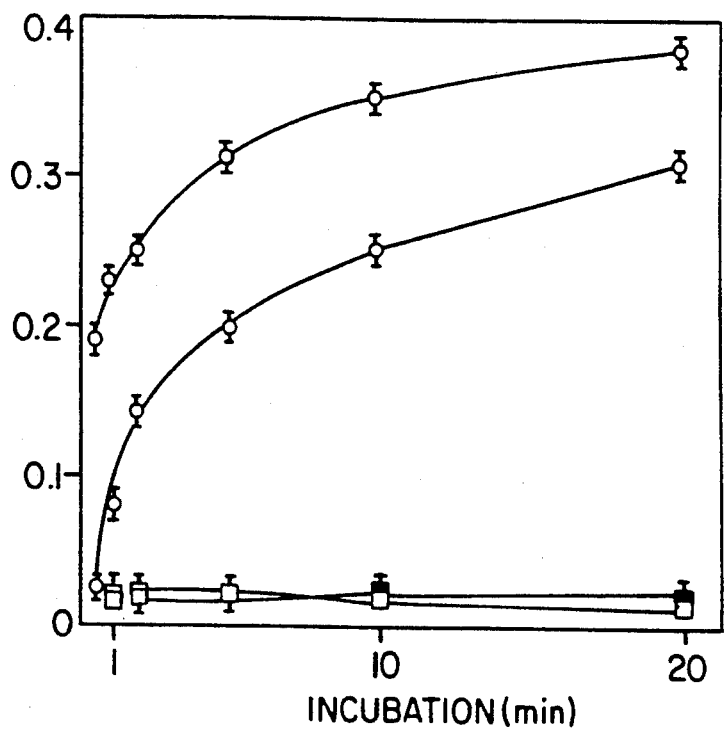

BSA-coated macroporous hydrophobic synthetic polymer cloth segments and microtiter plate wells were incubated with either anti-BSA rabbit serum (diluted 1:100,000) or similarly diluted normal rabbit serum for 0.5, 1, 2, 5, 10 and 20 min. They were then washed, and incubated for 30 min with the IgG-peroxidase conjugate. The signals of the 30 min peroxidase assay are shown in FIG. 6A. Significant signals were observed in as short as 0.5 min incubation of the sample with the cloth and only after 5 min incubation with the microtiter plate.

Figure 6B:
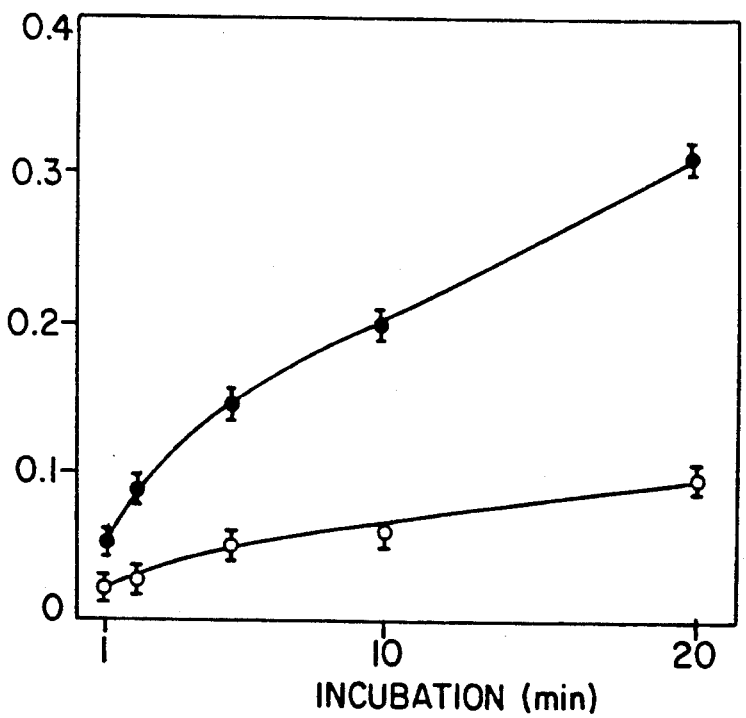

The time for the enzyme immunoassay can be further reduced by reducing the time of the second immunoreaction (between the captured IgG and the antibody-enzyme conjugate). The above comparison was repeated using a fixed incubation period of 2 min for the first immunoreaction (with anti-BSA serum) and varying the period of the second immunoreaction. FIG. 6B shows that an incubation period of 10 min of the polyester cloth with the conjugate was sufficient to produce a significant signal that can be used for the enzyme immunoassay, whereas the microtiter plate produced only weak signals throughout the range of incubation periods tested.

In FIG. 5, the enzyme immunoassay signals of the macroporous polyester cloth and microtiter plate were compared over a range of serum dilutions using 30 min incubations for both immunoreaction steps (serum and conjugate incubations). In respect of incubation times, FIG. 6A shows the effect of varying the incubation time with the serum from 0.5 to 20 min while keeping the conjugate incubation time fixed at 30 min. FIG. 6B shows the effect of keeping the serum incubation fixed at 2 min while varying the conjugate incubation time from 1 to 20 min.

VIII(a) Preparation of Lipopolysaccharide-Coated Cloth for Enzyme Immunoassay

*Salmonella typhimurium* lipopolysaccharide (Sigma, No. L-6511) was suspended in PBS-EDTA (pH 7.2) to 10 µg/m), then heated at 100° C. for 10 min. Segments (6 mm squares) of macroporous polyester cloth (DuPont SONTARA TM 8100) were each incubated with 50 µl of the LPS suspension for 16 h at room temperature, then washed with PBST and stored at 4° C. in PBS. The antigen activity of the lipopolysaccharide-cloth remained stable for at least 3 months.

VIII(b) Determination of Initial Rate of Immunoreaction on Lipopolysaccharide-Cloths The lipopolysaccharide-macroporous hydrophobic synthetic polymer cloth segments were placed on an absorbent pad using forceps, and 100 µl of goat antibody standard or rabbit serum diluted in PBS was pipetted onto each segment, one at a time, and allowed to be drawn through the macroporous hydrophobic cloth by the absorbing action of the pad. The cloth segments were then immediately rinsed dropwise with ca. 0.5 ml of PBST, and transferred to a Petri dish. The segments were then incubated with 5.0 µl of the anti-goat (or anti-rabbit) IgG antibody-horseradish peroxidase conjugate for 2–10 min. The segments were then washed with PBST as before and incubated in 0.5 ml of 10 mM 2-2'-azino-bis-(3-ethylbenzthiazoline sulfonic acid) (ABTS) and 0.5 mM $H_2O_2$ in 0.05M sodium citrate (pH 4.5) for 30 min. The reaction was stopped by addition of 0.5 ml of 0.1M NaF, and the absorbance at 414 nm ($A_{414}$) was determined. All immunoreactions and peroxidase reactions were carried out at room temperature (ca. 25° C.).

Figure 8:
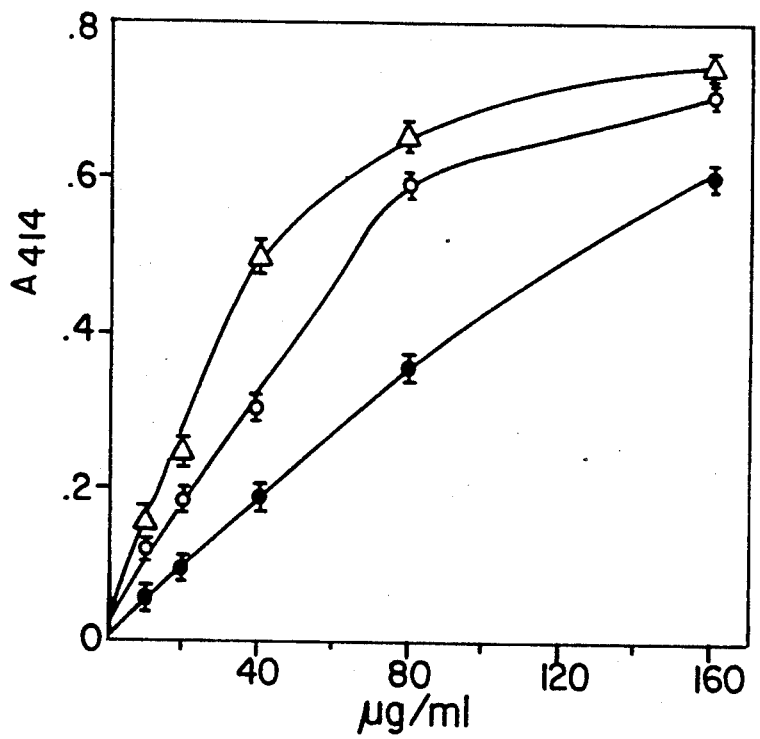

In experiments using Salmonella lipopolysaccharide antigen-coated macroporous polyester cloth and a standard preparation of purified goat anti-Salmonella antibody (CSA-1) as a model system FIG. 8 shows that, as antibody concentration is increased, the cloth enzyme immunoassay signal increases proportionally in an assay using an instantaneous exposure of the LPS-cloth to the antibody solution and three different incubation periods with conjugate. FIG. 8 also shows that significant cloth enzyme immunoassay signals can be produced on the cloth using conjugate incubations as short as 2 min, which will considerably shorten the total time required to complete the assay.

Figure 9:
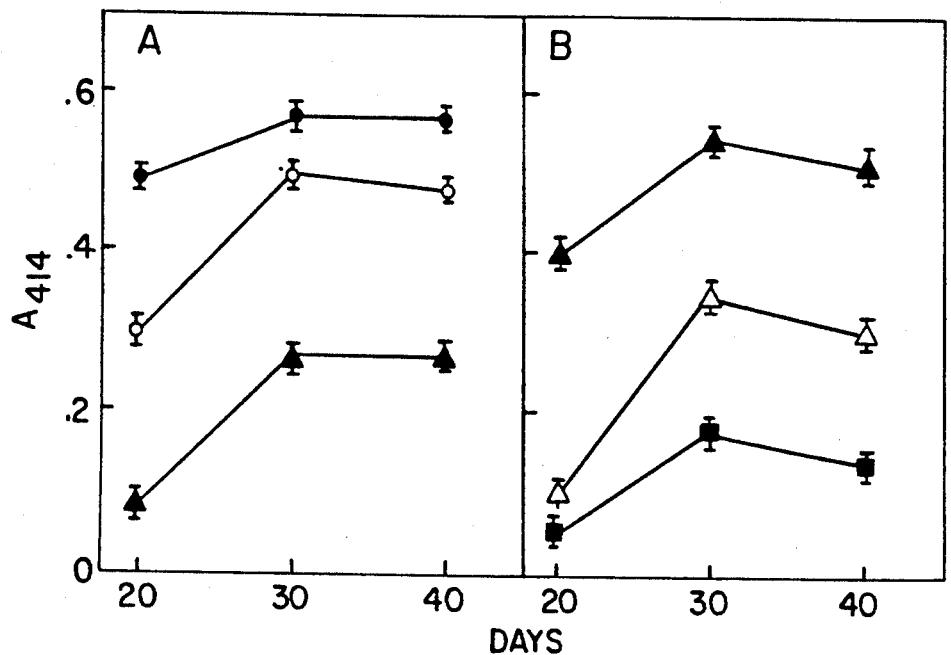

When applied to the detection of anti-Salmonella antibodies in the serum of a rabbit previously inoculated with Salmonella antigens, the instantaneous cloth enzyme immunoassay was able to quantitatively detect the antibodies in a manner paralleling the results obtained using the conventional "end point" method of determing antibody titers (FIG. 9). Thus, the instantaneous cloth enzyme immunoassay reliably provided quantitative results in an actual test subject.

IX(a) Enzyme Immunoassay Using a Microtiter Plate

A 96-well polystyrene microtiter plate (Corning, No. 25805-96) was incubated with 200 µl/well of 2 µg/ml of heated Salmonella typhimurium lipopolysaccharide in PBS-EDTA for 16 h. The wells were then washed 4×with PBST, and then incubated with 100 µl of serially diluted rabbit serum in PBS for 30 min. The plate was then washed with PBST as above, and incubated with 100 µl/-well of the anti-rabbit IgG antibody-horseradish peroxidase conjugate for 30 min. After washing with PBST, each well was then incubated with 200 µl of ABTS indicator solution for 30 min, and the $A_{414}$ was determined using a microtitier plate reader. Serum titiers were determined as the maximum dilution factor which produced a signal nearest an $A_{414}$ value of 0.2.

IX(b) Assay of Goat Anti-Salmonella Antibody Based on the Initial Rate of Immunoreaction The advantages of the cloth-based enzyme immunoassay in providing rapid immunoreactions and ease of washing (1) were applied here to measure the initial rate of immunoreaction during an instantaneous exposure of the antibody to the immobilized antigen (first immunoreaction). Segments (6 mm squares) of macroporous polyester cloth (1.0 mm thick) were coated with Salmonella lipopolysaccharide and placed on a water absorbent pad. One hundred µl of affinity purified goat anti-Salmonella antibody at various concentrations was passively absorbed through the segments into the pad, and the segments were immediately washed 5 times dropwise. This process took about 8 seconds for each sample. After all the samples were processed, the segments were incubated for 2, 5 or 10 min with anti-goat IgG antibody-peroxidase conjugate (second immunoreaction), then washed and developed in the peroxidase chromogenic solution for 30 min. FIG. 8 shows that the resulting colour was proportional to the concentration of the antibody standard within certain ranges (which decreased with the time of the second immunoreaction). Therefore, this cloth enzyme immunoassay permits the quantitative assay of antibodies on the basis of the initial rate of immunoreaction observed during the instantaneous exposure of the antibody to the immobilized antigen. Longer second immunoreactions produced higher signals, but the increase was not proportional to the time of the reaction since the amount of the conjugate used became rate-limiting with longer reactions. The use of more concentrated conjugate should increase the signals and the range of proportionality, if desired.

IX(c) Assay of Anti-Salmonella Antibody in Serum

Although the cloth enzyme immunoassay allowed for quantitation of the purified antibody, the following additional test was carried out in the assay of antibodies in serum. A rabbit was intravenously injected with Salmonella antigens to induce the formation of serum antibodies to the lipopolysaccharide antigen. After 20 days from the first injection, a second injection of antigen was administered to allow for a rapid increase in antibodies (predominantly IgG). Serum sampled at different times was then assayed by both the cloth enzyme immunoassay and the endpoint method using an lipopolysaccharide-coated microtiter plate as described above. Since the effective quantitation of antibody occurs within a certain range of concentrations (FIG. 7), it was necessary to dilute the serum samples prior to assay in order to achieve a suitable sample concentration. FIG. 9A shows that when serum was diluted 1:100 the cloth enzyme immunoassay was able to show definite increases in antibody levels in a manner reflecting the titers obtained by the endpoint method. Serum taken from the animal on day 1 (prior to immunization) was also tested in the cloth enzyme immunoassay at various dilutions and failed to produce any detectable enzyme signal in the assay. When fixed serum dilutions were allowed to incubate with the wells of an LPS-coated microtiter plate using 30 min first and second immunoreactions a similar pattern of antibody detection was obtained at a serum dilution of 1:1000 (FIG. 9B). Thus, the cloth enzyme immunoassay was able to detect change in the serum antibody level of an immunized animal during progression of the immune response in a manner comparable to the two most common enzyme immunoassay methods.

The measurement of anti-Salmonella antibody by initial rate of immunoreaction is shown in FIG. 8. Lipopolysaccharide-macroporous hydrophobic synthetic polymer segments were instantaneously reacted with a goat anti-Salmonella antibody standard at various concentrations, and then incubated with an anti-goat IgG antibody-peroxidase conjugate for either 2, 5, or 10 min, then assayed for bound peroxidase activity as described in Methods. Bound enzyme activity is expressed as mean $A_{414}\pm$standard error (n=4).

FIGS. 9A and 9B show assays of anti-Salmonella antibody in rabbit serum. A rabbit was given two intravenous injections of a S. typhimurium antigen suspension twenty days apart. Serum was sampled on day 1 (prior to first injection), day 20 (prior to second injection), and at ten-day intervals thereafter. Serum samples were diluted 1:10, 1:100, 1:1000, 1:10,000, or 1:20,000 in PBS, and were then assayed for anti-Salmonella antibody using (A) the macroporous hydrophobic cloth enzyme immunoassay with instantaneous exposure of serum (using a 5 min. further immunoreaction) as described above, or (B) by incubation of each sample with the well of an lipopolysaccharide-coated microtiter plate for 30 min followed by washing and a further 30 min incubation with anti-rabbit IgG-peroxidase conjugate. Serum samples assayed by both methods prior to immunization (day 1) failed to produce detectable enzyme signals. Bound enzyme signals are expressed as mean $A_{414}\pm$standard error (n=4). Anti-Salmonella antibody titers were determined for each sample using the endpoint method. Serum titiers were 0 (day 1); 3,260 (day 20); and 13,040 (days 30 and 40).

X Detection of Salmonella Antibodies in Egg Yolk Using LPS-Coated Macroporous Hydrophobic Synthetic Polymer Cloths X(a) Preparation of LPS-Coated Macroporous Hydrophobic Synthetic Polymer Cloths In order to establish that cloth enzyme immunoassay using antigen coated macroporous hydrophobic synthetic polymer cloths, e.g., lipopolysaccharide coated macroporous polyester cloths, could be used for the rapid assay of specific antibodies in a viscous sample, the following example shows the use for the rapid assay of spcific antibodies in an egg yolk sample, which is one possible application of the method.

Nonwoven macroporous polyester cloth (DuPont, SONTARA TM 8100) was cut into 6 mm square segments. For coating the cloth segments, Salmonella typhimurium lipopolysaccharide was dissolved at 10 µg/ml in PBS containing 0.05 M ethylenediaminetetraacetate (EDTA) (pH 7.2) and then heated at 100° C. for 10 min. Each cloth segment was then incubated with 50 µl of the EDTA-heat-treated lipopolysaccharide solution for 16 h at room temperature, and then washed with a total of 5 ml of PBST on a filter under suction. The lipopolysaccharide-coated macroporous polyester cloth segments (LPS-cloth) were stored in PBS at 4° C.

X(b) Detection of Salmonella

Chicken egg yolk was diluted 1:5 in PBS, and a 10 µl sample was incubated with each lipopolysaccharide-macroporous hydrophobic synthetic polymer cloth for 5 min at room temperature in a Petri dish. The macroporous hydrophobic synthetic polymer cloth were then placed on an absorbent pad (a disposable diaper) and each segment was washed 10 times dropwise with a total of about 1 ml of TWEEN TM 20. The macroporous hydrophobic synthetic polymer cloths were then returned to a clean Petri dish and incubated with 50 µl of the anti-chicken IgG-peroxidase conjugate for 5 min at room temperature, then washed with TWEEN TM 20 as above. Peroxidase was assayed by shaking each macroporous hydrophobic synthetic polymer cloth segment in 0.5 ml of substrate solution (10 mM 2-2'-azino-bis-(3-ethylbenzthiazoline sulfonic acid) (ABTS) and 0.5 mM $H_2O_2$ in 0.05M pH 4.5 sodium citrate buffer) for 15 min at room temperature. The enzyme reaction was stopped by the addition of 0.5 ml of 0.1M NaF, and the developed substrate solution was transferred to a 1 ml-capacity cuvette (1 cm light path) and its absorbance at 414 nm ($A_{414}$) was determined.

XI(a) Detection of IgG in Chicken Egg Yolks.

In instances where the viscosity of the test sample (e.g., egg yolk) may affect the result of the assay (e.g., give limited diffusion rate), a longer (e.g., 5 min) incubation of the sample with the LPS-coated macroporous hydrophobic synthetic polymer cloth should be used, rather than "instantaneous" incubations as described above. This still provides a rapid assay.

XI(b) Specificity of Egg Yolk Antibodies Adsorbed onto LPS-Cloth

Ten macroporous polyester cloth segments (6 mm squares) were incubated with 1 ml of an S. typhimurium lipopolysaccharide solution (100 µg/ml) prepared as above for 16 h at room temperature. The cloths were then washed with PBS and incubated with 1 ml of egg yolk diluted 1:5 in PBS for 1 h at room temperature, and then washed with PBS. They were then blotted, and the adsorbed antibodies were eluted by shaking the cloths in 1 ml of 0.1M glycine-HCl (pH 2.2) for 5 min at room temperature. The liquid containing the eluted antibodies was then removed and neutralized by the addition of 0.2 volume of 1.0M Tris-HCl (pH 8.0). The eluted antibodies were assayed immediately by the cloth enzyme immunoassay on polyester cloth coated with various lipopolysaccharide antigens.

XI(c) Cloth-Based Enzyme Immunoassay of Anti-Lipopolysaccharide IgG in Egg Yolk

To demonstrate the presence of anti-lipopolysaccharide IgG in egg yolk, the yolks of a number of chicken eggs collected from various local (i.e., the Ottawa, Canada region) independent produce retailers were screened by the cloth enzyme immunoassay. Macroporous polyester cloth segments were coated with lipopolysaccharide from either *S. typhimurium, E. coli* K-235, *E. coli* 0127:B8, or *P. aeruginosa*, and were used for the capture of IgG from the yolks. The captured IgG was then detected with the anti-chicken IgG-peroxidase conjugate. Of the yolks screened initially, 2 (yolks A and B) produced considerable cloth enzyme immunoassay signals using the Salmonella lipopolysaccharide-macroporous hydrophobic synthetic polymer cloth, (see Table 11, below). These egg yolks also produced varying cloth enzyme immunoassay signals using the non-Salmonella lipopolysaccharide-macroporous hydrophobic synthetic polymer cloths. This suggests that in addition to anti-Salmonella IgG, the egg yolks also contain IgG specific for various non-Salmonella lipopolysaccharide antigens.

In order to confirm that the signals on the Salmonella lipopolysaccharide-macroporous hydrophobic synthetic polymer cloths were due to the presence of anti-Salmonella IgG, antibodies from yolk A or B adsorbed onto *S. typhimurium* LPS-cloth were eluted with pH 2.2 buffer and immediately neutralized as described above. These eluted antibodies were then subjected to the enzyme immunoassay using the Salmonella lipopolysaccharide-macroporous hydrophobic synthetic polymer cloths of various non-Salmonella lipopolysaccharide-macroporous hydrophobic synthetic polymer cloths for antibody capture as before. Table 12 (below) shows that IgG eluted from *S. typhimurium* lipopolysaccharide-macroporous hydrophobic synthetic polymer cloth gave significant signals with the Salmonella lipopolysaccharide-macroporous hydrophobic synthetic polymer cloth but not with the non-Salmonella lipopolysaccharide-macroporous hydrophobic synthetic polymer cloths. This confirms that the cloth enzyme immunoassay signals obtained using the Salmonella lipopolysaccharide-cloth (see Table 11) were due to the presence of anti-Salmonella IgG in the yolks.

Figure 7:
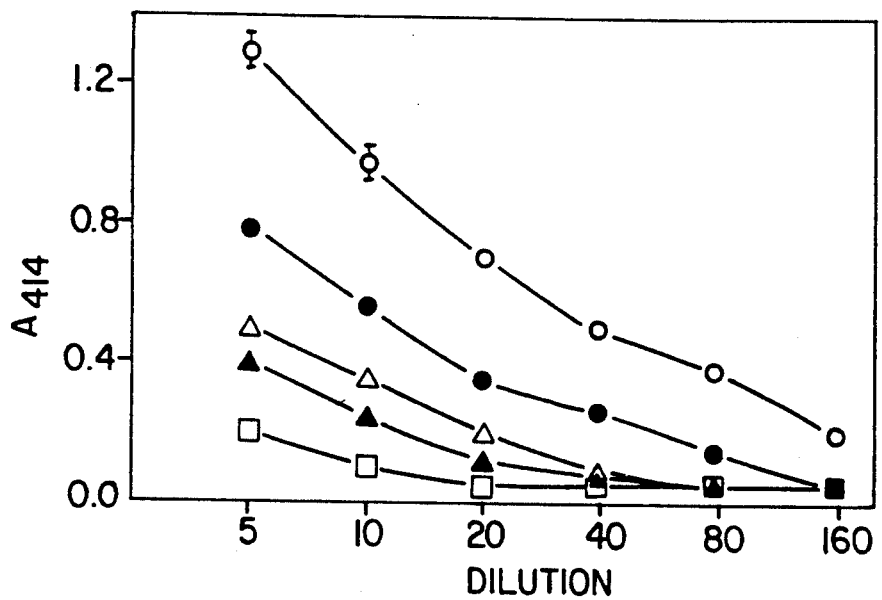

The specificity of yolk A IgG for the lipopolysaccharide of Salmonella species other than *S. typhimurium* was also tested in the cloth enzyme immunoassay. Macroporous polyester cloth segments were coated with lipopolysaccharide from three Salmonella species in addition to *S. typhimurium* and used in the assay of serial dilutions of yolk A. FIG. 7 shows that macroporous hydrophobic synthetic polymer cloth coated with *S. typhimurium* lipopolysaccharide produced the highest signals at all dilutions, followed by those coated with *S. typhosa*, then *S. enteritidis*, and finally *S. minnesota*. Uncoated macroporous hydrophobic synthetic polymer cloth (no lipopolysaccharide) did not produce a significant signal at any dilution, confirming that the signals are due to the lipopolysaccharide on the macroporous hydrophobic synthetic polymer cloth. Since *S. typhimurium* is one of the most common Salmonella contaminants of chickens, it is likely that the yolk contains predominantly anti-*S. typhimurium* IgG which shows cross-reactivity with the other Salmonella species. Antibody reactivities to the antigens of Salmonella species which were not tested may also be present. Since the signals progressively decreased with increasing dilutions of the yolk, this enzyme immunoassay appears to be quantititive and is believed to be useful for the measurement of anti-Salmonella IgG levels in egg yolks.

XI(d) Relative Anti-Salmonella IgG Levels in Eggs from Various Sources

Since macroporous polyester cloth coated with *S. typhimurium* lipopolysaccharide appears to be suitable for use in the cloth enzyme immunoassay of anti-Salmonella IgG in egg yolk, a number of eggs obtained from various sources were screened in order to determine if any fluctuation in anti-Salmonella IgG levels could be detected. Egg yolks were screened by the enzyme immunoassay using *S. typhimurium* lipopolysaccharide-macroporous hydrophobic synthetic polymer cloth and a fixed dilution of the yolk in order to measure differences in the extent of immunoreaction (as judged by the cloth enzyme immunoassay signal) according to the level of specific IgG present. Table 13 (below) shows that out of 113 eggs screened, the majority of those obtained from 3 out of 4 local (i.e., in the Ottawa, Canada area) independent produce retailers and 2 major supermarket chains (also in the Ottawa, Canada area) produced lower cloth enzyme immunoassay signals (i.e., within an arbitrarily defined $A_{414}$ range of 0–0.6). Signals from the egg yolks of the remaining independent produce retailers were also generally low, but at least 2 of the yolks gave high signals ($A_{414}>1.0$). On the other hand, the majority of eggs obtained from a small local farm produced generally high signals ($A_{414}>0.6$), with only 6 out of 18 eggs tested responding in the lower ranges. Although no epidemiological information was available, it is believed that those sources of eggs exhibiting a significant proportion of yolks giving high cloth enzyme immunoassay signals (hence, elevated anti-Salmonella IgG levels) have had some contact with Salmonella organisms. This is expecially likely in the case of the small local farm, where sanitary conditions may not meet the same standards as rearing facilities supplying the larger retailers.

FIG. 7 shows the detection of egg yolk A IgG to various Salmonella species. Macroporous polyester cloth segments were coated with lipopolysaccharide from either *S. typhimurium*, *S. typhosa*, *S. minnesota*, *S. enteritidis*, or no lipopolysaccharide. These cloths were then used in the of various dilutions of egg yolk A in PBS.

TABLE 11

Cloth Enzyme Immunoassay of Anti-LPS IgG in Egg Yolk[a]

| LPS | $A_{414}$[b] | |
|---|---|---|
| | Yolk A | Yolk B |
| *S. typhimurium* | 1.35 ± 0.11 | 0.45 ± 0.04 |
| *E. coli* K-235 | 0.80 ± 0.06 | 0.51 ± 0.03 |
| *E. coli* 0127:B8 | 0.37 ± 0.05 | 0.31 ± 0.05 |
| *P. aeruginosa* | 0.16 ± 0.01 | 0.25 ± 0.03 |

[a]Macroporous polyester cloth segments were coated with lipopolysaccharide from either *S. typhimurium* or a variety of non-Salmonella Gram-negative bacteria. These lipopolysaccharide-cloths were then used in the enzyme immunoassay of IgG from two chicken yolks (A and B), which had been identified as having considerable levels of anti-Salmonella IgG during the preliminary screening of a number of eggs.
[b]Mean $A_{414}$ value ± standard error (n = 4).

TABLE 12

Specificity of Egg Yolk IgG After Elution from *S. Typhimurium* LPS-Cloth[a]

| LPS | $A_{414}$[b] | |
|---|---|---|
| | Yolk A | Yolk B |
| *S. typhimurium* | 0.51 ± 0.04 | 0.20 ± 0.02 |
| *E. coli* K-235 | 0.08 ± 0.0 | 0.05 ± 0.0 |
| *E. coli* 0127:B8 | 0.09 ± 0.01 | 0.05 ± 0.0 |
| *P. aeruginosa* | 0.06 ± 0.0 | 0.04 ± 0.0 |

[a]Antibodies from either egg yolk A or B adsorbed to *S. typhimurium* lipopolysaccharide-cloth were eluted with pH 2.2 buffer and then immediately neutralized. The eluted samples were then subjected to the enzyme immunoassay using macroporous polyester cloth segments coated with lipopolysaccharide from *S. typhimurium* or various other non-Salmonella Gram-negative bacteria.
[b]Mean $A_{414}$ value ± standard error (n = 4).

TABLE 13

Relative anti-Salmonella IgG levels in eggs from various sources[a]

| Source[b] | No. of eggs within absorbance range | | | | | |
|---|---|---|---|---|---|---|
| | 0–0.2 | 0.2–0.4 | 0.4–0.6 | 0.6–0.8 | 0.8–1.0 | >1.0 |
| 1 (16) | 11 | 4 | 1 | 0 | 0 | 0 |
| 2 (28) | 17 | 6 | 2 | 1 | 0 | 2 |
| 3 (19) | 15 | 4 | 0 | 0 | 0 | 0 |
| 4 (8) | 1 | 5 | 2 | 0 | 0 | 0 |
| 5 (18) | 3 | 3 | 0 | 1 | 4 | 7 |
| 6 (12) | 8 | 4 | 0 | 0 | 0 | 0 |
| 7 (12) | 7 | 4 | 1 | 0 | 0 | 0 |

[a]Fresh egg yolks from a variety of sources were diluted 1:5 in PBS and assayed for anti-Salmonella IgG by the cloth enzyme immunoassay using *S. typhimurium* lipopolysaccharide-cloth. Yolks were assayed in triplicate (n = 3) and the mean $A_{414}$ value was used to determine the absorbance range (in 0.2 absorbance unit increments) assigned to each yolk.
[b]Sources No. 1, 2, 3, and 4 are separate independent produce retailers. source No. 5 is a small local (i.e., in the Ottawa, Canada area) farm, and sources No. 6 and 7 are major supermarket chains. The numbers in brackets indicate the total number of eggs tested from each source.

XII(a) Detection of Salmonella Antigens In Chicken Meat Using Cloth Enzyme Immunoassay The cloth enzyme immunoassay using macroporous polyester cloth as the adsorbent for the capture antibody was performed as follows.

Macroporous polyester cloth (DuPont, SONTARA TM 8100) was cut into 6-mm square segments. Each segment was incubated with 50 μl of the CSA-1 antibody (50 μg/ml in PBS) for 6–16 h at room temperature, then thoroughly washed with 5 ml PBST using a vacuum filtration apparatus. The antibody-coated macroporous polyester cloths were stored in PBS at 4° C. and remained stable for at least 3 months. 50 μl of antigen sample was pipetted onto each antibody-coated cloth in a petri dish and incubated for 30 min (unless otherwise stated) at room temperature, then the macroporous polyester cloths were placed on an absorbent pad (a disposable diaper) and washed five times dropwise with a total of about 0.3 ml of TWEEN TM 20. The macroporous polyester cloths were returned to a clean Petri dish and incubated with 50 μl of the CSA-1 antibody-horseradish peroxidase conjugate for 30 min at room temperature. The cloths were then washed with TWEEN TM 20 as before and incubated in 0.5 ml of 10 mM 2'-2'-azino-bis-(3-ethylbenzothiazoline sulfonic acid) (ABTS) and 0.5 mM $H_2O_2$ in 0.05M sodium citrate (pH 4.5) for 30 min at room temperature. The reaction was stopped by addition of 0.5 ml of 0.1M NaF, and the abosrbance at 414 nm ($A_{414}$) was determined.

XII(b) Chicken Breast Paste

Fresh grade A chicken breast meat was obtained locally (i.e., in the Ottawa, Canada area) and blended to a paste using a food processor and inoculated with Salmonella, then analysed by the enzyme immunoassay immediately or after enrichment for 16 h at 37° C. in tetrathionate and selenite cystine or nutrient broth.

XIII Enzyme Immunoassay After Concentration of Antigens onto Antibody-Coated Macroporous Hydrophobic Synthetic Polymer Cloth Macroporous polyester cloth was cut into 1-cm diameter discs and each was incubated with 100 μl of the CSA-1 antibody (50 μg/ml in PBS) for 6–6 h, at room temperature. Each disc was then inserted at the bottom of an 1 cm diameter QUIK-SEP TM disposable polypropylene column (Isolab, Inc. No. QS-U). Solid-free samples were then passed (by gravity flow) through the columns at a flow rate of 25–50 ml/h. As unconcentrated controls, 100 μl aliquots of the samples were incubated with antibody-coated macroporous hydrophobic synthetic polymer cloth discs in a petri dish for 60 min, then treated as below. Upon passage of the entire samples through the columns, the discs were then incubated in situ (in the column) with 100 μl of the CSA-1 antibody-horseradish peroxidase conjugate for 30 min, washed with PBST (4 ml per column), and incubated in situ with 1 ml of ABTS for 30 min with gentle agitation of the column. Reactions were stopped by the addition of 1 ml of 0.1M NaF, and the absorbance (414 nm) of the effluent from the column was determined.

XIV Effect of EDTA and Heat on Cloth Enzyme Immunoassay of Salmonella Antigen

Figure 10:
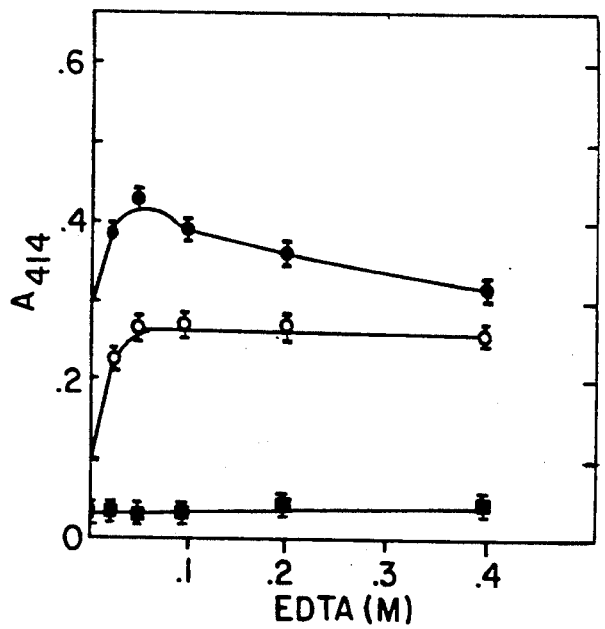

Treatment with 10 mM EDTA at room temperature is known to release lipopolysaccharide (LPS) from *Escherichia coli*, *Salmonella anatum*, and *S. minnesota*. Also, heat-killed Salmonella cells have been widely used as an antigen source for antibody production. The effect of both EDTA and heat treatments on the detection of Salmonella antigens by cloth enzyme immunoassay was studied using *S. typhimurium* as a model antigen. Washed *S. typhimurium* cells were suspended at $3 \times 10^7$ cells/ml in various concentrations of EDTA in PBS (EDTA-PBS), and 1-ml portions were either heated at 100° C. for 10 min or left at room temperature. 50 μl suspensions (containing $1.5 \times 10^6$ cells) or EDTA-PBS alone (negative control) were then incubated for 30 min with 6-mm squares of macroporous polyester cloths which had been pre-coated with anti-Salmonella antibody. The captured antigen was detected by the antibody-horseradish peroxidase conjugate. FIG. 10 shows that EDTA treatments at room temperature enhanced the cloth enzyme immunoassay signal (at all EDTA concentrations tested) in comparison with the untreated cells. However, a combination of EDTA and heat treatment gave even greater enhancement. The EDTA enhancement was maximal at 50 mM EDTA and declined at the higher EDTA concentrations. Heating Salmonella cells in 50 mM EDTA caused a fourfold increase in the cloth enzyme immunoassay signal as compared to the untreated cells. The negative controls show negligible signals which were not affected by the EDTA treatment. At 50 mM EDTA, 2 min heating (of 1 ml of cell suspension) was found to be sufficient, but heating for at least 10 min is recommended to ensure the killing of all Salmonella cells for safer handling.

When EDTA-heat-treated cells were centrifuged at 10 000×g for 10 min approximately 85% of the total antigenic activity (determined by the cloth enzyme immunoassay) was found in the supernatant (data not shown). It is therefore believed that the treatment caused the dissociation of the cell-associated antigens into smaller non-sedimentable units.

XV Kinetics of Immunoreactions of the EDTA-Heat-Treated Antigens

Figure 11:
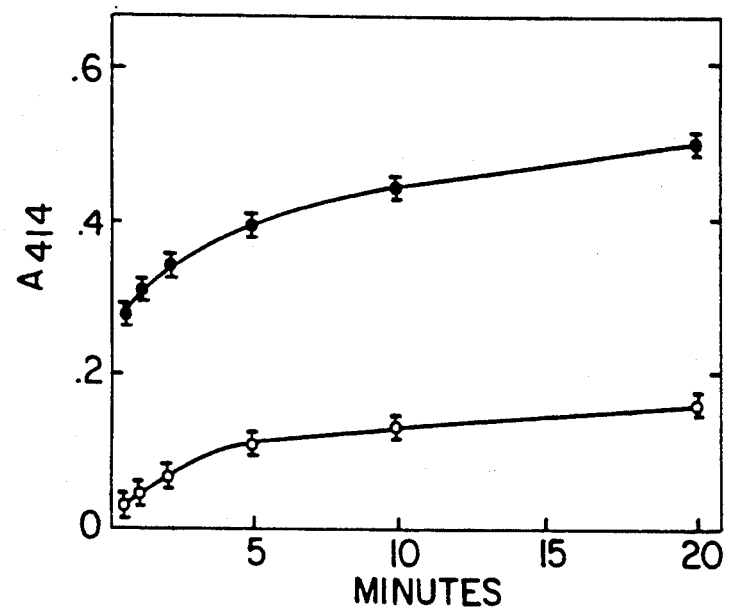

In the above examples, the EDTA-heat-treated cells were allowed 30 min to react with antibody adsorbed onto the macroporous hydrophobic synthetic polymer cloth. The captured antigens were then detected by 30 min incubation with the conjugate followed by 30 min. incubation with the peroxidase substrate. FIG. 11 shows the effect of varying the immunoreaction time of EDTA-heat-treated and untreated cells with the adsorbed antibody, while maintaining other reaction conditions as above. After as little as 0.5 min immunoreaction, the treated cells gave significant enzyme immunoassay signals, whereas the untreated cells produced only barely detectable signals. These results confirm that the EDTA-heat-treatment dissociates Salmonella antigens into smaller units which react faster with the absorbed antibody.

XVI Detection of Salmonella in Chicken Meat

Figure 12:
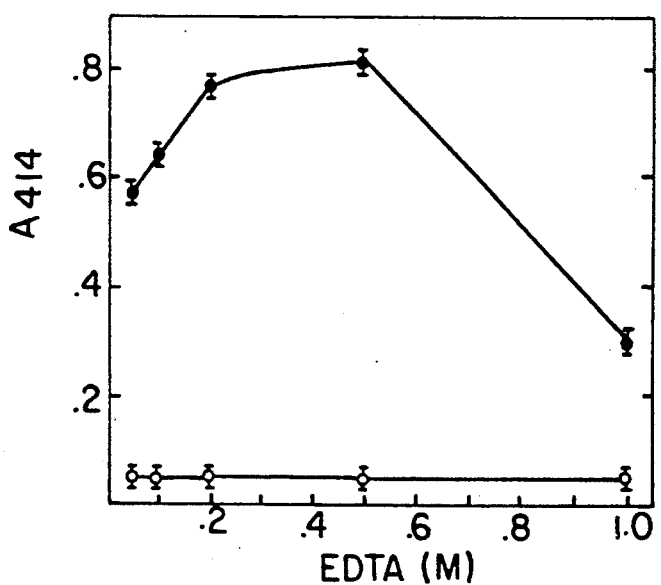

Since EDTA-heat treatment allows for the extraction of Salmonella antigens into a supernatant after centrifugation, it should also be possible to prepare solid-free antigens from solid-rich Salmonella samples. As an example, the extraction of Salmonella antigens from chicken breast was examined. For this, concentrations of EDTA higher than 50 mM may be required since the effective concentration of EDTA will be reduced by the divalent ions present in the meat. Therefore, chicken breast paste was inoculated with Salmonella ($6 \times 10^8$ cells per g of paste), and heated in various EDTA concentrations. The antigens extracted in the supernatants were assayed by the cloth enzyme immunoassay. FIG. 12 shows that the EDTA-heat treatment extracted the antigens from the meat most efficiently in the range of 0.2M to 0.5M EDTA (judged from the cloth enzyme immunoassay signals) and that the uninoculated samples gave negligible signals (above the background) which were unaffected by the different EDTA concentrations.

Figure 13:
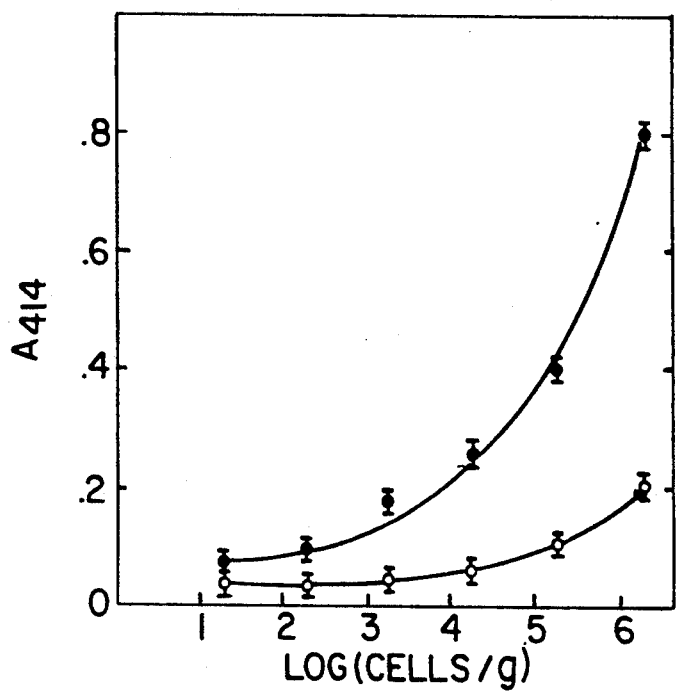

XVII Concentration of Dissociated Antigens on Antibody-Coated Macroporous Hydrophobic Synthetic Polymer Cloth The above examples show that Salmonella antigens can be extracted into a solid-free liquid. However, in practice the concentration of the antigens in the sample liquid may not be sufficiently high to be detected by the cloth enzyme immunoassay. Since larger volumes of the sample liquid can be passed through the antibody-coated macroporous hydrophobic synthetic polymer cloth because of its macroporosity, it should be possible to concentrate the antigens on the macroporous hydrophobic synthetic polymer cloth to a detectable level. To demonstrate this, 10 g of the chicken meat was inoculated with various numbers of Salmonella cells. The solid-free antigen samples were then prepared by EDTA-heat extraction and passed through the antibody-coated macroporous hydrophobic synthetic polymer cloths. The concentrated antigens were assayed in situ (i.e., in the columns) by the cloth enzyme immunoassay. FIG. 13 shows that the EDTA-heat-extracted samples could be readily concentrated by filtration through the antibody-coated macroporous hydrophobic synthetic polymer cloth. After concentration the cloth enzyme immunoassay detected Salmonella in the meat inoculated at a density of $2 \times 10^3$ cells/g whereas only $2 \times 10^5$ cells/g could be detected without concentration. The cloth enzyme immunoassay signals increased with increasing levels of inoculation. It is believed that even lower cell densities could be detected by this method by filtering larger volumes of liquid sample, as the macroporous polyester cloth of the present invention does not encounter difficulties with clogging upon passage of colloidal samples, as do microporous filters, e.g., nitrocellulose and nylon membranes as in the prior art.

XVIII Detection of Salmonella Cells by Combined Enrichment-Cloth Enzyme Immunoassay The presence of extremely low number of viable Salmonella cells in food samples has traditionally required that the samples be enriched to higher cell densities by incubation in various growth media before identification. A series of pre-enrichment and selective enrichment steps which require a minimum of 2 days have previously been used to identify Salmonella by enzyme immunoassay on non-porous supports. To demonstrate the possibility of detecting very low numbers of Salmonella cells, 5-g samples of the chicken meat were inoculated with approx. 50 Salmonella cells and were incubated for 16 h at 37° C. with 10 ml of either one of two commonly used selective broths, tetrathionate and selenite cystine, or nutrient broth. The solid-free antigen samples were then prepared by EDTA-heat extraction, concentrated on the antibody-coated macroporous hydrophobic synthetic polymer cloths, and assayed by the cloth enzyme immunoassay. Table 14 (below) shows that all three broths tested easily allowed for the detection of the cells by the cloth enzyme immunoassay after the 16-h enrichment period, and all of these broths produced similar results in terms of the cloth enzyme immunoassay signals obtained. The reason for the elevated background signals observed in the uninoculated control samples is not clear, but the very large differences between the signals obtained for the inoculated samples and the controls allow for a very clear distinction between the two. Although nutrient broth seems adequate, in practice the use of a selective broth is preferred in order to avoid competition by other contaminating microorganisms during enrichment. However, the sole use of a selective broth for enrichment may not permit the growth of damaged salmonella present in nutrient-deficient samples.

TABLE 14

| Combined Enrichment-Cloth Enzyme Immunoassay for the Detection of Salmonella Cells in Chicken Meat[a] | | |
|---|---|---|
| Enrichment broth | No. cells/g meat | $A_{414}$[b] |
| Tetrathionate | 0 | 0.30 ± 0.03 |
|  | 10 | 1.16 ± 0.08 |
| Sellenite cystine | 0 | 0.25 ± 0.03 |
|  | 10 | 1.28 ± 0.06 |
| Nutrient broth | 0 | 0.30 ± 0.02 |
|  | 10 | 1.33 ± 0.06 |

[a]5 g of the chicken breast paste was mixed with 1 ml of M 63 medium containing 0 or approx. 50 Salmonella cells, then with 10 ml of enrichment broth, and incubated for 16 h at 37° C. without shaking. The mixtures were then mixed with 2 ml of 1 M EDTA (pH 7.2) in PBS, autoclaved at 121° C. for 5 min, then centrifuged at 10,000 × g for 10 min at 4° C. The antigens in the supernatants were concentrated onto antibody-coated cloth and assayed by the cloth enzyme immunoassay.
[b]Mean $A_{414}$ value ± standard error (n = 3).

FIG. 10 shows the effect of heating Salmonella cells in various concentrations of EDTA on the cloth enzyme immunoassay signal. Washed Salmonella cells were suspended at $3 \times 10^7$ cells/ml in PBS containing various concentrations of EDTA and heated at 100° C. for 10 min or left at room temperature. These samples were then processed in the cloth enzyme immunoassay as described above. A series of negative controls (no antigens), consisting of PBS containing various concentrations of EDTA alone, are also shown. The cloth enzyme immunoassay signals ($A_{414}$) are plotted as mean value±standard error (n=3).

FIG. 11 shows the kinetics of the antibody-antigen reaction fo EDTA-heat-treated and untreated Salmonella samples. Washed Salmonella cells were suspended at $3 \times 10^7$ cells/ml in PBS with or without 50 mM EDTA. The suspension in EDTA-PBS was heated at 100° C. for 10 min while the suspension in PBS (untreated sample) was left at room temperature. The samples were then incubated with antibody-coated macroporous hydrophobic synthetic polymer cloths for various lengths of time, then processed in the cloth enzyme immunoassay as described in Materials and Methods.

The cloth enzyme immunoassay signals ($A_{414}$) are plotted as mean value±standard error (n=3).

FIG. 12 shows the extraction of Salmonella antigens from chicken meat by EDTA-heat treatment. Samples (0.1 g) of chicken breast paste were mixed with 0.1 ml of PBS containing $6 \times 10^7$ Salmonella cells, or PBS alone, then heated at 100° C. for 10 min in the presence of 0.5 ml of PBS containing various concentrations of EDTA. After cooling, the mixtures were centrifuged (10,000×g for 10 min) and the antigens in the supernatants were assayed by the cloth enzyme immunoassay (30 min immunoreactions with the antigens). The cloth enzyme immunoassay signals ($A_{414}$) are plotted as mean value±standard error (n=3).

FIG. 13 shows the concentration of dissociated Salmonella antigens onto antibody-coated macroporous hydrophobic cloth. Several 10-g samples of chicken breast paste were inoculated with various numbers of Salmonella cells and then autoclaved at 121° C. for 5 min in the presence of 50 ml of PBS containing 0.2M EDTA (pH 7.2). Sample solids were then removed by centrifugation (10,000×g for 10 min) and the resulting supernatants were passed through antibody-coated macroporous hydrophobic synthetic polymer cloth discs inserted at the bottom of columns. The captured antigens were then assayed by the cloth enzyme immunoassay after or before concentration on antibodycoated macroporous hydrophobic synthetic polymer cloth.

XIX(a) Affinity Purification and Biotinylation of Antibodies

Ten lipopolysaccharide-macroporous hydrophobic synthetic polymer cloth segments were blotted and incubated with 1 ml of anti-Salmonella serum in PBS for 30 min at room temperature. The segments were then washed with PBS and blotted. For biotinylation, the macroporous hydrophobic synthetic polymer cloth segments were suspended in 1 ml of 0.01M borate-buffered (pH 8.0)-0.85% NaCl (BBS) and mixed with 10 μl of a BACHS solution (10 mg/ml in dimethylformamide). After 30–60 min incubation at room temperature with occasional gentle stirring, the macroporous hydrophobic synthetic polymer cloth segments were washed with PBS as above and blotted, and the bound biotinylated antibodies were eluted by shaking the segments in 1 ml of 0.1M glycine-HCl (pH 2.2) for 5 min at room temperature. The eluted liquid sample was then removed with a pipette and neutralized by the addition of 0.2 volume of 1.0M Tris-HCl (pH 8.0). This solution could then be used immediately in the EIA of Salmonella antigens or stored at 4° C. for at least 2 weeks. For prolonged storage at −20° C., we recommend dialyzing the solution against PBS and adding bovine serum albumin (BSA) to a final concentration of 5% (w/v) as a stabilizer.

XIX(b) Protein Assay

Proteins were measured using a commercial Coomassie protein assay (Pierce, No. 23201) which was not affected by Tris in the protein samples. BSA was used as the protein standard.

XIX(c) Determination of Antibody Titers

Fifty microliters of serially diluted antibody in PBS were applied on lipopolysaccharide macroporous hydrophobic synthetic polymer cloth segments and then incubated for 30 min at room temperature in a petri dish. Each segment was then washed with PBST and then incubated with 50 μl of anti-rabbit IgG-alkaline phosphatase conjugate for 30 min as above. After washing with PBST, each segment was incubated for 30 min at 37° C. with 0.5 ml of 15 mM p-nitrophenyl phosphate in 1.0M diethanolamine buffer (pH 9.8) containing 0.5 mM mgCl$_2$. The reaction was stopped by addition of 0.5 ml of 0.1M Na$_2$HPO$_4$,) and the absorbance at 404 nm ($A_{404}$) was determined. Titer values were determined as the maximum dilution factor which produced an enzyme immunoassay signal nearest an $A_{404}$ value of 0.2.

XX Test of Biotinylated Antibody in the Enzyme Immunoassay of Salmonella Antigens

*S. typhimurium* strain LT2 was grown by shaking in DIFCO ™ buffered peptone water (BPW) at 37° C. to a density of about $10^9$ cells/ml, and was then diluted with BPW to various cell densities (determined by viable counts). To solubilize the antigens (5), the samples were mixed with 0.1 volume of 0.5M EDTA in PBS (pH 7.2), heated at 100° C. for 10 min, then cooled to room temperature and used immediately for antigen assay by the cloth-based enzyme immunoassay.

Macroporous polyester cloth segments (6 mm squares) were incubated with 50 μl of CSA-1 antibody (50 μg/ml in PBS) for 16 h at room temperature and then washed with PBST. The antibodycoated cloth segments were then incubated with 50 μl of the Salmonella samples (prepared as above) for 30 min at room temperature, and washed with PBST. The macroporous polyester cloth segments were then incubated with 50 μl of either biotinylated antibodies (0.05 μg/ml in PBST) or the CSA-1 and then washed with PBST. The segments treated with biotinylated antibodies were further incubated with 50 μl of the streptavidin-alkaline phosphatase conjugate for 30 min at room temperature, then washed with PBST. Each segment was then assayed for bound alkaline phosphatase activity by incubating with substrate as above.

XXI Affinity Purification of Antibody on Lipopolysaccharide-Macroporous Hydrophobic Synthetic Polymer Cloth Salmonella LPS-coated macroporous polyester cloth was examined for its suitability as an immunoadsorbent for the purification of anti-Salmonella antibodies. Ten lipopolysaccharide-macroporous polyester cloth segments were incubated with 1 ml of different dilutions of the antiserum and the amount of adsorbed protein eluted with pH 2.2 buffer was measured.

Figure 14:
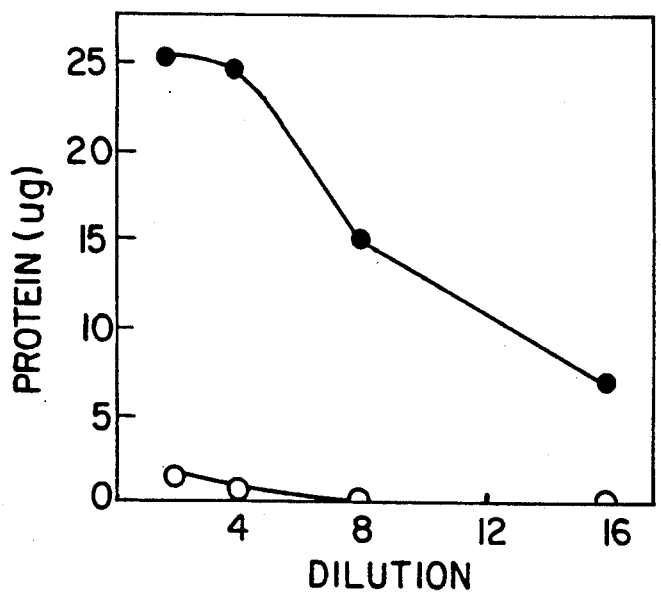

FIG. 14 is a graph showing the recovery of total proteins from lipopolysaccharide-macroporous polyester cloth. Ten *S. typhimurium* lipopolysaccharide-coated macroporous polyester cloth segments (6 mm squares) were incubated with 1 ml of different dilutions of either antiserum or normal serum in PBS for 30 min. The macroporous polyester cloths were then washed and the antibodies eluted with 1 ml of pH 2.2 buffer, then neutralized. The samples were then assayed for total proteins. FIG. 14 shows that the amount of protein recovered was maximal when the antiserum was diluted up to 4 times, but beyond this the protein recovery decreased with increasing dilutions. This indicates that antibody binding sites on the lipopolysaccharide-cloth were saturated at an input serum dilution of 1:4 and lower. Incubating the lipopolysaccharide-macroporous polyester cloth segments with normal serum resulted in only minimal recovery of proteins at the lower serum dilutions and no measurable recovery at serum dilutions of 1:8 and higher. This suggests that the proteins eluted from the LPS-cloth were mostly anti-Salmonella antibodies and that an antibody preparation free of nonspecific serum proteins can be obtained when the antiserum is properly diluted prior to adsorption.

The recovery of the anti-Salmonella antibody titer during the affinity purification was examined by comparing the antibody titer eluted from the LPS-macroporous polyester cloth with the original titer in the input antiserum. The antibody titer was determined in the EIA by measuring the binding of the serially diluted antibodies applied to LPS-cloth segments with an anti-rabbit igG-alkaline phosphatase conjugate. Since the pH 2.2 buffer used in elution caused a five-fold reduction in the capacity of the antibodies to complex with the conjugate, it was necessary to first treat anti-Salmonella antiserum with pH 2.2 buffer, and compare the titer of the treated antiserum with the titers of the pH 2.2 buffer-eluted samples. To avoid prolonged exposure to pH 2.2 the elution was performed only once, although repeated elution would have increased the recovery.

Figure 15:
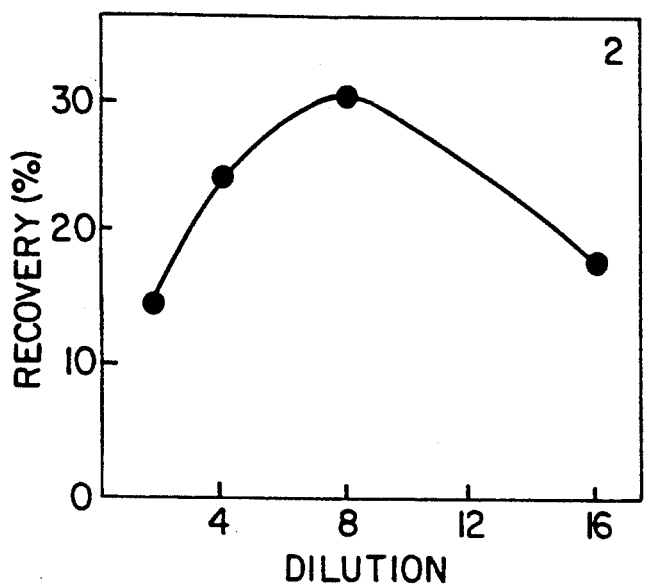

FIG. 15 shows the recovery of anti-Salmonella antibody titer in affinity purification. Lipopolysaccharide-macroporous hydrophobic synthetic polymer cloth segments were incubated with different dilutions of antiserum, and antibodies were eluted with pH 2.2 buffer then neutralized. The anti-Salmonella titers of the eluted samples were then measured by the enzyme immunoassay. FIG. 15 shows that the recovery of anti-Salmonella antibody from the original antiserum was maximal (approximately 30%) using an input serum dilution of 1:8. Thus, subsequent experiments in which antibodies were biotinylated on the lipopolysaccharide-macroporous hydrophobic synthetic polymer cloth were performed.

To examine the reusability of the lipopolysaccharide macroporous hydrophobic-synthetic polymer cloth, the same lipopolysaccharide macroporous hydrophobic-synthetic polymer cloth was used four times for the affinity purification of anti-Salmonella antibodies. There was no appreciable loss in the recovery of purified antibodies during the four cycles of use.

XXII Biotinylation of Anti-Salmonella Antibodies on Lipopolysaccharide-Macroporous Hydrophobic Synthetic Polymer Cloth Biotinylation of the antibodies while immunoadsorbed on the lipopolysaccharide macroporous hydrophobic-synthetic polymer cloth should prevent biotinylation of the antigen binding sites on the antibody molecules, which may reduce the affinity of the antibody for the antigen. It should also simplify the procedure since unused reaction mixture can be readily removed by washing. Therefore, the conditions for biotinylating antibodies immunoadsorbed on lipopolysaccharide macroporous hydrophobic-synthetic polymer cloth were studied by varying the pH, biotinylating reagent concentration, and biotinylation time. The biotinylated antibodies were then eluted with pH 2.2 buffer and neutralized. The eluted biotinylated antibodies were reacted with Salmonella antigens captured on CSA-1 antibody-coated synthetic polymer cloth segments to which $5 \times 10^6$ EDTA-heattreated Salmonella cells had been applied. The bound biotinylated antibodies were then detected with a streptavidin-Alkaline phosphatase conjugate.

Figure 16:
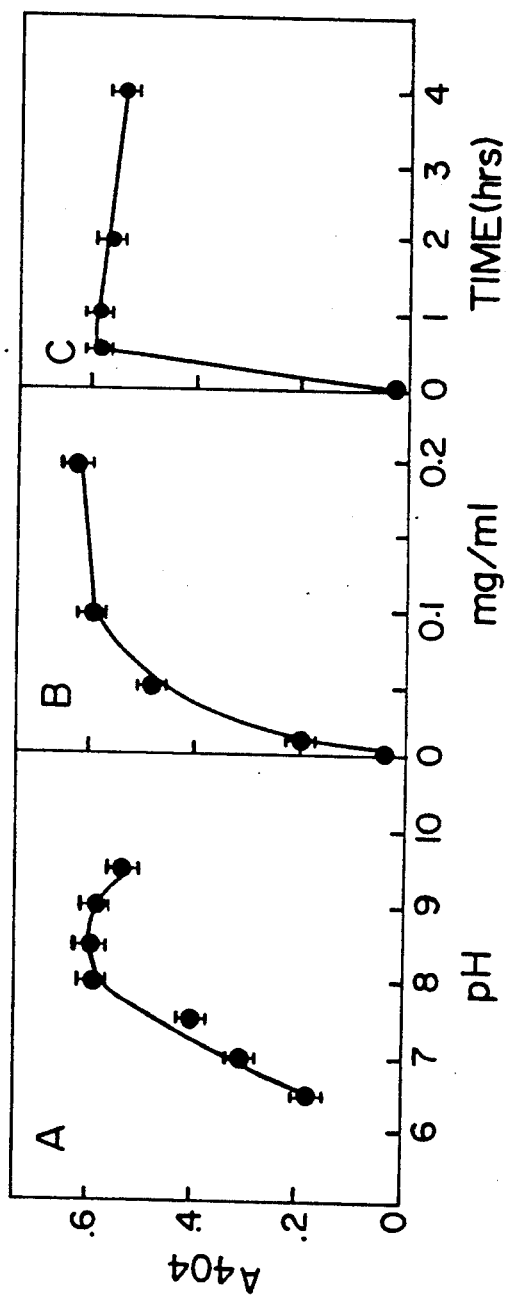

FIG. 16 is a composite graph showing the conditions for the biotinylation of immunoadsorbed antibodies. Antibodies adsorbed to 10 lipopolysaccharide macroporous hydrophobic-synthetic polymer cloth segments were biotinylated using, in FIG. 16A, 1 ml of BACHS (0.2 mg/ml) suspended in either 0.01M acetate (pH 6.5)-0.85% NaCl buffer, PBS (pH 7.0-7.5), or BBS (pH 8.0-9.5), and a reaction time of 60 min; in FIG. 16B, 1 ml of various concentrations of BACHS in BBS (pH 8.0) and a reaction time of 60 min; or in FIG. 16C, using 1 ml of BACHS (0.1 mg/ml in BBS (pH 8.0) and various reaction times. After pH 2.2 elution and neutralization, the biotinylated antibodies were tested in the cloth enzyme immunoassay of Salmonella cells CEIA signals ($A_{370}$) are plotted as mean value $\pm$ S.E. (n=4).

FIG. 16 shows that biotinylation (as judged by the cloth enzyme immunoassay signal) was maximal at a pH of 8.0-8.5 (FIG. 16A), and a biotinylating reagent (BACHS) concentration of 0.1 mg/ml (FIG. 16B) after a reaction time of 30-60 min (FIG. 16C). Therefore, subsequent biotinylation reactions were carried out using 0.1 mg/ml BACHS in BBS (pH 8.0) and a reaction time of 30 min. Under these conditions, the entire procedure (including the affinity purification) required less than 2 h to complete.

XXIII Performance of Biotinylated Antibodies in the Cloth Enzyme Immunoassay

The biotinylated anti-Salmonella antibodies prepared directly on lipopolysaccharide macroporous hydrophobic-synthetic polymer cloth (B-Ab I) were compared with affinity-purified anti-Salmonella antibodies biotinylated in free solution (B-Ab II) and the CSA-1 antibody-alkaline phosphatase conjugate (CSA-1-AP) in the CEIA of *S. typhimurium* antigens. B-Ab II was prepared from antiserum by affinity-purification on lipopolysaccharide macroporous hydrophobic-synthetic polymer cloth as described in Methods, followed by extensive dialysis of the eluted antibodies against BBS and reaction with BACHS (0.1 mg/ml) for 30 min at room temperature, and further dialysis against PBS to remove unreacted BACHS. This procedure required a total of 2 days to complete.

The biotinylated antibodies (B-Ab I and B-Ab II) used in combination with a streptavidin-alkaline phosphatase conjugate, and the CSA-1-AP conjugate, were tested in the cloth enzyme immunoassay of EDTA-heat-treated Salmonella cells using CSA-1 antibody-coated macroporous hydrophobic macroporous hydrophobic synthetic polymer cloth.

Figure 17:
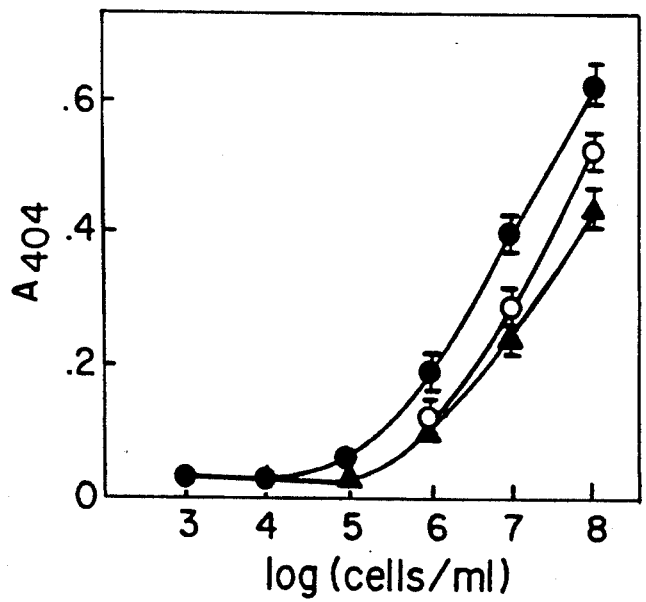

FIG. 17 is a graph showing the cloth enzyme immunoassay of Salmonella antigens. EDTA-heat-treated *S. typhimurium suspensions containing various cell concentrations were incubated with CSA*-1 antibody-coated macroporous hydrophobic synthetic polymer cloth. The captured antigens were then detected using biotinylated antibodies (either B-Ab I or B-Ab II) in combination with a streptavidin-alkaline phosphatase conjugate, or a CSA-1 antibody-alkaline phosphatase conjugate. Cloth enzyme immunoassay signals ($A_{370}$) are plotted as mean value $\pm$ S.E. (n=4).

FIG. 17 shows that the limit of detection was about $10^6$ Salmonella cells/ml using the B-Ab I system and about $5 \times 10^6$ cells/ml using the B-Ab II system or the CSA-1-AP conjugate. Thus, biotinylation of the immunoadsorbed antibodies resulted in a preparation which was significantly more sensitive in the cloth enzyme immunoassay of Salmonella antigens than the antibodies biotinylated in free solution or a commercial antibody-enzyme conjugate. The higher cloth enzyme immunoassay signals obtained with the B-Ab I system may be due to protection of the antigen binding sites of the antibodies against biotinylation.

GENERAL OBSERVATIONS

The immunoassay device of this invention thus employs macroporous hydrophobic cloths as surfaces. Macroporous hydrophobic fabrics (cloths) of plastics, e.g. polypropylene and polyester, are moderately priced because of their large commercial demand as textiles and filters. These cloths offer the following advantages over the previous adsorption supports: they can accommodate a larger volume of sample per area; have a larger surface area for binding immunoreactants and for immunoreactions; are easily washed because of minimum flow resistance; and have both strength and durability.

The immunoassay procedure for detecting antigens in test samples using antibody-coated macroporous hydrophobic synthetic polymer cloths was found to be fast and simple, requiring only the most basic instruments found in most research and clinical laboratories. The assay is also designed so that a qualitative result can be obtained in field test situations, where access to instrumentation is limited or non-existant.

The immunoassay procedure is a rapid and simple procedure which can be applied for the direct detection of antigens in test samples. The assay can be easily and economically adapted for field testing, where a positive result could easily be distinguished from a negative one by visual assessment of the substrate-indicator, (e.g. ABTS), which produces a blue-green colour in the presence of horseradish peroxidase. The "dipstick" format of the field kit makes the manipulation of antibody-coated macroporous hydrophobic synthetic polymer cloth throughout the procedure simple and convenient, so that the test can be performed by untrained hands. Furthermore, this format obviates the need for even common laboratory equipment, and all necessary reagents can be easily supplied in the form of a kit.

Although horseradish peroxidase was used as an indicator, any other suitable enzyme, e.g. alkaline phosphatase and galactosidase, can be employed in the enzyme-antibody conjugate for the detection of antigens. Also, monovalent antigens e.g. toxins (i.e., haptens) can be detected by a competitive assay form of the immunoassay method. In this form of the assay, a standard preparation of the monovalent antigen could be immobilized on the macroporous hydrophobic synthetic polymer cloth surface by adsorption or via a hydrophobic carrier. A test sample suspected of harboring the antigen would then be mixed with an enzyme-antibody conjugate specific for that antigen and incubated with the antigen-coated macroporous hydrophobic synthetic polymer cloth. A negative control in which a representative sample devoid of antigen is mixed with the conjugate would be incubated with a separate antigen-coated macroporous hydrophobic synthetic polymer cloth. Since the presence of free antigen in the test sample should prevent binding of the conjugate to the macroporous hydrophobic synthetic polymer cloth surface, the assay result would be obtained by comparing the amount of enzyme immobilized on the test cloth with that obtained on the negative control cloth. Thus, the immunoassay is amenable to a variety of assay forms, the exact form being determined by the nature of the specific antigen being detected.

The results obtained indicate that several types of macroporous hydrophobic synthetic polymer cloths can be used as solid phases for the adsorption of antibodies. These include macroporous polypropylene, polyester, nylon, and polyethylene cloths, all of which were found to be suitable adsorbents for antibody, e.g. anti-Brucella antibody. All those cloths have proven successful for the detection of antigens such as B. abortus antigens.

It has been found that whole bovine antiserum containing antibody with the appropriate antigen-specificity can be used to coat macroporous hydrophobic synthetic polymer cloth when heated at 75° C. for 10 minutes. This obviates the need for purified antibody preparations, which are time-consuming to produce and may entail some expense. However, in order to minimize the potential for cross-reactions it is preferred that enzyme-antibody conjugates be prepared using purified antibodies. Since the conjugate can be diluted up to 1,000 times, only a small amount of conjugate stock need be prepared in this manner, thus maintaining the ease and economy of each individual test.

The detection of *Brucella abortus* (the causative agent of bovine brucellosis) was used to test the utility of the method of an aspect of this invention. Using the hydrophobic cloth carriers of this invention coated with whole antiserum preheated at 75° C. for 10 minutes, the immunoassay was able to detect 0.3 nanograms of *B. abortus* lipopolysaccharide and $10^4$ *B. abortus* whole cells. The macroporous polypropylene synthetic polymer cloth-based immunoassay was also successfully adapted for the detection of bovine viral diarrhea (BVD) antigen.

As noted above *Brucella abortus* was used to examine the performance of macroporous hydrophobic synthetic polymer cloth as adsorbents of immunoreactants. *B. abortus* causes brucellosis, a serious disease of humans and cattle. Confirmation of the brucellosis by the cultural diagnosis is a slow, complicated process of uncertain sensitivity. Rapid, simple and sensitive detection of Brucella antigens will facilitate confirmation and thus surveillance of brucellosis and its control.

Macroporous polypropylene cloth has been found to have excellent properties as a solid phase in the immunoassay. The fact that macroporous polypropylene filter cloth is available in a nonwoven filter cloth form gives it the added advantage of retaining a stable fabric structure (i.e., no loose edges) even under agitated conditions. Furthermore, macroporous polypropylene filter cloth is easily adapted for the preparation of commercial test kits.

The detection of *B. abortus* antigens by antibody-coated macroporous hydrophobic synthetic polymer cloths is only one example of the method of this invention for the study of microbial antigen detection by cloth enzyme immunoassay. The immunoassay method is amenable to the detection of any given number of microbial antigens, provided that these are sufficiently small to be retained on the antibody-coated macroporous hydrophobic synthetic polymer cloths throughout the assay procedure. In cases where antigens, e.g. whole cells, are too large for effective retention on the macroporous hydrophobic synthetic polymer cloths, important antigenic components thereof might be dissociated from the surface by simple chemical or mechanical means so as to facilitate detection.

For example, the present invention is applicable to many immunologically reactive materials, e.g. proteins, peptides, polysaccharides, etc. which are of decisive significance for an immunological determination, i.e. the presence of these materials is the determining factor in the immunological test procedure. These materials can be detected in the body fluids of humans and animals using immunological principles or can serve for their detection. Especially suitable immunologically-reactive materials are pathogenic and facultatively pathogenic organisms such as, for example, parasites, protozoa, bacteria or viruses or their immunologically active components, isolated antibodies from humans and animals, serum constituents, toxins, hormones, enzymes, alkaloids, cell and tissue extracts, substances with a small molecular weight such as, for example, insulin, anngiotensin and urokinase, biogenic amines, blood cells, particles chemically or physically covered with antigens or antibodies, such as, for example, erythrocytes or latex particles.

The following Table provides a selection of typical diseases or conditions which can be determined with the aid of the immunonoassay device in accordance with the present invention according to the immunologically reactive materials lyophilised thereon.

TABLE

| Antigen | Disease |
| --- | --- |
| Toxoplasma gondii | Toxoplasmosis |
| Entamoeba histolytica | Amoebiasis |
| Trypanosoma cruzi | Chagas |
| Trypanosoma gambiense/rhodesiense | Sleeping sickness |
| Leishmania donovani | Leishmaniasis |
| Schistosoma mansoni | Schistosomiasis |
| Echinococcus granulosus | Echinococcosis |
| Filariae | Filariasis |
| Fasciola hepatica | Fascioliasis |
| Plasmodia | Malaria |
| Candida species | Candidiasis |
| Aspergilli | Asperigillosis |
| Mycropolyspora faeni/ Micromonospora vulgaris | Farmer's lung |
| Treponema pallidum | Syphilis |
| Neisseria gonorrhoeae | Gonorrhea |
| Neissseria meningitis | Meningitis |
| Brucella abortus | Brucellosis |
| Mycoplasma pneumoniae | Pneumonia |
| Australia antigen | Acute hepatitis |
| Herpes simplex virus | Herpes simplex |
| Influenza virus | Flu |
| Cell nuclei | Systemic lupus erythrematosis or Scleroderma |
| Cryptococci | Cryptococcosis |
| Torulopsis species | Systemic mycosis |
| H-antigen (flagellar) | Salmonella |

According to the present invention macroporous cloths of hydrophobic fibers, e.g., polyester, have advantages as adsorbents for immunoreactants in enzyme immunoassay. As compared to non-porous solid phases, e.g., microtiter plates, as in the prior art, they accommodate larger volumes of sample for immediate immunoreaction over a larger surface, thus yielding faster immunoreactions. The use of such macroporous hydrophobic synthetic polymer cloth permits the development of rapid enzyme immunoassays that are much needed in the biotechnological and medical fields.

A second advantage of the macroporous hydrophobic synthetic polymer cloths is that they can be readily washed with small volumes of washing solutions without use of laboratory facilities. The method of the present invention involves washing the cloth on an absorbent pad (e.g. a disposable diaper) dropwise with a small volume (less than 0.5 ml) of the buffer. The absorbent pad can be placed in a sealable disposable container if the test sample is either toxic or pathogenic and must be contained. These attributes are believed to make the macroporous hydrophobic synthetic polymer cloth an ideal adsorbent for enzyme immunoassay under field conditions where relatively small numbers of samples need to be tested.

The present invention also provides a simple and rapid assay for anti-Salmonella antibodies in serum or other fluids, e.g., for antibodies in chicken egg yolk. The method is believed to be useful as a tool for monitoring sanitary conditions in rearing facilities when it is firmly established that an elevated level of anti-Salmonella IgG in eggs is related to the extent of Salmonella contamination. When the use of individual macroporous hydrophobic synthetic polymer cloth segments is too cumbersome for processing larger numbers of eggs, a dot blot format involving large sheets of lipopolysaccharide-cloth able to accommodate multiple samples can be used for qualitative testing.

The present invention also provides a method for the application of antigen-coated macroporous polyester cloth to the rapid measurement of specific antibodies on the basis of the initial rate of immunoreaction of antibody with the immobilized antigen. This method requires only one third of the time necessary to complete the enzyme immunoassay using a microtiter plate as in the prior art. This time may be reduced further by the use of a more sensitive enzyme substrate system. Furthermore, this initial rate method is believed to eliminate problems with false positive reactions caused by non-specific interactions of test sample components with the solid phase, since only highly specific antibodies would be expected to bind during the instantaneous incubation with the macroporous hydrophobic synthetic polymer cloth. The rapid assay was made possible by the use of a macroporous hydrophobic synthetic polymer cloth as the solid phase, since the macroporous hydrophobic macroporous hydrophobic synthetic polymer cloth provides a large surface for rapid immunoreaction with the antibody and allows for immediate washing after sample application to give an initial rate determination. The "instantaneous" cloth enzyme immunoassay approach is believed to have many useful applications for the rapid assay of smaller numbers (e.g., a few dozen) of antibody samples as well as other immunoreactive substances.

The present invention also provides a method wherein heating Salmonella cells in EDTA leads to the dissociation of their antigens into a non-sedimentable form, which permits the preparation of solid-free liquid samples from solid-rich samples, e.g., poultry meat, for antigen detection by enzyme immunoassay. Furthermore, the dissociated antigens, because of their smaller sizes, interact more efficiently with the antibody adsorbed onto the cloth than cell-associated antigens. It is also believed that dissociation causes the exposure of additional epitopes which can react with the antibody used in the present studies.

The present invention also provides a method for detecting low levels of antigens by concentration from large volumes of sample onto the antibody-coated macroporous hydrophobic synthetic polymer cloth with or without a prior brief enrichment step. In the case of solid-rich samples containing very high numbers of enterobacteria other than salmonellae, e.g., feces, potential problems with cross-reactions in the cloth enzyme immunoassay are believed to be eliminated by the use of a monoclonal antibody specific for Salmonella instead of the polyclonal reagent used presently. The procedure is also believed to be applicable to the detection of other EDTA-heat sensitive bacteria in solid-rich samples.

Preliminary studies indicate its applicability to the detection of enteropathogenic Campylobacter.

The present invention also provides a procedure wherein the anti-Salmonella antibodies in an antiserum were immunoadsorbed onto lipopolysaccharide-coated polyester cloth, biotinylated and then eluted. The biotinylated affinity purified antibody required less than 2 hours to prepare, and when used in combination with a streptavidin-alkaline phosphatase conjugate permitted the detection of $10^6$ Salmonella cells/ml in an enzyme immunoassay.

Thus, the present invention also provides for the application of lipopolysaccharide-coated macroporous polyester cloth in the affinity purification and biotinylation of anti-Salmonella antibodies. This method was not only rapid, simple and economical, but also resulted in the preparation of a biotinylated antibody which permited the sensitive detection of Salmonella antigens by the cloth enzyme immunoassay. The method is applicable to the preparation of biotinylated antibodies not only to other Gram-negative bacteria (e.g., Campylobacter), but also to other hydrophobic antigens adsorbable to polyester cloth. In instances where antigens (e.g., some proteins) might be sensitive to the low pH exposure, alternative elution conditions may be required if repeated use of the antigen-cloth is desired. Since macroporous polyester cloth has excellent flow characteristics due to its macroporosity and non-compressibility, its use in a large scale column operation for the preparation of larger quantities of biotyinylated antibodies should be feasible.

CONCLUSION

From the foregoing description, one skilled in the art can easily ascertain the essential characteristics of this invention, and without departing from the spirit and scope thereof, can make various changes and modifications of the invention to adapt it to various usuages and conditions. Consequently, such changes and modifications are properly, equitably, and "intended" to be, within the full range of equivalence of the following claims.

What we claim is:

1. An immunoassay device for detection of an antigen comprising the combination of: (a) a macroporous hydrophobic synthetic polymer cloth, said cloth having a thickness more than about 200 µm and having spaces between fibres exceeding about 20 µm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; and (b) an antibody directly adsorbed thereon, and directly absorbed and immobilized therein.

2. The immunoassay device of claim 1 wherein said cloth is selected from the group consisting of woven or non-woven polypropylene, polyester, nylon, and polyethylene cloths.

3. An immunoassay device for detection of an antibody comprising the combination of: (a) a macroporous hydrophobic synthetic polymer cloth, said cloth having a thickness more than about 200 µm and having spaces between fibres exceeding about 20 µm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; and (b) an antigen directly adsorbed thereon, and directly absorbed and immobilized therein.

4. The immunoassay device of claim 3 wherein said cloth is selected from the group consisting of woven or non-woven polypropylene, polyester, nylon, and polyethylene cloths.

5. An immunoassay device comprising the combination of: (a) a macroporous hydrophobic synthetic polymer cloth, said cloth having a thickness more than about 200 µm and having spaces between fibres exceeding about 20 µm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; (b) antibodies directly adsorbed therein and directly absorbed and immobilized thereon; and (c) specific antigens from a selected test sample, captured by said adsorbed, absorbed and immobilized antibodies.

6. The immunoassay device of claim 5 wherein said antibodies and said specific antigens respectively comprise bovine serum albumin (BSA) directly adsorbed therein and directly absorbed and immobilized thereon, and anti-BSA immunoglobulin G antibody (IgG) in rabbit serum captured therein by said BSA.

7. An immunoassay device comprising the combination of: (a) a macroporous hydrophobic synthetic polymer cloth, said cloth having a thickness more than about 200 µm and having spaces between fibers exceeding about 20 µm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; (b) antigens directly adsorbed therein and directly absorbed and immobilized thereon; and (c) specific antibodies from a selected test sample, captured by said adsorbed, absorbed and immobilized antigens.

8. The immunoassay device of claim 7 wherein said captured antibodies comprise anti-BSA IgG which are detectable using an anti-rabbit IgG peroxidase conjugate.

9. The immunoassay device of claim 7 wherein said antigens and said specific antibodies respectively comprise Salmonella lipopolysaccharide directly adsorbed therein and directly absorbed and immobilized thereon, and specific antibodies in egg yolk, captured therein by said Salmonella lipopolysaccharide.

10. The immunoassay device of claim 7 wherein said antigens and said specific antibodies respectively comprise a selected lipopolysaccharide directly adsorbed therein and directly absorbed and immobilized thereon, and specific antibodies in a selected sample, captured therein by said selected lipopolysaccharide.

11. The immunoassay device of claim 10 wherein said captured specific antibodies comprise specific antibodies in egg yolk which are detectable using an anti-chicken IgG-peroxidase conjugate.

12. The immunoassay device of claim 7 wherein said antigens and said specific antibodies respectively comprise Salmonella lipopolysaccharide directly adsorbed therein and directly absorbed and immobilized thereon, and goat anti-Salmonella antibody standards captured by said Salmonella lipopolysaccharide.

13. An immunoassay device comprising the combination of: (a) a macroporous synthetic polymer cloth, said cloth having a thickness more than about 200 μm and having spaces between fibres exceeding about 20 μm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; (b) a coating of a suitable adsorbable antigen directly adsorbed thereon and directly absorbed and immobilized therein; and (c) antibodies in an antiserum immunoadsorbed on said antigen coating.

14. An immunoassay device comprising the combination of: (a) a macroporous synthetic polymer cloth, said cloth having a thickness more than about 200 μm and having spaces between fibres exceeding about 20 μm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance; (b) a coating of a lipopolysaccharide directly adsorbed thereon and directly absorbed and immobilized therein; and (c) antibodies in an antiserum immunoadsorbed on said lipopolysaccharide coating.

15. An immunoassay method for detecting an antigen, comprising the steps of: a) treating a surface of a macroporous hydrophobic synthetic polymer cloth, said cloth having a thickness more than about 200 μm and having spaces between fibres exceeding about 20 μm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance, with an antibody, thereby to have said antibody directly adsorbed thereon and directly absorbed and immobilized therein, thereby to provide an immunoassay cloth; b) incubating said immunoassay cloth with a sample to be tested for the antigen, thereby to adsorb an antigen therein and to provide an antigen-treated incubated cloth; c) washing said antigen-treated incubated cloth with a buffer to remove unadsorbed material; d) incubating said washed cloth with an enzyme-antibody conjugate prepared by coupling to an enzyme purified antibodies specific for said antigen to be assayed, thereby to provide an incubated cloth; e) washing said incubated cloth with a buffer to remove unreacted conjugate; and f) detecting remaining enzyme-antibody conjugate by incubating said washed incubated cloth in a chromogenic substrate indicator solution to produce a visible colour upon product formation.

16. An immunoassay method for detecting an antigen, comprising the steps of: a) treating a surface of a macroporous hydrophobic synthetic polymer cloth, said cloth having a thickness more than about 200 μm and having spaces between fibres exceeding about 20 μm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance, with an antibody, thereby to have an antibody directly adsorbed thereon and directly absorbed and immobilized therein, and thereby to provide an intermediate immunoassay cloth; b) applying to the surface of said intermediate immunoassay cloth, a mixture of the antigen being assayed and an enzyme-antibody conjugate prepared by coupling to an enzyme purified antibodies specific for said antigen being assayed, thereby to provide an immunoassay cloth; c) treating a control identical macroporous hydrophobic synthetic polymer cloth with a mixture of said antigen being assayed and an enzyme-antibody conjugate prepared by coupling to an enzyme purified antibodies specific for the antigen being assayed, to provide a control cloth; d) incubating both said immunoassay cloth and said control cloth substantially simultaneously; e) washing said incubated immunoassay cloth and said incubated control cloth with an identical buffer solution; and f) detecting said antigen by incubation of both said immunoassay cloth and said control cloth in a chromogenic substrate indicator solution to produce a visible colour upon product formation, the amount of antigen being determined by the difference in intensity of the colour between said control cloth and said immunoassay cloth.

17. An immunoassay method for detecting an antibody, comprising the steps of: a) treating a surface of a macroporous hydrophobic synthetic polymer cloth, said cloth having a thickness more than about 200 μm and having spaces between fibres exceeding about 20 μm in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance, with an antigen, thereby to have an antigen directly adsorbed thereon and directly absorbed and immobilized therein, thereby to provide an immunoassay cloth; b) incubating said immunoassay cloth with a sample to be tested for the antibody, thereby to adsorb antibody therein and to provide an incubated cloth; c) washing said incubated cloth with a buffer to remove unadsorbed material and to provide a washed cloth; d) incubating said washed cloth with an enzyme-antiglobulin antibody conjugate prepared by coupling to an enzyme purified antigens specific for said antibody to be assayed; e) washing said incubated cloth with a buffer to remove unreacted conjugate; and f) detecting remaining enzyme-antiglobulin antibody conjugate by incubating said washed incubated cloth in a chromogenic substrate indicator solution to produce a visible colour upon product formation.

18. An immunoassay method for detecting an antibody, comprising the steps of: a) treating a surface of a macroporous hydrophobic synthetic polymer cloth, said cloth having a thickness more than about 200 μm and having spaces between fibres exceeding about 20 μm in diameter, said cloth to have a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance, with an antigen, thereby to have an antigen directly adsorbed thereon and directly absorbed and immobilized therein, thereby to provide an intermediate immunoassay cloth; b) applying to the surface of said intermediate immunoassay cloth, a mixture of the antibody being assayed and an enzyme-antigen conjugate prepared by coupling to an enzyme purified antigens specific for said antibody being assayed, thereby to provide an immunoassay cloth; c) treating a control identical macroporous hydrophobic synthetic polymer cloth with a mixture of said antibody being assayed and an enzyme-antigen conjugate prepared by coupling to an enzyme purified antigens specific for the antibody being assayed, to provide a control cloth; d) incubating both said immunoassay cloth and said control cloth substantially simultaneously; e) washing said incubated immunoassay cloth and said control cloth with an identical buffer solution; and f) detecting said antibody by incubation of both said immunoassay cloth and said control cloth in a chromogenic substrate indicator solution to produce a visible colour upon product formation, the amount of antibody being determined by the difference in intensity of the colour between said control cloth and said immunoassay cloth.

19. A method for the extraction of lipopolysaccharide antigens from solid samples, and for the concentration of such antigens which are present in large volumes of sample, by directly adsorbing and absorbing lipopolysaccharide antigens onto an antibody-coated macroporous hydrophobic cloth, said cloth having a thickness more than about 200 $\mu$m and having spaces between fibres exceeding about 20 $\mu$m in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance for subsequent detection on said cloth by cloth enzyme immunoassay techniques, which method comprises the steps of: a) heating a solid sample containing said antigen in the presence of a chelating agent for short period of time, thereby to chelate divalent cations, and to disrupt the lipopolysaccharide-containing outer membrane of Gram-negative bacteria; b) recovering said lipopolysaccharide antigens in non-sedimentable form; (c) separating said antigens to obtain a solid-free liquor; and (d) using said solid-free liquor as the sample for carrying out said extraction and concentration.

20. An immunoassay procedure comprising the steps of: a) treating a macroporous hydrophobic synthetic polymer cloth, said cloth having a thickness more than about 200 $\mu$m and having spaces between fibres exceeding about 20 $\mu$m in diameter, said cloth having a Frazier Air Permeability in CFM/ft$^2$ at 0.5" H$_2$O of from about 215 to about 750 for thicknesses of about 11 mils to about 40 mils, respectively, said cloth thereby having a structure so that it can accommodate a large volume of liquid per surface area, it has a large surface area and it has a minimum flow resistance, with lipopolysaccharide; b) incubating said cloth with a test sample purported to contain B. abortus antigen; c) washing said incubated cloth with a buffer to remove any unadsorbed said B. abortus antigen; d) further incubating said washed cloth with an enzyme-antibody conjugate prepared by coupling purified antibody specific for said B. abortus antigen to an indicator enzyme; e) washing said further incubated cloth with buffer to remove unreacted conjugate; and f) detecting remaining conjugate by incubation in a chromogenic substrate-indicator solution which produces a visible colour upon product formation.

21. A rapid method for assaying anti-Salmonella IgG in chicken egg yolk, which comprises the steps of: a) capturing specific antibodies in egg yolk onto a macroporous hydrophobic cloth, said cloth having a thickness more than about 200 μm and having spaces between fibres exceeding about 20 μm in diameter, said cloth having a Frazier Air Permeability in CFM/ft$^2$ at 0.5" $H_2O$ of from about 215 to about 750 for thicknesses of about 11 mils to about 40 mils, respectively, said cloth thereby having a structure so that it can accommodate a large volume of liquid per surface area, it has a large surface area and it has a minimum flow resistance, said cloth being coated with Salmonella lipopolysaccharide; and b) detecting said antibodies using an anti-chicken IgG-peroxidase conjugate.

22. A rapid immunoassay method which comprises the steps of: a) adsorbing antigens on a macroporous hydrophobic cloth, said cloth having a thickness more than about 200 μm and having spaces between fibres exceeding about 20 μm in diameter, said cloth having a Frazier Air Permeability in CFM/ft$^2$ at 0.5" $H_2O$ of from about 215 to about 750 for thicknesses of about 11 mils to about 40 mils, respectively, said cloth thereby having a structure so that it can accommodate a large volume of liquid per surface area, it has a large surface area and it has a minimum flow resistance; b) capturing specific antibodies from a test sample on said cloth; c) detecting said antibodies using an antiglobulin antibody-enzyme conjugate, which binds to the captured antibody; and d) assaying said enzyme using a chromogenic substrate.

23. A method for preparing biotinylated, affinity-purified antibodies which comprises: a) immunoadsorbing anti-Salmonella antibodies in a serum onto a lipopolysaccharide-coated macroporous hydrophobic synthetic cloth, said cloth having a thickness more than about 200 μm and having spaces between fibres exceeding about 20 μm in diameter, said cloth having a Frazier Air Permeability in CFM/ft$^2$ at 0.5" $H_2O$ of from about 215 to about 750 for thicknesses of about 11 mils to about 40 mils, respectively, said cloth thereby having a structure so that it can accommodate a large volume of liquid per surface area, it has a large surface area and it has a minimum flow resistance; b) biotinylating said antibodies on said cloth; and c) eluting said biotinylated antibodies therefrom.

24. A method for the rapid assay of specific antibodies comprising the steps of: (a) coating a macroporous hydrophobic cloth, said cloth having a thickness more than about 200 μm and having spaces between fibres exceeding about 20 μm in diameter, said cloth having a Frazier Air Permeability in CFM/ft$^2$ at 0.5" $H_2O$ of from about 215 to about 750 for thicknesses of about 11 mils to about 40 mils, respectively, with a selected antigen, thereby to adsorb said antigen thereon and to absorb and immobilize said antigen therein; and (b) rapidly capturing and detecting associated antibodies in any body fluid through the use of said antigen-coated cloth.

25. A method for the extraction and concentration of antigen which comprises the steps of: (a) coating a macroporous hydrophobic cloth, said cloth having a thickness more than about 200 μm and having spaces between fibres exceeding about 20 μm in diameter, said cloth having a Frazier Air Permeability in CFM/ft$^2$ at 0.5" $H_2O$ of from about 215 to about 750 for thicknesses of about 11 mils to about 40 mils, respectively, with selected antibodies; (b) extracting selected gram negative antigens from large volumes of bacteria by heating said bacteria in the presence of an organic sequestering agent; and (c) rapidly assaying said antigens using said antibody-coated cloth.

26. A method for the purification and biotinylation of specific antibodies which comprises the steps of: (a) coating a macroporous hydrophobic cloth, said cloth having a thickness more than about 200 $\mu$m and having spaces between fibres exceeding about 20 $\mu$m in diameter, said cloth having a Frazier Air Permeability in CFM/ft$^2$ at 0.5" H$_2$O of from about 215 to about 750 for thicknesses of about 11 mils to about 40 mils, respectively, with selected antigens; (b) affinity purifying biotinylated antibodies using said antigen coated cloth; and (c) using said affinity purified biotinylated antibodies as a reagent in an enzyme immunoassay procedure.

* * * * *